United States Patent
D'Hondt et al.

(10) Patent No.: US 12,257,245 B2
(45) Date of Patent: Mar. 25, 2025

(54) METHODS AND COMPOSITIONS FOR INHIBITION OF EGF/EGFR PATHWAY IN COMBINATION WITH ANAPLASTIC LYMPHOMA KINASE INHIBITORS

(71) Applicant: In3Bio Ltd., Hamilton (BM)

(72) Inventors: Erik D'Hondt, Bazel (BE); Miguel Ángel Molina-Vila, Badalona (ES)

(73) Assignee: In3Bio Ltd., Hamilton (BM)

(*) Notice: Subject to any disclaimer, the term of this patent is extended or adjusted under 35 U.S.C. 154(b) by 22 days.

(21) Appl. No.: 16/534,230

(22) Filed: Aug. 7, 2019

(65) Prior Publication Data

US 2020/0046690 A1 Feb. 13, 2020

Related U.S. Application Data

(60) Provisional application No. 62/822,290, filed on Mar. 22, 2019, provisional application No. 62/760,529, filed on Nov. 13, 2018, provisional application No. 62/748,772, filed on Oct. 22, 2018, provisional application No. 62/727,056, filed on Sep. 5, 2018, provisional application No. 62/715,351, filed on Aug. 7, 2018.

(51) Int. Cl.

| | | |
|---|---|---|
| *A61K 31/4545* | (2006.01) | |
| *A61K 31/519* | (2006.01) | |
| *A61K 31/5377* | (2006.01) | |
| *A61K 31/675* | (2006.01) | |
| *A61K 39/00* | (2006.01) | |
| *A61K 39/395* | (2006.01) | |
| *A61P 35/00* | (2006.01) | |

(52) U.S. Cl.
CPC ........ *A61K 31/4545* (2013.01); *A61K 31/519* (2013.01); *A61K 31/5377* (2013.01); *A61K 31/675* (2013.01); *A61K 39/001131* (2018.08); *A61K 39/3955* (2013.01); *A61P 35/00* (2018.01); *A61K 2039/545* (2013.01)

(58) Field of Classification Search
CPC .............. A61K 31/519; A61K 31/5377; A61K 31/4545; A61K 31/675; A61K 39/3955; A61K 2039/545; A61P 35/00
See application file for complete search history.

(56) References Cited

U.S. PATENT DOCUMENTS

2012/0294867 A1 11/2012 Denis et al.

FOREIGN PATENT DOCUMENTS

| CN | 107949401 A | 4/2018 |
|---|---|---|
| RU | 2654695 C1 | 5/2018 |

OTHER PUBLICATIONS

Garcia-Roman Silvia et al. "Antitumor effects of anti-EGF antibodies generated by vaccination in NSCLC tumor cells". Cancer Research vol. 78, No. 13, Suppl. S, p. 837, Jul. 2018.

Rodriguez Pedro C. et al. "A Phase III Clinical Trial of the Epidermal Growth Factor Vaccine CIMAvax-EGF as Switch Maintenance Therapy in Advanced Non-Small Cell Lung Cancer Patients". Clinical Cancer Research, vol. 22, No. 15, Aug. 2016, pp. 3782-3790.

Taniguchi Hirokazu et al. "Amphiregulin triggered epidermal growth factor receptor activation confers in vivo crizotinib-resistance of EML4-ALK lung cancer and circumvention by epidermal growth factor receptor inhibitors." Cancer Science Jan. 2017. vol. 108, No. 1, pp. 53-60.

Kawamura et al. Lung Cancer Treatment with Necitumumab, 2016.

Neninger Vinageras E, et al. Phase II randomized controlled trial of an epidermal growth factor vaccine in advanced non-small-cell lung cancer. J Clin Oncol. 2008, v.20, No. 26(9), p. 1452-1458, doi: 10.1200/JCO.2007.11.5980.

Cheng, J. Y., & Kananathan, R. CIMAvax EGF vaccine for stage IIIb/IV non-small cell lung carcinoma. Human Vaccines & Immunotherapeutics, 2012, v.8, No. 12, p. 1799-1801. doi: 10.4161/hv.21744.

*Primary Examiner* — Ruixiang Li
(74) *Attorney, Agent, or Firm* — Withers Bergman LLP; John C. Serio

(57) ABSTRACT

A method of treating patients suffering from cancers driven by deregulated Human Epidermal Growth Factor Receptor (HER1/Human EGFR) comprising administering to a patient in need of such treatment a flexible and active regimen for combining Anaplastic Lymphoma Kinase Inhibitors (ALK Inhibitors) and anti-EGF antibodies for inhibition of the pathway activated by EGF-EGFR binding (mAb). The anti-EGF antibodies can be produced by active immunization or provided passively by the administration of antibodies that are anti-EGF. The method comprises ALK Inhibitors administered according to a continuous regimen based on an average daily dose in the range of 10 to 250 mg and the mAb is co-administered either actively or passively according to a dosing regimen achieving a therapeutic effective amount repeated thrice, twice or once a week, once in two weeks, once in three weeks or at least once monthly.

3 Claims, 63 Drawing Sheets

Specification includes a Sequence Listing.

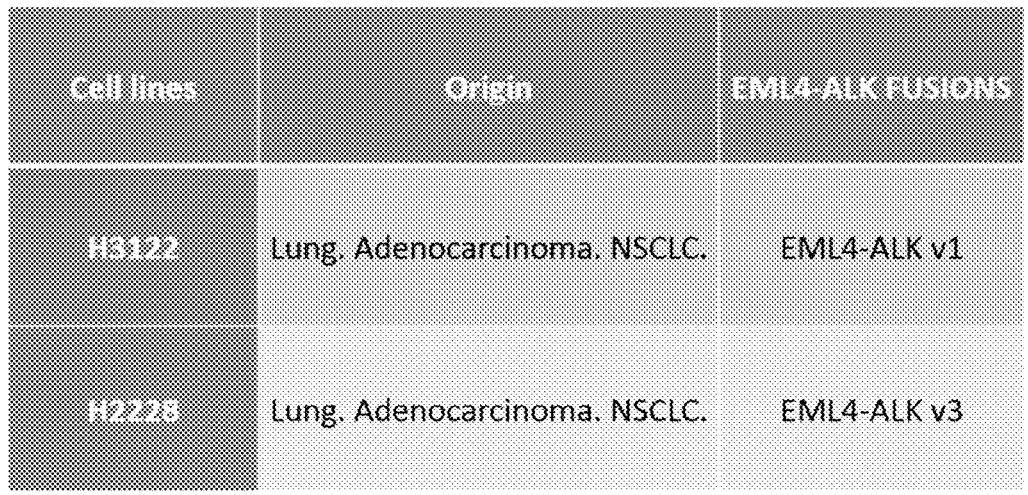
FIG. 1
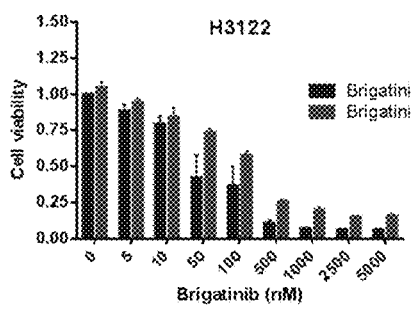
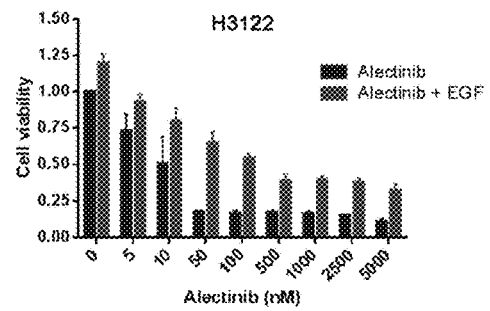
FIG. 2A
FIG. 2B

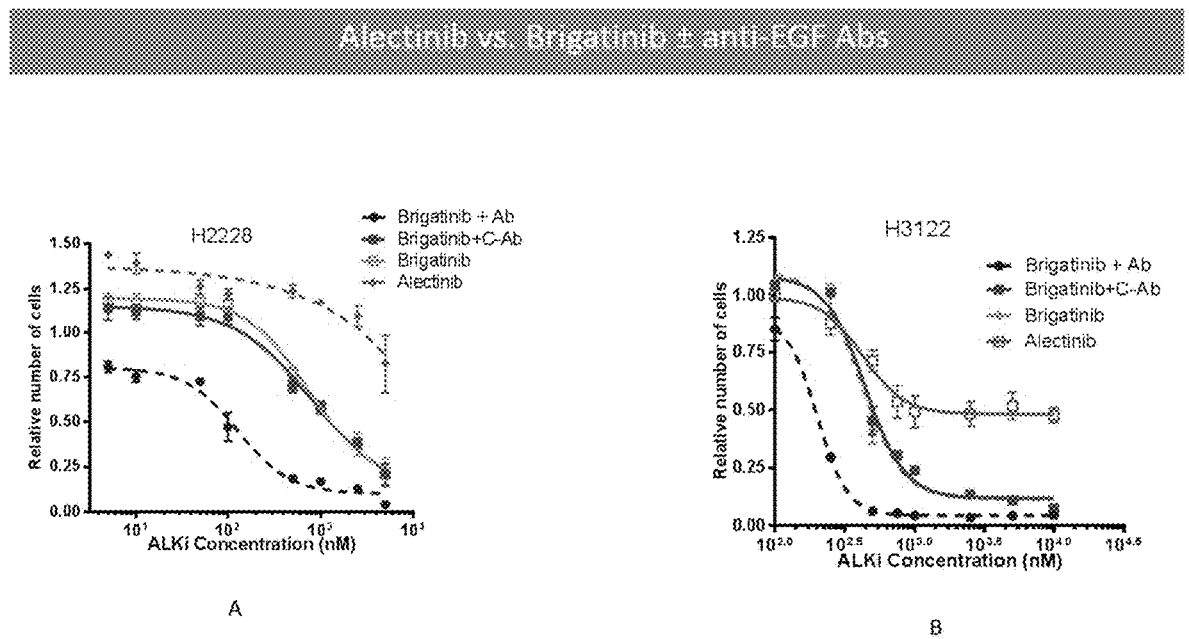
FIG. 7A  FIG. 7B
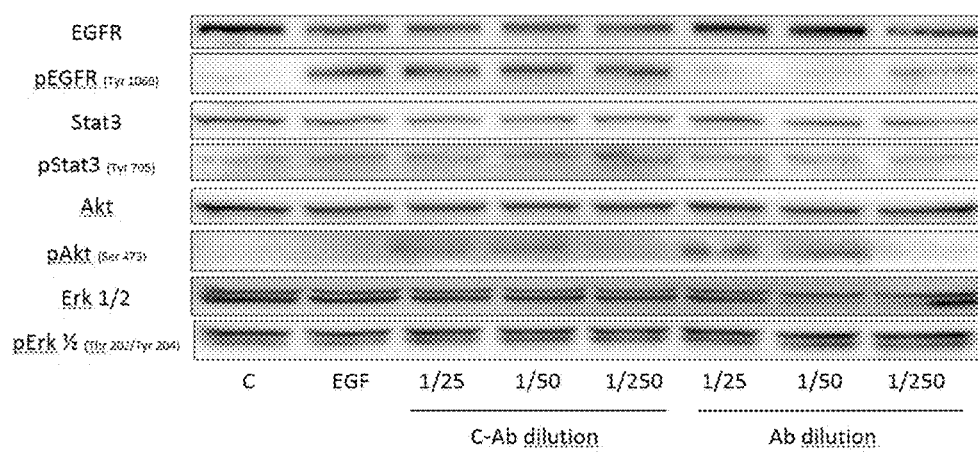
FIG. 8

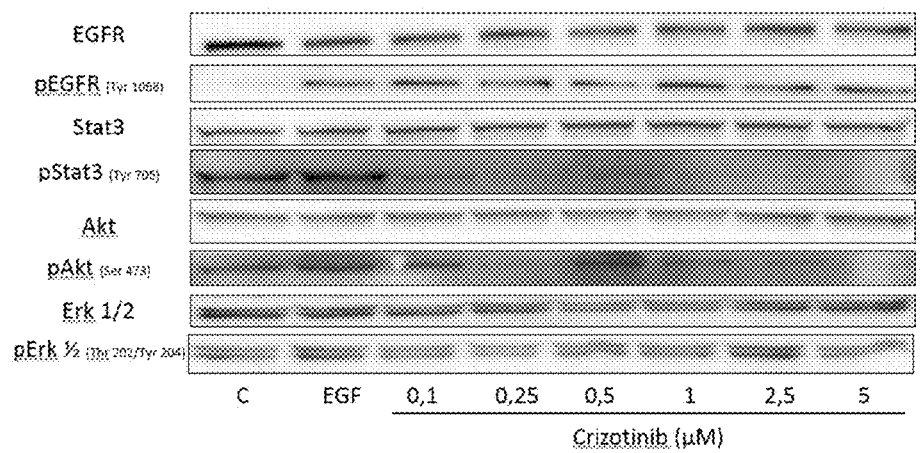
FIG. 10
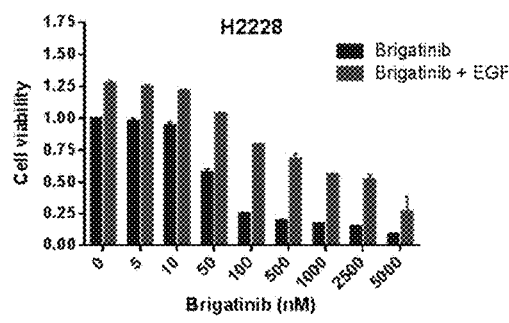
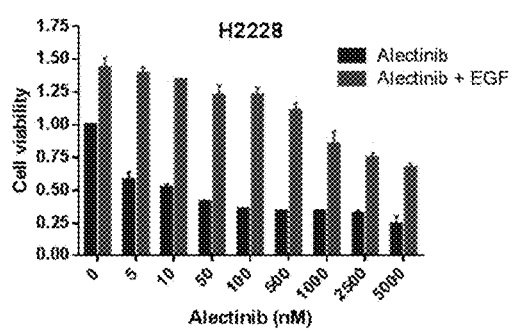
FIG. 11A    FIG. 11B

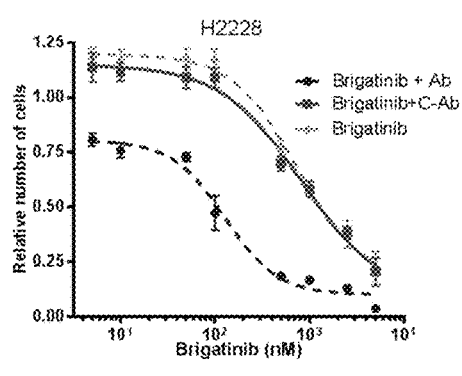
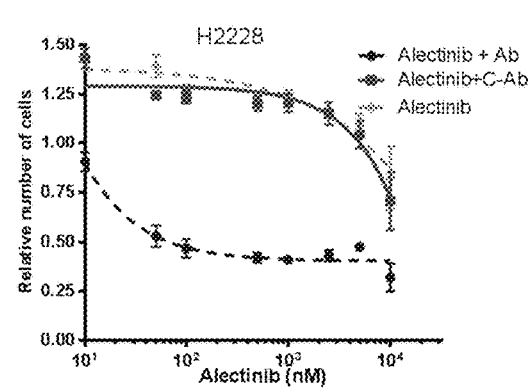
FIG. 16A                    FIG. 16B

*BRAF* mutant cell line

Dose-Response of trametinib at 2 hours of incubation in HT29 cell line

Anti-EGF VacAbs with trametinib at 2 hours of incubation in HT29 cell line

Flow cytometry

Cell cycle & Apoptosis

KRAS mutant cell lines (A549 & DLD1)

ALK translocated cell lines (H2228 & H3122)

| Cell lines | Origin | KRAS mutation |
|---|---|---|
| A549 | Lung. Adenocarcinoma. NSCLC. | G12S |
| H23 | Lung. Adenocarcinoma. NSCLC. | G12C |
| DLD1 | Colon. Adenocarcinoma. | G13D |
| LS174T | Colon. Adenocarcinoma. | G12C |

FIG. 39

Effects of EGF on the activity of trametinib in the A549 cell line

METHODS AND COMPOSITIONS FOR INHIBITION OF EGF/EGFR PATHWAY IN COMBINATION WITH ANAPLASTIC LYMPHOMA KINASE INHIBITORS

CROSS-REFERENCE TO RELATED APPLICATIONS

This application claims priority to and the benefit of U.S. Provisional Patent Application No. 62/715,351, filed on Aug. 7, 2018, U.S. Provisional Patent Application No. 62/727,056, filed on Sep. 5, 2018, U.S. Provisional Patent Application No. 62/748,772, filed on Oct. 22, 2018, U.S. Provisional Patent Application No. 62/760,529, filed on Nov. 13, 2018, and U.S. Provisional Patent Application No. 62/822,290, filed on Mar. 22, 2019, the contents of which are incorporated herein by reference in their entirety for all purposes.

SEQUENCE LISTING

The instant application contains a modified sequence listing which has been filed electronically in ASCII format and is hereby incorporated by reference in its entirety. Said ASCII copy, created on Nov. 22, 2024, is named BN00011.0077US_SL.txt and is 6,728 bytes in size.

FIELD OF THE INVENTION

Embodiments of the present invention are directed to methods for treating and preventing disease conditions, such as cancer, particularly in those individuals who have developed a resistance or who are not responsive to Anaplastic Lymphoma Kinase Inhibitors (ALK Inhibitors) therapy.

BACKGROUND OF INVENTION

Non-small-cell lung cancer (NSCLC) is the leading cause of cancer related deaths in the world and despite recent advances in treatment and diagnosis, the 5-year survival remains at ~16%. This poor outcome is largely due to the advanced disease stage, the robust nature of the disease and degree of metastasis at diagnosis. Although significant advances have been made in elucidating the genomic abnormalities that cause malignant cancer cells, currently available chemotherapy remains unsatisfactory, and the prognosis for the majority of patients diagnosed with cancer remains troubling.

Most chemotherapeutic agents act on a specific molecular target thought to be involved in the development of the malignant phenotype. However, a complex network of signaling pathways regulate cell proliferation and the majority of malignant cancers are facilitated by multiple genetic abnormalities in these pathways. Although treatment of lung cancers with standard cytotoxic chemotherapies has been optimized for efficacy, more recent approaches to NSCLC therapeutics are based on classification of NSCLC into molecular subsets based on their distinct oncogene driver. These molecular drivers of NSCLC can be attacked therapeutically with targeted agents directed against the specific oncogenes.

Most previous chemotherapy drugs for cancer were non-selective in their activity. Although their exact mechanisms of action were varied and complex, they generally worked by damaging cells undergoing mitosis, which is usually more common in malignant tumors than in most normal tissues. Targeted agents are designed to be selective in their effects by modulating the activity of proteins necessary and essential for oncogenesis and maintenance of cancer, particularly enzymes driving the uncontrolled growth, angiogenesis, invasiveness, and metastasis characteristic of malignant tumors. The increased differential activity usually results in fewer troubling side effects for cancer patients, particularly less nausea, vomiting, and death of cells in the bone marrow and gastrointestinal tract, and increased effectiveness against tumor cells.

A promising set of targets for therapeutic intervention in the treatment of cancer includes the members of the HER-kinase axis. They are frequently up-regulated in solid epithelial tumors of, by way of example, the prostate, lung and breast, and are also up-regulated in glioblastoma tumors. Epidermal growth factor receptor (EGFR) is a member of the HER-kinase axis and has been the target of choice for the development of several different cancer therapies. EGFR tyrosine kinase inhibitors (EGFR-TKIs) are among these therapies, since the reversible phosphorylation of tyrosine residues is required for activation of the EGFR pathway. In other words, EGFR-TKIs block a cell surface receptor responsible for triggering and/or maintaining the cell signaling pathway that induces tumor cell growth and division. Specifically, it is believed that these inhibitors interfere with the EGFR kinase domain.

Some time ago, genomic rearrangements in the anaplastic lymphoma kinase (ALK) receptor tyrosine kinase were identified in a subset of non-small cell lung carcinoma (NSCLC) patients. Soon after, crizotinib, a small molecule ATP-competitive ALK inhibitor was proven to be more effective than chemotherapy in ALK-positive NSCLC patients. Crizotinib and two other ATP-competitive ALK inhibitors, ceritinib and alectinib, are approved for use as a first-line therapy in these patients, where ALK rearrangement is currently diagnosed by immunohistochemistry and in situ hybridization. The clinical success of these three ALK inhibitors has led to the development of next-generation ALK inhibitors with even greater potency and selectivity. However, patients unfortunately inevitably develop resistance to ALK inhibitors leading to tumor relapse that commonly manifests in the form of brain metastasis.

Anaplastic lymphoma kinase (ALK) rearrangements define a distinct molecular subtype of non-small cell lung cancer. Recently, the therapeutic landscape for advanced ALK-positive NSCLC has been transformed by the development of increasingly potent and selective ALK inhibitors. Crizotinib was the first ALK inhibitor to enter clinical development. In randomized phase III trials, crizotinib produced significant improvements in objective response rates (ORRs) and progression-free survival (PFS) compared to cytotoxic chemotherapy, establishing crizotinib as a standard treatment for advanced ALK-positive NSCLC.

While most patients respond to crizotinib, patients ultimately relapse on therapy, generally within one to two years. Analysis of post-progression biopsy specimens has proven extremely valuable, facilitating a greater understanding of molecular mechanisms of crizotinib resistance. In general, such mechanisms have been classified as involving either on-target genetic alterations (e.g., ALK resistance mutations, ALK gene amplification) or off-target mechanisms of resistance (e.g., up-regulation of bypass signaling pathways, such as EGFR, KIT, IGF-1R, SRC, MEK/ERK and others. Typically, on-target resistance mechanisms have been found in approximately one-third of patients progressing on crizotinib.

Recently, several second-generation ALK inhibitors have demonstrated impressive activity in ALK-positive NSCLC.

Two of these agents, ceritinib and alectinib, have received approval by the U.S. Food and Drug Administration (FDA) for the treatment of crizotinib-refractory, ALK-rearranged NSCLC. A third agent, brigatinib, received breakthrough-therapy designation by the FDA and was recently approved. In preclinical models, second-generation ALK inhibitors overcome several crizotinib-resistant ALK mutations. Furthermore, in phase I-II studies, these agents have demonstrated high ORRs (48-71%) in crizotinib-resistant patients. Importantly, second-generation ALK inhibitors have also been active in patients without ALK resistance mutations or fusion gene amplification, suggesting that many cancers become resistant to crizotinib due to inadequate suppression of ALK. However, despite the efficacy of second-generation ALK inhibitors, patients almost invariably relapse.

While several new approaches aim to overcome the various mechanisms of resistance that develop in ALK-positive NSCLC including the knowledge-based alternate and successive use of different ALK inhibitors, as well as combined therapies targeting ALK plus alternative signaling pathways, however, new approaches to addressing resistance are needed.

SUMMARY OF INVENTION

An object of the present invention is a method of treating patients suffering from cancers driven by ALK mutations and ROS1 rearrangements comprising administering to a patient in need of such treatment a flexible and active regimen for combining a Anaplastic Lymphoma Kinase Inhibitors (ALK inhibitor) with active EGF Pathway Immunization (EGF PTI) for inhibition of the pathway activated by EGF-EGFR, wherein in this method the ALK inhibitor is administered according to a continuous regimen based on an average daily dose in the range of about 10 to 250 mg and the EGF PTI is co-administered according to a dosing regimen achieving a therapeutic effective amount repeated thrice, twice or once a week, once in two weeks, once in three weeks or at least once monthly.

A further object of the present invention is a method of treating a patient suffering from a non-small cell lung cancer (NSCLC) driven by ALK mutations and ROS1 rearrangements, wherein: the patient has a tumor expressing mutated forms of the EGFR, comprising administering to a patient in need of such treatment a flexible and active regimen for combining a and active immunization targeting EGF wherein in this method the ALK inhibitor is administered according to a continuous regimen based on an average daily dose in the range of about 10 to 250 mg and the active immunization, EGF PTI is co-administered according to a therapeutic effective amount repeated thrice, twice or once a week, once in two weeks, once in three weeks or at least once monthly, wherein the method results in preventing acquiring resistance to ALK inhibitor treatment.

Another object of the invention is a pharmaceutical kit; comprising a first compartment which comprises an effective amount of an anti EGF targeted antibodies and a second compartment which comprises an effective amount of an ALK inhibitor.

A further object of the invention is a pharmaceutical kit; comprising a first compartment which comprises an effective amount of a vaccine producing an immune response to EGF and a second compartment which comprises an effective amount of an ALK inhibitor. Another object of the invention is a pharmaceutical kit; comprising a first compartment which comprises an effective amount of a vaccine producing an immune response to EGFR and a second compartment which comprises an effective amount of an ALK inhibitor.

A further object of the invention is an ALK inhibitor for use in a method of treatment of a patient suffering from a cancer driven by ALK mutations and ROS1 rearrangements by co-administration with a vaccine producing an immune response to EGF, wherein the ALK inhibitor is administered according to a continuous regimen based on an average daily dose in the range of about 10 to 250 mg and the vaccine producing an immune response to EGF is co-administered according to a therapeutic effective amount repeated thrice, twice or once a week, once in two weeks, once in three weeks or at least once monthly to a patient in need of such treatment.

A further object of the invention is the use of an ALK inhibitor for preparation of a pharmaceutical kit for treatment of patients suffering from cancers driven by ALK mutations and ROS1 rearrangements, comprising a first compartment which comprises an effective amount of a vaccine producing an immune response to EGF and a second compartment which comprises an effective amount of ALK inhibitor to be administered according to a continuous regimen based on an average daily dose in the range of about 10 to 250 mg and the vaccine is administered prior to initiating ALK inhibitor therapy according to a dosing regimen ranging from an average weekly dose a therapeutic effective amount repeated thrice, twice or once a week, once in two weeks, once in three weeks or at least once monthly to a patient in need of such treatment.

BRIEF DESCRIPTION OF THE DRAWINGS

The present disclosure is further described in the detailed description which follows, in reference to the noted plurality of drawings by way of non-limiting examples of embodiments of the present disclosure, in which like reference numerals represent similar parts throughout the several views of the drawings, and wherein:

The disclosure will be more fully understood by reference to the detailed description, in conjunction with the following figures, wherein:

FIG. 1 illustrates NSCLC cell lines which account for approximately 75% of the ALK rearrangements found in patients. H3122 carries the EML4-ALK v1 fusion and H2228 carries the EML4-ALK v3 fusion;

FIGS. 2A-B show the effect on cell viability of Brigatinib and Alectinib in the presence and absence of EGF in the H3122 cell line;

FIGS. 7A-B show the effect on cell viability of BVN22E antibodies in combination with Brigantinib and Alectinib in H3122 and H2228 cells;

FIG. 8 shows the effect on pEGFR (TYR 1068), pSTAT3 (TYR 705), pAKT (SER 473), and ERK1/2 (THR 202/TYR 204) in response to 2 hour incubation with BVN22E antibodies in H3122 cells;

FIG. 10 shows the effect on pEGFR (TYR 1068), pSTAT3 (TYR 705), pAKT (SER 473), and ERK1/2 (THR 202/TYR 204) in response to 2 hour incubation with Crizotinib in H3122 cells;

FIGS. 11A-B show the effect on cell viability of Brigatininb and Alectinib in the presence and absence of EGF in the H2228 cell line;

FIGS. 16A-B show the effect on cell viability of BVN22E antibodies in combination with Brigantinib and Alectinib in H2228 cells;

FIG. 39 illustrates the KRAS mutations of the cell lines used in the instant disclosure. A549 cells contain a G12S KRAS mutation, H23 cells contain a G12C KRAS mutation, DLD1 cells contain a G13D KRAS mutation, and LS174T cells contain a G12C KRAS mutation;

DETAILS OF THE INVENTION

Figure 3:
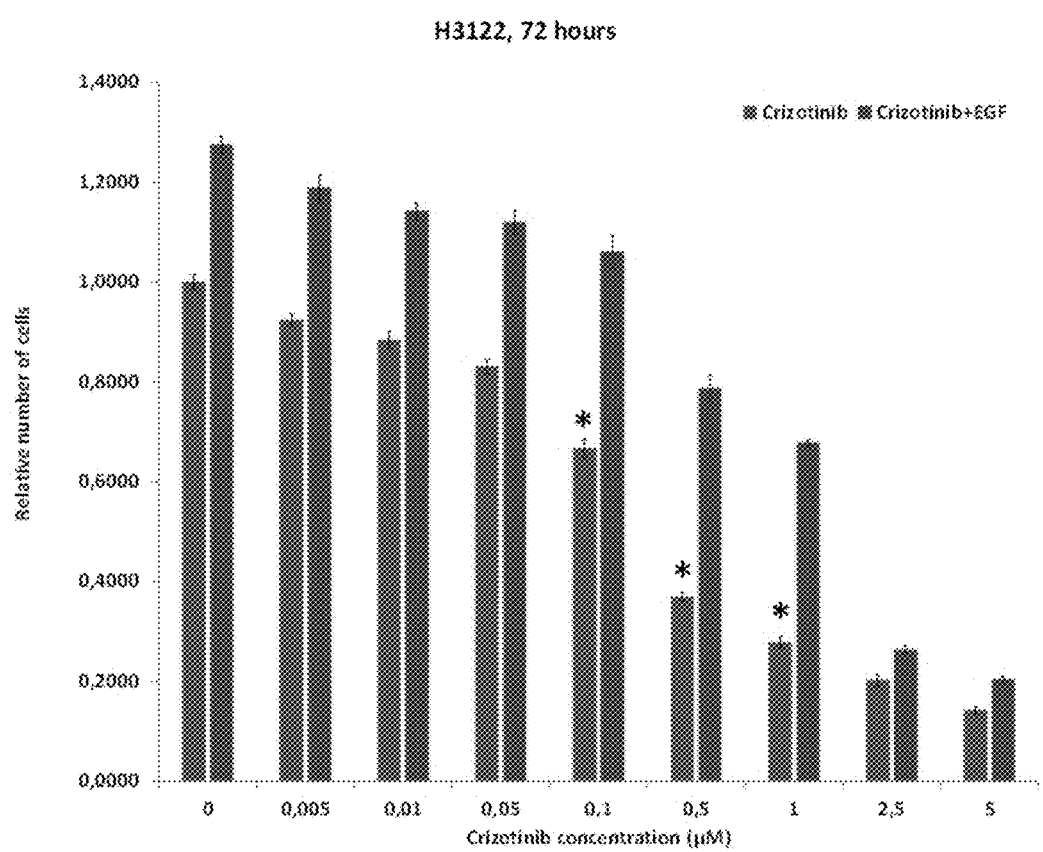
FIG. 3 shows the effect on cell viability of Crizotinib in the presence and absence of EGF in the H3122 cell line after 72 hour incubation.

In 2007, an EML4-ALK (echinoderm microtubule-associated protein 4) fusion oncogene in a patient with non-small-cell lung cancer (NSLC) was first identified. That fusion is the result of an inversion in the short arm of chromosome 2, juxtaposing the N terminal end of the EML4 gene's promoter and the kinase domain of the anaplastic lymphoma kinase (ALK) gene. After formation of the EML4-ALK fusion, the EML4 fusion partner mediates ligand-independent activation of ALK and constitutive kinase activity, leading to proliferation and survival of the cancer cells responsible for 3%-7% of NSLC.

ALK inhibitors target variations of (ALK) that lead to tumor growth, such as the EML4-ALK translocations. Crizotinib was the first ALK inhibitor to be approved by the FDA, in August 2011, and it is now the standard of care for patients with metastatic ALK-positive NSCLC. Unfortunately, most patients whose non-small cell lung carcinoma (NSCLC) initially responded to crizotinib become resistant and regress to disease progression within a year of starting the therapy. Crizotinib resistance appears to emerge because NSCLC cells acquire additional ALK mutations. The next generation of ALK inhibitors to be approved by the FDA, Ceritinib (Zykadia) and Alectinib (Alecensa), can inhibit most of the clinically observed ALK mutations that drive resistance to crizotinib; these two therapeutics are currently approved for treating patients with metastatic ALK-positive NSCLC that has either progressed after treatment with Crizotinib or has failed to respond to Crizotinib in the first place.

Ceritinib, Alectinib, Brigatinib, and Lorlatinib are next generation inhibitors that have all been approved by the FDA for ALK-positive NSCLC. ALK inhibitors include Ceritinib (LDK378), Alectinib (RO5424802/CH5424802), Brigatinib (AP26113), ASP3026, Belizatinib (TSR-011), Lorlatinib (PF-06463922), Entrectinib (RXDX-101), Ensartinib (X-396), and CEP-37440.

Crizotinib is a potent inhibitor of c-Met and ALK with an IC50 of 11 nM and 24 nM in cell-based assays, respectively. Ceritinib (LDK378) is a potent and specific ALK inhibitor with an IC50 of 0.2 nM. Alectinib (CH5424802; R05424802; AF802) is a potent, selective, and orally available ALK inhibitor with an IC50 of 1.9 nM. Brigatinib is a highly potent and selective ALK inhibitor, with an IC50 of 0.6 nM. ASP3026 is a novel and selective inhibitor for ALK (anaplastic lymphoma kinase) with IC50 of 3.5 nM. Belizatinib is an oral, dual, potent inhibitor of ALK and TRKA, TRKB, and TRKC, with IC50 of 0.7 nM for wild-type recombinant ALK kinase. Lorlatinib (PF-06463922) is a potent, dual ALK/ROS1 inhibitor, with K is of 0.02 nM, 0.07 nM, and 0.7 nM for ROS1, wild type ALK, and ALK-L1196M, respectively. Entrectinib is a potent and orally available Trk, ROS1, and ALK inhibitor; inhibits TrkA, TrkB, TrkC, ROS1 and ALK with IC50 values of 1, 3, 5, 12 and 7 nM, respectively. Ensartinib (X-396) is a potent and dual ALK/MET inhibitor with IC50s of <0.4 nM and 0.74 nM, respectively. CEP-37440 is a novel potent and selective dual FAK/ALK inhibitor with IC50 s of 2.3 nM (FAK) and 120 nM (ALK cellular IC50 in 75% human plasma). IC50 value: 2.3 nM (FAK); 120 nM (ALK cellular IC50 in 75% human plasma) (WO 2013134353, A1 20130912).

Crizotninib

Two subsequent randomized phase III studies compared crizotinib with standard chemotherapy, leading to full approval for crizotinib and, until recently, positioning it as the "gold standard" for the first-line treatment of ALK-positive NSLC. Consistent with the phase II study data, crizotinib demonstrated impressive results in comparison with chemotherapy, showing improvements in orr (65% vs. 20%) and pfs [hazard ratio (hr): 0.49; 7.7 months vs. 3 months]. Then, crizotinib was compared with platinum-pemetrexed chemotherapy in ALK-positive treatment-naïve patients. Once again, compared with chemotherapy, crizotinib was associated with improvements in orr (74% vs. 45%), mpfs (hr: 0.45; 10.9 months vs. 7 months), and importantly, quality of life. No differences in overall survival (s) were seen. (Rothenstein et al. Current Oncology, 2018)

Ceritinib

Ceritinib was the first next-generation inhibitor to show benefit in treating crizotinib-resistant ALK-positive NSLC. Compared with crizotinib, ceritinib has 20 times the potency for inhibiting alk, and cell-line studies of biopsies from patients who had developed crizotinib resistance indicated that ceritinib is a potent inhibitor of some of the resistance mutations found.

Alectinib

Alectinib is another highly selective ALK inhibitor that has activity against crizotinib-resistant ALK mutations. One unique feature of alectinib is that it is not a substrate for P-glycoprotein, which is implicated as a mechanism of CNS resistance in patients taking crizotinib. Alectinib is now established as the new standard first-line treatment for patients with advanced ALK-positive NSCLC. While most responses to first-line alectinib are durable, essentially all patients will develop resistance leading to clinical relapse. Two other second-generation ALK inhibitors ceritinib and brigatinib—have only been tested in the crizotinib-naive and/or crizotinib-resistant setting.

The third-generation ALK/ROS1 inhibitor lorlatinib has completed phase I and II testing and has been tested across numerous settings, including in patients who are ALK TKI-naive, crizotinib-resistant, or resistant to one or more second-generation ALK TKIs. Lorlatinib has demonstrated antitumor activity in all of these settings, including in patients who have failed a second-generation ALK inhibitor such as alectinib. Lorlatinib is highly CNS-penetrant and has demonstrated potent intracranial activity, even in patients who have failed a brain-penetrable TKI such as alectinib.

Based on the efficacy and safety seen in the phase I/II study, lorlatinib received FDA breakthrough therapy designation last year and is anticipated to gain accelerated approval this year for ALK-positive patients previously treated with 1 or more ALK inhibitors. Thus, the paradigm of sequential therapy with crizotinib followed by a second-generation ALK inhibitor is now being replaced by a new paradigm of alectinib followed by lorlatinib.

Embodiments of the technology described herein are based, at least in part, on the discovery that anti EGF antibodies at physiological concentrations, have inhibitory effects on phosphorylation of EGFR, Akt and ERK1/2 are at least as significant as the effect of ALK inhibitors on these signaling molecules. It was further discovered that that combination treatment of the anti EGF antibodies and ALK inhibitors shows additional effect for pEGFR, pAkt, pERK1/2 and pSTAT-3 inhibition. In some embodiments, such antibodies or antigen-binding fragments thereof can be used in the methods of treating NSLC. It is contemplated within the scope of the disclosure that the anti EGF antibodies can be actively produced in vivo by the administration of a vaccine producing an immune response to EGF. It is further contemplated within the scope of the disclosure that passive monoclonal anti EFG antibodies can be administered.

ALK positive (anaplastic lymphoma kinase positive, or ALK+) lung cancer occurs in 1 out of 25 non-small-cell lung cancer patients (NSCLC—the most common type of lung cancer). Younger patients—usually 55 and under—who have never smoked are most likely to be diagnosed as being ALK+.

Anaplastic lymphoma kinase inhibitors (ALK inhibitors) work by interfering with (or inhibiting) the ALK signaling pathway. In order to pass a signal from one kinase (the key) to another kinase (the lock) the two kinases need to temporarily fit together. A kinase inhibitor works by temporarily blocking one kinase, so that other kinase cannot receive the first kinase. Thus a certain concentration of kinase inhibitors has to be reached in order to block the signal from being passed sufficiently often (probably over 90%) in order to stop the kinase from regulating the expression of certain genes.

Most of the drugs that are being developed to combat ALK based tumors are designed to interfere with (or inhibit) ALK's signaling pathway (either by stopping ALK from passing a signal or stopping another kinase in the pathway from passing its signal). So for example one ALK inhibitor is designed to inhibit the AKT kinase which is downstream from ALK. Thus it is being tested to see if it is effective against ALK based tumors along with other types of tumors.

Like other kinase inhibitors, resistance is a problem. While limited data is available on mechanisms of resistance to next-generation ALK inhibitors; almost all the data are in patients who received these agents following treatment with crizotinib. As is true with other TKIs, target alteration, activation of alternative signaling pathways, and phenotypic changes in the tumor have been observed in tumors resistant to next-generation ALK inhibitors. It has been shown that target alteration with ALK is much more commonly observed in tumors following next-generation ALK inhibitors than in tumors of patients treated with crizotinib. The most common mutation observed was G1202R, a mutation in the solvent-exposed region of ALK, resulting in steric hindrance to most ALK inhibitors. It is unclear if the same mechanisms of resistance or in the same proportions will be observed in tumors of patients treated with next-generation ALK inhibitor as the first ALK inhibitor.

ALK-positive NSCLC shows variable PFS as cancers eventually develop resistance to first-generation ALK inhibitor crizotinib within 1-2 years. Like EGFR, there are resistance mutations within the TK domain of ALK, most commonly L1196M. This mutation causes steric hindrance at the binding site resulting in decreased potency of response to crizotinib. However, unlike in EGFR-TKI resistance, there are multiple kinase domain mutations (G1269A, G1202R, S1206Y, F1174C/L, D1203N) as well as mutations away from the binding site (threonine insertion at 1151, C1156Y, L1152R) that have been identified in the setting of ALK-TKI resistance. In vitro studies indicate that the different resistance mutations confer different levels of resistance to structurally different TKIs, highlighting the need to identify the secondary resistance mutation through a repeat cancer sample at the time of acquired resistance and a more detailed sequencing method rather than FISH analysis [69, 70]. In addition, there are other cases of ALK-TKI resistance that show only amplification of the fusion product by FISH testing, some which show one of the identified resistance mutations and others that show only amplification.

Crizotinib is an oral MET/ALK inhibitor used as first-line therapy in the treatment of advanced NSCLC harboring ALK rearrangements. In addition, newer second-generation ALK inhibitors with increased potency and selectivity against ALK are under evaluation in clinical trials. Like crizotinib, these agents are ATP-competitive inhibitors of the ALK tyrosine kinase although they are structurally distinct from crizotinib. Ceritinib is a second-generation inhibitor that has shown activity in patients with ALK-positive lung cancer, including individuals with acquired resistance to crizotinib. Ceritinib received FDA approval for use in patients with advanced ALK-rearranged NSCLC previously treated with crizotinib. However, responses to ALK inhibitors are short-lived, with resistance commonly occurring within a year.

Since the introduction of crizotinib in the treatment of ALK-driven NSCLC, gene amplification or secondary mutations in EML4-ALK have been identified in approximately one-third of tumors with acquired resistance to crizotinib. Secondary mutations have been shown in vitro to drive resistance to crizotinib, but not all confer resistance to the structurally distinct second-generation ALK inhibitors. In addition, activation of EGFR, KIT, and IGF-1R have been separately identified in a subset of tumors with resistance to crizotinib. Resistance to second-generation ALK inhibitors is less characterized due to the recent introduction of these agents to the clinic, although secondary mutations in EML4-ALK have been identified in a subset of tumors with acquired ceritinib resistance.

Mutations in EGFR correlate with impaired response to immune checkpoint inhibitors and the development of novel immunotherapeutic approaches for EGFR mutant NSCLC is of particular interest. Immunization against epidermal growth factor (EGF) has shown efficacy in a phase III trial including unselected NSCLC patients, but little was known about the mechanisms involved in the effects of the anti-EGF antibodies generated by vaccination (anti-EGF VacAbs) or their activity in tumor cells with EGFR mutations.

Vaccination against EGF constitutes a novel strategy that, contrary to programmed death 1 blockade, is not intended at reversing tumor-induced immunosuppression by activating the T cells. Instead, it aims to stimulate B cells to produce neutralizing antibodies that sequester circulating EGF, thus preventing its binding to EGFR. Vaccination against EGF, also referred to EGF-pathway targeted immunization, is well tolerated, generates few cases of severe adverse effects, and has shown promising results in two trials enrolling unselected advanced NSCLC patients (11, 12, and 21). However, little was known about the molecular and cellular mechanisms involved in the effects of anti-EGF antibodies besides their capability to block ligand binding and Phosphorylation of EGFR, or about their differential activity in tumors with EGFR mutations or other genetic alterations (22).

The instant disclosure shows that anti-EGF VacAbs raised in rabbits suppressed the effects of EGF on cell proliferation, cell cycle, and signal transduction pathways in EGFR-mut NSCLC cell lines, particularly in those derived from untreated patients. The concentrations of EGF used in the experiments (10 ng/mL) were close to those reported in human studies, which have a median around 1 ng/mL and show a significant inter-individual variability (11,23). Remarkably, the anti-EGF VacAbs were also found to consistently reduce the levels of pErk1/2 in absence of exogenous EGF not only in PC9 cells, but also in PC9-GR4 cells, where the growth factor did not show significant effects. One of the possible explanations for this observation could be the existence of receptor/ligand feedback loops in the cell lines used. Sera from patients immunized with an anti-EGF vaccine were also shown to efficiently block the activation of pErk1/2 by EGF. Control sera from non-immunized patients had little effect on Erk1/2 but strongly activated Akt, indicating that the blood of healthy individuals contains growth factors that specifically trigger pAkt in EGFR-mut cells. In contrast, the sera from the four immunized patients analyzed were less active in inducing Akt phosphorylation. Significant differences were observed in the potency of the sera from vaccinated individuals to block Erk1/2 phosphorylation and, to a lesser extent, to activate Akt. Being a new therapeutic approach with only a phase III trial completed, the availability of samples from patients vaccinated against EGF was limited, and it was not possible to correlate it with clinical outcomes.

Previously it has been found that EGF significantly reduced the antiproliferative effects of TKIs such as gefitinib, erlotinib, afati-nib, and osimertinib in several EGFR-mut NSCLC cells, both sensitive and resistant to EGFR TKIs. This finding correlated with the results of Western blotting experiments where the levels of pErk1/2 in cells treated with EGF TKIs were significantly higher if EGF was present.

It is likely that EGFR-mut patients with high EGF levels might have worse outcomes to EGFR TKIs. Increased serum levels of two EGFR ligands, transforming growth factor alpha and amphiregulin, were reported to correlate with worse responses to EGFR TKIs in unselected NSCLC patients. Regarding EGF, in the only study published to date, for 11 EGFR-mut and 21 EGFR-wt NSCLC patients treated with erlotinib, EGF in the serum correlated with shorter progression-free survival. It has been found that the combination of gefitinib, erlotinib, afatinib, and osimertinib with anti-EGF VacAbs showed a stronger antiproliferative effect than the EGFR TKIs alone in the EGFR-mut cell lines tested, a finding that correlated with a consistent decrease in pErk1/2 (FIG. 78, compare lanes TKI+EGF with TKI+Ab+

EGF). The combination was also superior in blocking the anti-apoptotic and G2/M stimulating effects of EGF.

The anti-EGFR monoclonal antibody cetuximab has also been tested in EGFR-mut cell line models. Similarly to anti-EGF VacAbs, cetuximab blocks ligand binding in vitro and has been shown to prevent ligand-induced EGFR, Erk1/2, and Akt phosphorylation in PC9 and H1975 cells. However, it showed a relatively little effect on EGFR downstream signaling in other EGFR-mut lines such as H3255 or DFCILU-011.29 Regarding receptor down-regulation, there seemed to be significant differences between the two antibodies. Cetuximab has been shown to markedly decrease the levels of total EGFR after 1 to 2 hours of incubation in EGFR-mut cells such as PC9, H1975 or H3255, whereas anti-EGF VacAbs did not induce any significant down-regulation of the receptor after 24 hours of incubation. Finally, although cetuximab was reported to amplify the induction of apoptosis and tumor regression in EGFR-wt, head and neck cancer cell lines, and subcutaneous tumors, it failed to enhance the effects of gefitinib in PC9 xenografts.

In contrast, it has been previously found that anti-EGF VacAbs potentiated the antiproliferative activity of EGFR TKIs in PC9 and the rest of EGFR-mut cell lines tested. This potentiating effect reached statistical significance in all cases, with the only exception being PC9-GR4 cells. The fact that the anti-EGF VacAbs target the ligand instead of the receptor and do not induce EGFR down-regulation might offer a possible explanation for the differences found between the effects of cetuximab and anti-EGF antibodies.

It has also been previously found that the addition of the anti-EGF VacAbs significantly delayed the appearance of clones resistant to gefitinib and afatinib in the PC9 cell line. The addition of anti-EGF VacAbs consistently suppressed this TKI-induced STAT3 activation. In contrast, pSTAT3 has been shown to be elevated in head and neck human tumors progressing to cetuximab, suggesting that STAT3 activation is involved in resistance to this drug.

In summary, anti-EGF VacAbs suppressed the effects of EGF and significantly enhanced the antitumor activity of EGFR TKIs in EGFR-mutated NSCLC cell lines. They also blocked STAT3 activation, reduced AXL expression, and delayed the acquisition of resistance. It is therefore thought that ALK inhibitors may also benefit from anti-EGF VacAbs.

ALK is thought to play a significant role in the development and function of the nervous system, where it controls the basic mechanisms of cell proliferation, survival, and differentiation in response to extracellular stimuli. The most prevalent genomic ALK aberrations in human cancer are chromosomal rearrangements, resulting in fusion genes. ALK fusions arise from fusion of the 3' half of ALK, derived from Chromosome 2 that retains its kinase catalytic domain, and the 5' portion of a different gene that provides its promoter. Multiple different 5' partners have been identified. Wild-type ALK is normally activated through binding of ligands to its extracellular domain, resulting in dimerization and autophosphorylation of the kinase domain. Structural studies show that fusion with multiple 5' partners helps bypass this requirement and increase oncogenic potential of ALK, as evidenced by NPM1-ALK and EML4-ALK) in non-small-cell lung cancer (NSCLC). Increased copy number and the presence of activating point mutations that result in kinase activation are also linked to oncogenic activity of ALK. These genetic alterations are found in multiple malignancies, including, but not limited to, lung cancer, neuro-blastoma rhabdomyosarcoma, renal cell carcinoma, inflammatory myofibroblastic tumor (IMT), and inflammatory breast cancer.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more.

As used herein, the terms "proteins" and "polypeptides" are used interchangeably herein to designate a series of amino acid residues connected to the other by peptide bonds between the alpha-amino and carboxy groups of adjacent residues. The terms "protein", and "polypeptide", which are used interchangeably herein, refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof.

Thus, exemplary polypeptides or proteins include gene products, naturally occurring proteins, homologs, orthologs, paralogs, fragments and other equivalents, variants, fragments, and analogs of the foregoing.

As used herein the term, "Antibody" includes any immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab').sub.2, and Fv fragments), single chain Fv (scFv) mutants, multi-specific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as cytotoxics, toxins, radioisotopes, etc. Antibodies can be administered by actively producing them in vivo or passive administering monoclonal antibodies.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called α, δ, ε, γ, and μ, and respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population comprise essentially identical amino acid sequence except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "subject", as used herein, refers to any organism that is capable of developing a bacterial infection. Such organisms include, but are not limited to, human, dog, cat, horse, cow, sheep, goat, mouse, rat, guinea pig, monkey, avian, reptiles, etc.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

By "BVN22E nucleic acid molecule" is meant a polynucleotide encoding a BVN22E polypeptide. An exemplary BVN22E nucleic acid molecule is reproduced below (SEQ ID NO:1):

>BVN22E
AATACCGAAAACGATTGCCCTCTGTCTCATGAAGCGTATTGTCTGCACGA

CGGCGTGTGTATGTACATTGAAGCCCTGGACAAATATGCATGTAACTGTG

TCGTGGGCTACGTGGGGGAGCGATGTCAGTTTCGAGACCTGCGTTGGTGG

GATGCGCGCGGCTCGAGCGGTAATACCGAAAACGATTGCCCTCTGTCTCA

TGAAGCGTATTGTCTGCACGACGGCGTGTGTATGTACATTGAAGCCCTGG

ACAAATATGCATGTAACTGTGTCGTGGGCTACGTGGGGGAGCGATGTCAG

TTTCGAGACCTGCGTTGGTGGGATGCGCGCGGCGGGTCTGGAGGTACTAG

TGGCGGCGGTGGAGGGTCGGGTACCCCGCAGAACATCACCGACCTGTGCG

CCGAGTACCACAACACCCAGATCCACACCCTGAACGACAAGATCTTCTCG

TACACCGAGAGCCTGGCCGATAAGCGTGAAATGGCCATCATCACCTTCAA

GAACGGTGCGACCTTCCAGGTGGAGGTCCCGGGTAGCCAGCACATCGATT

CACAGAAGAAGGCCATCGAGCGTATGAAGGACACCCTGCGTATCGCCTAC

CTGACCGAAGCCAAGGTGGAAAAGCTGTGCGTCTGGAACAACAAGACGCC

GCACGCCATCGCCGCCATCAGCATGGCCAAT

By "BVN22E polypeptide" is meant a polypeptide or fragment thereof having at least about 85%, 90%, 91%, 92%, 93%, 94%, 95%, 96%, 97%, 98%, or 99% amino acid identity (excluding the following amino acid changes: T2S, E3D, N4S, D5E, E11D, A12G, V38I, F44Y, R48K, D51E, and A52L) to the amino acid sequence below (SEQ ID NO:2):

>BVN22E
NTENDCPLSHEAYCLHDGVCMYIEALDKYACNCVVGYVGERCQFRDLRWW

DARGSSGNTENDCPLSHEAYCLHDGVCMYIEALDKYACNCVVGYVGERCQ

FRDLRWWDARGGSGGTSGGGGGSGTPQNITDLCAEYHNTQIHTLNDKIFS

YTESLADKREMAIITFKNGATFQVEVPGSQHIDSQKKAIERMKDTLRIAY

LTEAKVEKLCVWNNKTPHAIAAISMAN

A "pharmaceutical excipient" shall mean those commonly utilized within the pharmaceutical art and in particular those found "Handbook of excipients", (Raymond C. Rowe, Paul J. Sheskey, Paul J. Weller-4$^{th}$ Edition, 2003), the contents of which are incorporated in their entirety.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega11 (see, e.g., Agnew, Chem Intl. Ed. Engl., 33: 183-186 (1994)); dynemicin, including dynemicin A; an espmeramicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromefthylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

"Patient response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of cell proliferation, invasion or metastasis, which may, but does not have to, result in the regression or ablation of a disease lesion; (7) relief, to some extent, of one or more symptoms associated with the disorder; (8) increase in the length of disease-free presentation following treatment; and/or (9) decreased mortality at a given point of time following treatment.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

ALK Inhibitor Agents

Therapeutic implications for ALK gene alterations are predominantly associated with ALK gene fusions, which predict tumor response to ALK inhibitors. Crizotinib, ceritinib, and recently alectinib are FDA approved for the treatment of patients with metastatic NSCLC whose tumors are positive for ALK fusions. Early phase 1 studies showed crizotinib yielded sustained responses in ALK-fusion-positive metastatic NSCLC patients. Two phase 3 studies, which led to FDA approval of crizotinib, further confirmed that crizotinib was superior to standard first-line pemetrexed+cisplatin chemotherapy in patients with previously untreated advanced ALK-rearranged NSCLC.

Although crizotinib has shown excellent activity in patients with NSCLC who are ALK-fusion-positive, durable responses remain uncommon, with a median PFS of 13 months, because of the development of resistance that leads to disease progression. Although the mechanism of resistance is still being delineated, acquired secondary mutations in the ALK kinase domain (F1174L, F1174C, L1196M, 11171T, G1202R, S1206Y, G1269S, and G1269A) or ALK gene amplification are known to be associated with resistance. Resistance can also be mediated by activation of alternative ALK-independent survival pathways that hamper the effectiveness of crizotinib, including the epidermal growth factor pathway, insulin-like growth factor pathway, RAS/SRC signaling, and AKT/mTOR signaling, among others.

ALK Inhibitors brigatinib and lorlatinib inhibit several known resistant mutations, and lorlatinib showed effective inhibition against the G1202R mutation. These results suggest that understanding the resistance mechanism and selecting the appropriate tyrosine kinase inhibitor (TKI) may be required to optimize response to therapy.

In addition to targeting ALK directly, there are pharmacological strategies that allow for its indirect targeting. Specifically, there has been some success with inhibiting ALK indirectly by targeting heat-shock proteins, namely HSP90, in lung cancer. Inhibition of HSP90, a chaperone protein that stabilizes a wide variety of proteins, including ALK, has shown some preclinical efficacy in crizotinib-resistant ALK fusions (EML4-ALK and NPM1-ALK), including secondary resistant mutants in lung cancer models.

ALK rearranged tumors represent a specific subset of tumors that can be effectively targeted with currently available ALK inhibitors. Hence testing for ALK alterations in tumors known to have this molecular aberration is now an obligatory part of the diagnosis. FISH, next-generation sequencing (NGS) of tumor tissue, and sequencing of circulating tumor cells offer alternative and often complementary ways of detecting tumors with ALK alterations. The almost inevitable emergence of resistance during TKI therapy requires re-biopsy of the tumor at relapse to identify resistance mechanisms that could be targeted with newer ALK inhibitors and other novel therapeutic strategies.

Crizotinib has an aminopyridine structure, and functions as a protein kinase inhibitor by competitive binding within the ATP-binding pocket of target kinases. About 4% of patients with non-small cell lung carcinoma have a chromosomal rearrangement that generates a fusion gene between EML4 ('echinoderm microtubule-associated protein-like 4') and ALK ('anaplastic lymphoma kinase'), which results in constitutive kinase activity that contributes to carcinogenesis and seems to drive the malignant phenotype. The kinase activity of the fusion protein is inhibited by crizotinib. Patients with this gene fusion are typically younger non-smokers who do not have mutations in either the epidermal growth factor receptor gene (EGFR) or in the K-Ras gene. ALK mutations are thought to be important in driving the malignant phenotype in about 15% of cases of neuroblastoma, a rare form of peripheral nervous system cancer that occurs almost exclusively in very young children. Crizotinib inhibits the c-Met/Hepatocyte growth factor receptor (HGFR) tyrosine kinase, which is involved in the oncogenesis of a number of other histological forms of malignant neoplasms.

Alectinib is a tyrosine kinase receptor inhibitor and antineoplastic agent used in the therapy of selected forms of advanced non-small cell lung cancer. Alectinib is associated with a moderate rate of transient elevations in serum aminotransferase levels during therapy and with rare instances of clinically apparent acute liver injury.

Alectinib is an orally available inhibitor of the receptor tyrosine kinase anaplastic lymphoma kinase (ALK) with antineoplastic activity. Upon administration, alectinib binds to and inhibits ALK kinase, ALK fusion proteins as well as the gatekeeper mutation ALKL1196M known as one of the mechanisms of acquired resistance to small-molecule kinase inhibitors. The inhibition leads to disruption of ALK-mediated signaling and eventually inhibits tumor cell growth in ALK-overexpressing tumor cells. ALK belongs to the insulin receptor superfamily and plays an important role in nervous system development. ALK dysregulation and gene rearrangements are associated with a series of tumors.

Alectinib is an organic heterotetracyclic compound that is 6,6-dimethyl-5,6-dihydro-11H-benzo[b]carbazol-11-one carrying additional cyano, 4-(morpholin-4-yl)piperidin-1-yl and ethyl substituents at positions 3, 8 and 9 respectively. Used (as the hydrochloride salt) for the treatment of patients with anaplastic lymphoma kinase-positive, metastatic non-small cell lung cancer. It has a role as an EC 2.7.10.1 (receptor protein-tyrosine kinase) inhibitor and an antineoplastic agent. It is an organic heterotetracyclic compound, a member of morpholines, a member of piperidines, a nitrile and an aromatic ketone. It is a conjugate base of an alectinib (1+).

Brigatinib is a next-generation ALK inhibitor that targets a broad range of ALK mutations and ROS1 rearrangements. Currently It is also the only ALK inhibitor with activity in cell lines with mutations in the gene encoding epidermal growth factor receptor (EGFR). In the ALK in Lung Cancer Trial of AP26113 (ALTA) involving 222 patients with disease that was refractory to crizotinib, brigatinib administered at the recommended dosing regimen of 180 mg once daily (with a 7-day lead-in period at 90 mg in 110 patients) was associated with high systemic and CNS response rates and a median progression-free survival of 16.7 months. The same regimen was associated with similar progression-free survival (16.3 months) among patients who had received crizotinib in the phase 1-2 trial. These median rates of progression-free survival are higher than those associated with other next-generation ALK inhibitors (including alectinib, ceritinib, ensartinib, and lorlatinib) among such patients.

Signal transducer and activator of transcription 3 (STAT3) is an oncogenic transcription factor that is active in many human cancers and regulates the transcription of several genes that are involved in cell cycle progression, antiapoptosis, cell survival, and angiogenesis.

STAT3 can be activated by EGFR, JAK2, and other tyrosine kinases whose activation can be mediated by EGF, leukemia inhibitory factor (LIF), and other cytokines. Therefore, STAT3 is a convergent point of many signaling pathways and has a major role in oncogenesis and tumor metastasis. It is thought that STAT3 is activated by various forms of mutant EGFR and may contribute to the oncogenic effects of these mutants in fibroblasts and human lung cancer cells.

Following activation by either ligand binding or mutation, EGFR initiates a cascade of signal transduction pathways that alter the biology of the cell through transcriptional and post-translational mechanisms. The signaling pathways that mediate these changes include the Ras-Raf-mitogen-activated protein (MAP) kinase (MAPK), phosphoinositide 3-kinase-AKT, and signal transducers and activators of transcription (STAT) 3 and STAT5 signal transduction pathways. The STAT families of transcription factors are activated by phosphorylation on a conserved tyrosine residue, leading to dimerization, nuclear translocation, and DNA binding. STAT1, STAT3, and STAT5 are also phosphorylated on a serine residue in their COOH terminus; this phosphorylation it is thought is dispensable for dimerization, nuclear translocation, and DNA binding, but is required for maximal transcriptional activity of some genes.

Several non-small-cell lung cancer cell lines contain constitutively active STAT3. It has been recently shown that STAT3 is activated by several of these EGFR mutants in a genetically defined system. It is not known which of the signal transduction pathways downstream of mutant EGFR are required to mediate its oncogenic properties, however, given the role of STAT3 in a wide range of human malignancies, and the fact that it is activated by EGF in various cell types, it is believed that STAT3 is necessary for the oncogenic effects of somatic mutant EGFRs. It has been reported that STAT3 is activated in fibroblasts expressing mutant EGFRs, as well as in two NSCLC lines with naturally occurring EGFR mutations, and that this activation is required for the transformation and survival of these cells.

The activation of STAT3 often involves a ligand-receptor interaction. STAT3 can be activated by many various cytokines, including interferons, EGF, G-CSF, and interleukin (IL-6) family cytokines. Binding of cytokines to their cognate receptors leads to JAKs phosphorylation, STAT3 dimerization, nuclear translocation, DNA binding, and gene activation (12, 13). In addition, STAT3 phosphorylation can also be induced by cytoplasmic tyrosine kinase, such as Src family kinase (14). It has been reported that elevated EGFR activity and STAT3 activation is positive correlated in many primary tumor specimens and tumor-derived cell lines, including NSCLC, breast cancer, and head and neck carcinomas.

Increased STAT3 activity is observed in lung adenocarcinomas and cell lines expressing mutant EGFRs. Without being bound to any particular theory, STAT3, it is believed, is required by mutant EGFRs and is necessary for its downstream phenotypic effects. Inhibiting STAT3 function in fibroblasts abrogates transformation by mutant EGFR. Unfortunately, targeted therapies, such as TKIs and ALK inhibitors cannot completely abrogate STAT3 activity in NSCLC cell lines.

Previous studies suggest mutant EGFR induces activation of gp130/JAK/STAT3 pathway by means of IL-6 up-regulation. Tumor expression of IL-6 and IL-6 receptor components gp80 and gp130 had been found in NSCLC specimens (20). It has also been observed that increased levels of pro-inflammation cytokines such as IL-6 and IL-8 are also associated with NSCLC tumorigenesis and prognosis. These indicate that IL-6 and its downstream pathway are potential to be the target for patient with NSCLC harboring EGFR mutation. However, the mechanism about IL-6 induction by oncogenic EGFR mutations in NSCLC remains unclear; however, it is thought that NF-kB and STAT3 signaling are responsible for regulating IL-6 autocrine in lung cancer.

According to one aspect of the invention anti EGF antibodies are used for treating patients suffering from cancers driven by deregulated Human Epidermal Growth Factor Receptor expressing the ELM4-ALK fusion gene by administering to a patient in need of such treatment a flexible and active regimen for combining an Anaplastic Lymphoma Kinase Inhibitors (ALK Inhibitors) and anti-EGF antibodies according to the invention for inhibition of the pathway activated by EGF-EGFR binding (mAb), wherein the ALK inhibitor is administered according to a continuous regimen based on an average daily dose in the range of about 10 to 250 mg and the EGF TPI according to the invention is co-administered according to a dosing regimen achieving a therapeutic effective amount repeated thrice, twice or once a week, once in two weeks, once in three weeks or at least once monthly.

According to a further aspect of the invention anti EGF antibodies generated by vaccination of patients suffering from cancers driven by deregulated Human Epidermal Growth Factor Receptor expressing the ELM4-ALK fusion gene by administering to a patient in need of such treatment a flexible and active regimen for combining ALK inhibitor and a vaccine producing an immune response to EGF, wherein the ALK inhibitor is administered according to a continuous regimen based on an average daily dose in the range of about 10 to 250 mg and the vaccine according to the invention is co-administered according to a dosing regimen achieving a therapeutic effective amount repeated thrice, twice or once a week, once in two weeks, once in three weeks or at least once monthly.

The methods of the present invention are not limited to the treatment of NSLC. Instead, it will be readily understood that the bio-molecular pathways addressed and ALK inhibitors resistance obviated by the methods of the present invention may find application in the treatment of other disease conditions; any disease condition in which treatment with an ALK inhibitor would result in a beneficial result for a patient under treatment. "Beneficial results" may include, but are in no way limited to, lessening the severity of the disease condition, preventing the disease condition from worsening, curing the disease condition and prolonging a patient's life or life expectancy. These disease conditions may relate to or be modulated by EGFR or any other kinase that may be clinically affected with the methods of the present invention.

More specifically, the inventor's experimental studies as set forth in the following examples have demonstrated clinical activity of ALK inhibitors at the daily dosing regimens in molecular studies on these tumors demonstrated effective inhibition of the EGFR signaling cascade. The examples confirmed that the molecular studies properly reflected the behavior of these ALK inhibitors as observed in other model systems. The disclosure also surprisingly demonstrates that ALK inhibitors in combination with anti-EGF antibodies, which are passively administered or actively produced by the administration of a vaccine producing such antibodies, can inhibit tumor growth effectively in molecular models—even in tumors that demonstrated a resistance to conventional ALK inhibitor therapy.

In one illustrative embodiment the anti-EGF antibodies used in the pre-clinical studies are actively produced by immunizations with BVN22E vaccine as described in PCT application WO 2019/016597 A2 entitled: *Synthetic Proteins and Therapeutic Uses Thereof*. It is contemplated within the scope of the disclosure that other vaccine formulations that produce an immune response to EGF or EGFR may be used. It is also within the Scope of the disclosure that vaccines producing an immune response to other growth factors or their receptors may also be used. In particular, immunogenic protein BVN22E as set forth in WO 2019/016597 A2, the content of which is incorporated in its r entirety by reference, may be used to produce anti-EGF antibodies according to the disclosure.

BVN22E has a molecular weight of about 120 kDt, its EGF domain include the region which presents or constrains the β-loop, e.g., the region defined by about cysteine 6 to about cysteine 42, the region defined by about cysteine 6 to about cysteine 31 or the region defined by about cysteine 22 about cysteine 33 or the region defined by about cysteine 22 about cysteine 31 or the region defined by about cysteine 62 about cysteine 14 of the synthetic protein sequence. Without being bound by any particular theory, it is contemplated that different regions or sub-regions between cysteine 6 and cysteine 42 may have beneficial effects when incorporated into the synthetic proteins/molecules. It is thought that the following regions may have beneficial effects: the region between cysteine 6 and cysteine 14, the region between cysteine 6 and cysteine 20, the region between cysteine 6 and cysteine 31, the region between cysteine 6 and cysteine 33, and the region between cysteine 6 and cysteine 42. It is also contemplated that the reverse progressive sequence may also be beneficial. For example, the following regions may have beneficial effects: the region between cysteine 42 and cysteine 33, the region between cysteine 42 and cysteine 31, the region between cysteine 42 and cysteine 20, the region between cysteine 42 and cysteine 14, and the region between cysteine 42 and cysteine 6. It is further contemplated within the scope of the invention that specific intervals within the region between cysteine 6 and cysteine 42 may provide beneficial effects when incorporated into the synthetic proteins/molecules of the disclosure (e.g., the region between cysteine 6 and cysteine 14, the region between cysteine 14 and cysteine 20, the region between cysteine 20 and cysteine 31, and the region between cysteine 33 and cysteine 42).

BVN22E and its expressions of the growth factor epitopes fold in a manner allowing their natural conformation to be substantially retained and presented to components of the host immune system in such a way as to elicit a robust host immune response to said epitopes. Examples of suitable natural protein models to model an epitope supporting domain of a synthetic proteins/molecules include, but are not limited to, cholera toxin B sub-unit, *E. coli* heat-labile LT and LT-II enterotoxin B subunits, veratoxin, pertussis toxin, *C. jejuni* enterotoxin, Shiga toxin, *listeria* toxin, tetanus toxoid, diphtheria toxoid, N. meningitidisl outer membrane protein, bacteriophage coat protein, adenovirus and other viral coat proteins. Alternatively, a non-self component of the protein can be small. At a minimum, the non-self sequence(s) should comprise about 9, 10, 11 or more amino acids in length, and include either entirely or in-part at least one human T-cell epitope. Cholera toxin B sub-unit may be used that fulfill the requirements of conferring immunogenicity to the whole protein and allowing appropriate presentation of growth factors, receptors, tumor antigens or epitopes thereof to the host immune system.

BVN22E may be useful in treating chronic diseases, for example, breast, lung, bladder, ovarian, vulva, colonic, pulmonary, brain, colorectal, intestinal, head and neck, and esophagus cancers. As different tumor antigens can be expressed and multiple cellular receptors and growth factors over expressed in the said diseases, the proteins described hereunder can contain one or more different tumor antigens, one or more different receptors or growth factors of one or multiple cellular pathways associated with the disease. These proteins are called multivalent.

BVN22E is a synthetic protein comprised of a homogeneous synthetic proteins/molecules expressing one or more epidermal growth factor (EGF) neutralizing domains (e.g., TSP domains). The protein may be in the form of a synthetic proteins/molecules and may be useful in treating chronic diseases, for example, breast, lung, bladder, ovarian, vulva, colonic, pulmonary, brain, colorectal, head and neck, and esophagus cancers. BVN22E is a synthetic proteins/molecules expressing or including synthetic EGF sequences and CT-B sequences. BVN22E contains, a growth factor component of the synthetic protein sequence that includes a sequence that is less than 80% identical to EGF. For example, a growth factor component may include an EGF sequence with 11 amino acid substitutions that may increase the immunogenicity of the growth factor portion of the synthetic protein sequence. Without being bound by theory, it is believed that the region of EGF that 'presents' or constrains the β-loop (e.g., the region defined by Cys6 to Cys31) may be an important to include in the synthetic protein and amenable to target for amino acid modification.

BVN22E includes one or more linkers or spacers. One or more of the embodiments described above include sEGF fused to CT-B such that the sEGF portion of the synthetic molecule is separated from the CT-B portion by a GGSGGTSGGGGSG (SEQ ID NO: 3) linker. These resulting recombinant or chimeric proteins essentially included sEGF fused directly to CT-B. In other embodiments, the EGF and CT-B components of the chimeric protein are effectively separated by 3 to 14 amino acids, which form a flexible spacer or linker between the two domains. It is contemplated that the linker may be 3, 4, 5, 6, 7, 8, 9, 10, 11, 12, 13, or 14 amino acids in length. In some cases in which a growth factor has a larger size (e.g., human growth factor), it may be useful to use a longer linker sequence. The following exemplary linkers may also be used and include, but are not limited to, the following: SSG (SEQ ID NO: 4), SSGGG (SEQ ID NO: 5), SGG (SEQ ID NO: 6), GSSG (SEQ ID NO: 7), GGSGG (SEQ ID NO: 8), GGGGS (SEQ ID NO: 9), SSGGGSGG (SEQ ID NO: 10), SSGGGGSGGG (SEQ ID NO: 11), TSGGGSG (SEQ ID NO: 12), TSGGGGSGG (SEQ ID NO: 13), SSGGGSGGSSG (SEQ ID NO: 14), GGSGGTSGGGSG (SEQ ID NO: 15), SGGTSGGGGSGG (SEQ ID NO: 16), GGSGGTSGGGGSGG (SEQ ID NO: 16), SSGGGGSGGGSSG (SEQ ID NO: 17), SSGGGSGGSSGGG (SEQ ID NO: 18), and SSGGGGSGGGSSGGG (SEQ ID NO: 19). One of skill in the art will appreciate that there are many other sequences/combinations of primarily 'G' and 'S' that would also serve as useful linker sequences.

It is thought that BVN22E provides significant clinical benefits. For example, BVN22E may be expressed in bacterial systems at commercial scale and purity, while producing stable polypeptides that fold correctly and are functional. Additionally, BVN22E has the advantageous property of requiring much lower levels of protein for vaccination because the amount of carrier necessary significantly lower than prior art methods (e.g., U.S. Pat. No. 5,984,018 to Davila et al.). In this regard, BVN22E is able to deliver more growth factor to a patient in a significantly lower volume of vaccine.

While not wishing to be bound by any theory, it is believed that these suppression of the STAT3 metabolic pathway, which is required for stimulation of the cell signaling pathways responsible for cell proliferation, is aided by BVN22E. It is also believed that the additional inhibition of the STAT3 by the combination dosing regimen of the present invention is effective in inhibiting or down-regulating this cell signaling. Moreover, even those patients who are resistant to conventional ALK Inhibitor therapy may obtain a beneficial, anti-tumor effect by the combination dosing regimen of the present invention, because STAT3 is inhibited as well. The combination therapy of the present disclosure may be associated with hindrance of the disease condition where conventional ALK Inhibitor therapies failed. The methods of the present invention, therefore, can overcome resistance or non-responsiveness to ALK Inhibitor therapy by operating differently than conventional methods at the cellular and molecular level.

In particular embodiments, combination dosage of a ALK Inhibitors with anti-EGF antibodies may be effective in treating cancer, and especially lung, breast and prostate cancer, in an individual who is resistant to conventional ALK Inhibitor therapy. Other forms of cancer that may be treated with the methods of the present invention include, but are in no way limited to gastric, colorectal, and ovarian cancer, as well as glioblastoma tumors. Each of these forms of cancer demonstrates significant EGFR expression, making them suitable targets for treatment in accordance with the methods of the present invention.

ALK Inhibitors suitable for use in accordance with the methods of the present invention may include, but are in no way limited to Crizotinib, Ceritinib, Alectinib, Brigatinib and Lorlatinib or a pharmaceutically acceptable salt thereof, or equivalents of the same; all of which are included within the term "ALK Inhibitors." The efficacy of a given treatment for cancer can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc. In addition, efficacy of an agent can be measured by a decrease in circulating MIC peptides or fragments thereof in a subject being treated with an agent comprising an antibody or antigen-binding portion thereof as described herein or a nucleic acid encoding an antibody or antigen-binding portion thereof as described herein.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

This invention is further illustrated by the following examples, which should not be construed as limiting.

Example 1: Effects of the Combination of ALK Inhibitors and Anti-EGF Antibodies in Non-Small Cell Lung Carcinoma Cell Lines Patients treated with ALK TKI's achieve a longer progression-free survival period compared to EGFR mutated patients treated with EGFR TKI's. In the clinic, 20 to 30% of patients rapidly become resistant. It is not known however if these patients become resistant or are never responsive. It is also unclear what the effect is of circulating EGF in these patients. The instant disclosure addresses the effect of EGF on TKI resistance, employing two cell lines containing the main ALK rearrangements of NSCLC patients The effects of BVN22E antibodies in combination with the following ALK TKIs—Crizotinib, Alectinib and Brigantinib—were tested on two cell lines containing the main ALK rearrangements of NSCLC patients. ALK "rearrangements" refers to a number of different mutations. These lines are shown in FIG. 1: H3122 lung adenocarcinoma containing EML4-ALK fusion variant v1 and H2228 lung adenocarcinoma containing EML4-ALK fusion variant v3 that together represent about 30-40% of ALK rearrangement patients.

All studies and the resulting examples were conducted with anti-BVN22E antibodies prepared in rabbits and then purified. The two step purification process led to approximately 10 fold dilution of the initial serum collected from the immunized rabbits. All experiments were conducted with further dilutions wherein a 1 to 10 dilution corresponded to 1 to 100 dilution of the original titer.

Figure 4:
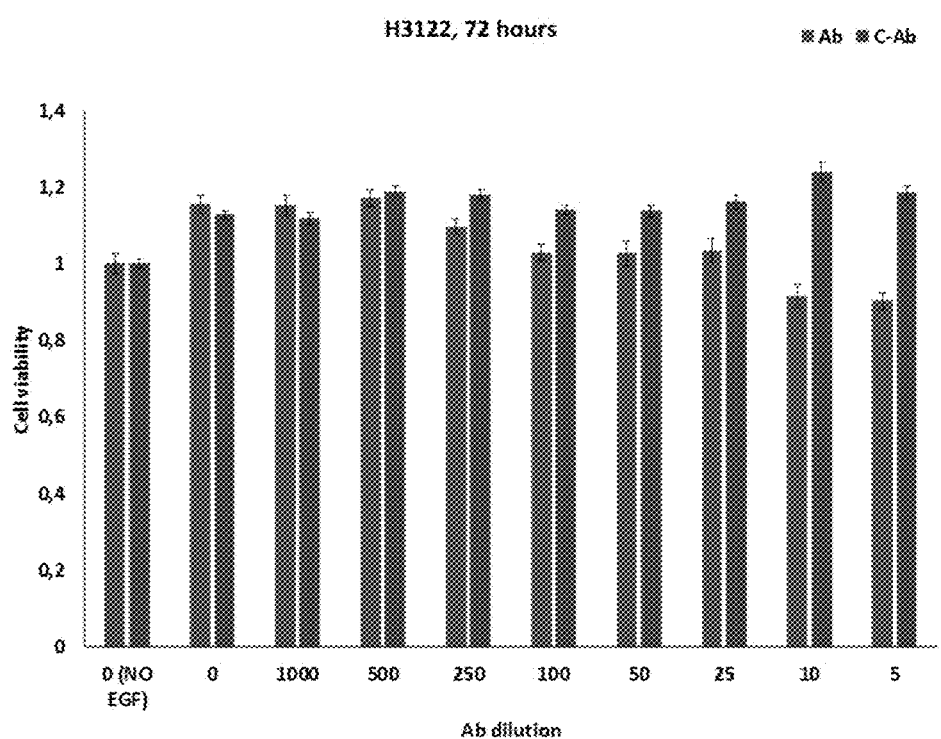
FIG. 4 shows the effect on cell viability of BVN22E antibodies incubated for 72 hours in the H3122 cell line. C-Ab is the control antibody.

The effects of Brigatinib and Alectinib on H3122 cell proliferation were measured alone, and in the presence of EGF. The results, see FIG. 2A-B, show that Brigatinib and Alectinib alone each had a greater inhibitory effect on H3122 cell proliferation than did Brigatinib and Alectinib each in the presence of EGF. Similarly, Crizotinib had a greater inhibitory effect on H3122 cell proliferation than did Crizotinib in the presence of EGF, see FIG. 3. The effects of BVN22E antibodies in H3122 cells in the presence of EGF were evaluated in a 72 hour cellular proliferation assay, shown in FIG. 4. The data demonstrate that BVN22E antibodies induced a reduction in H3122 cell viability relative to the control antibody.

Figure 5:
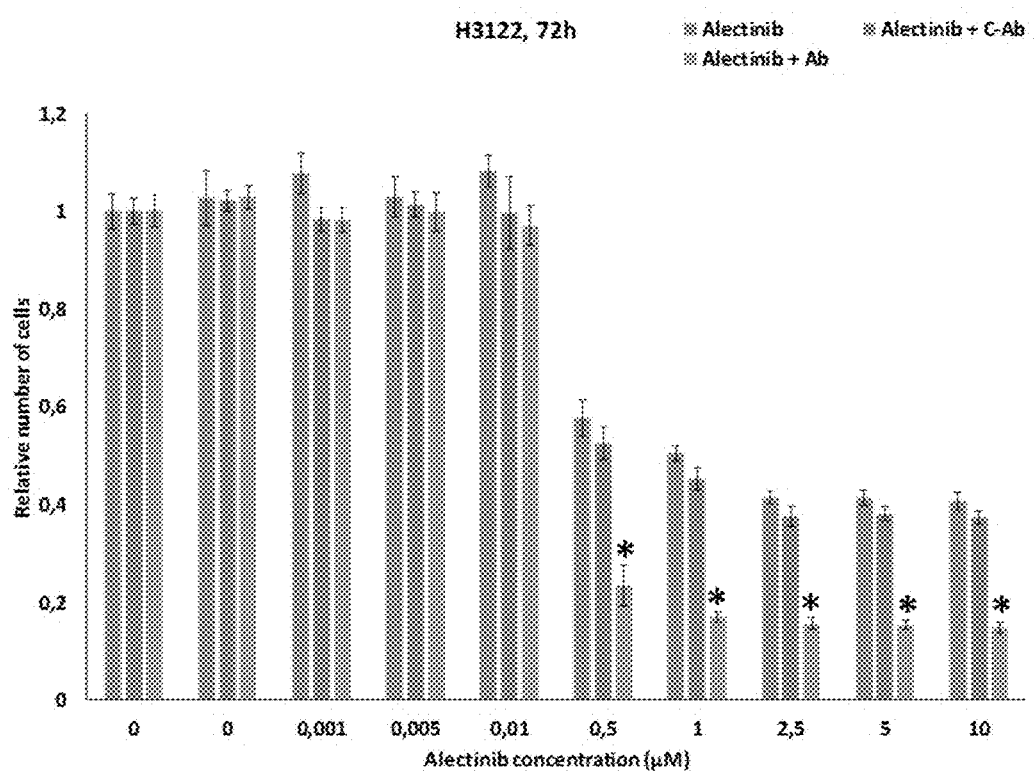
FIG. 5 shows the effect on cell viability of the combination of BVN22E antibodies and Alectinib after 72 hour incubation in H3122 cells.
Figure 6:
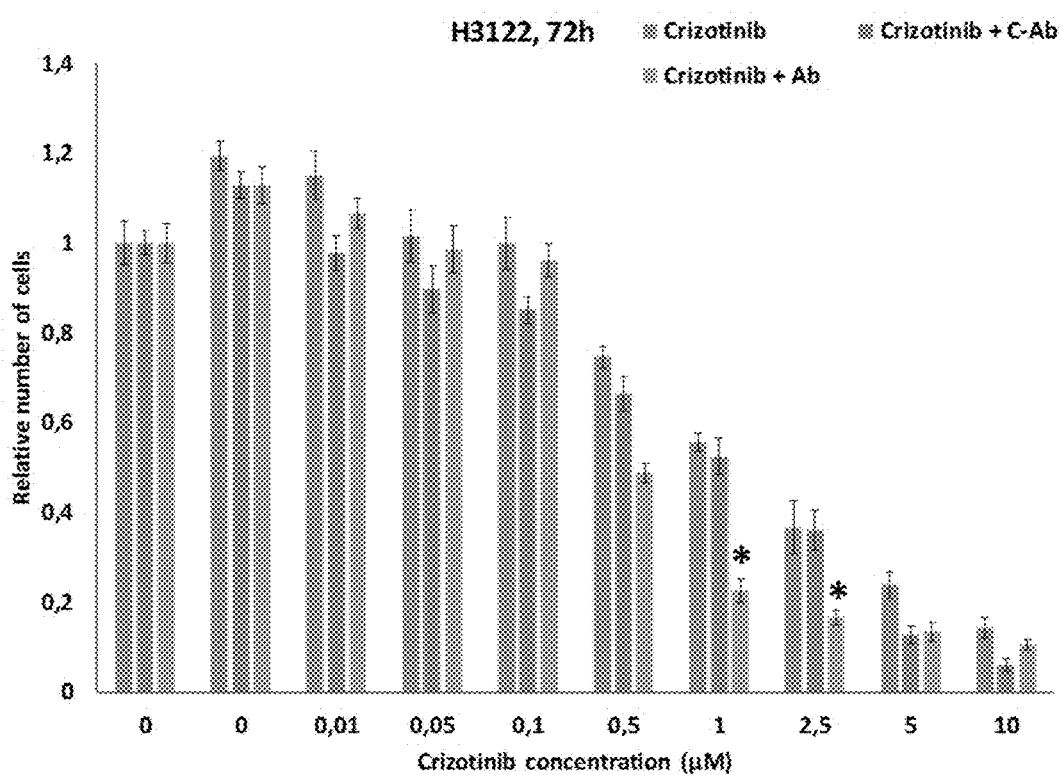
FIG. 6 shows the effect on cell viability of the combination of BVN22E antibodies and Crizotinib after 72 hour incubation in H3122 cells.

Next, the effects of ALK inhibitors in combination with BVN22E antibodies were measured. The effect of Alectinib as a single treatment or in combination with BVN22E antibodies on H3122 cells 72 hour cell proliferation are shown in FIG. 5. The effect of Critzotinib as a single treatment or in combination with BVN22E antibodies on H3122 cells 72 hour cell proliferation are shown in FIG. 6. For both TKI inhibitors, a significantly greater reduction in cell viability was seen with the combination of BVN22E antibodies and inhibitor, than for either inhibitor alone, however the effect was stronger for Alectinib in combination with BVN22E antibodies than for Critzotinib. The effects of Brigatinib and Alectinib as single treatments or in combination with BVN22E antibodies on H31122 and H2228 cell viability are shown in FIG. 7.

Figure 9:
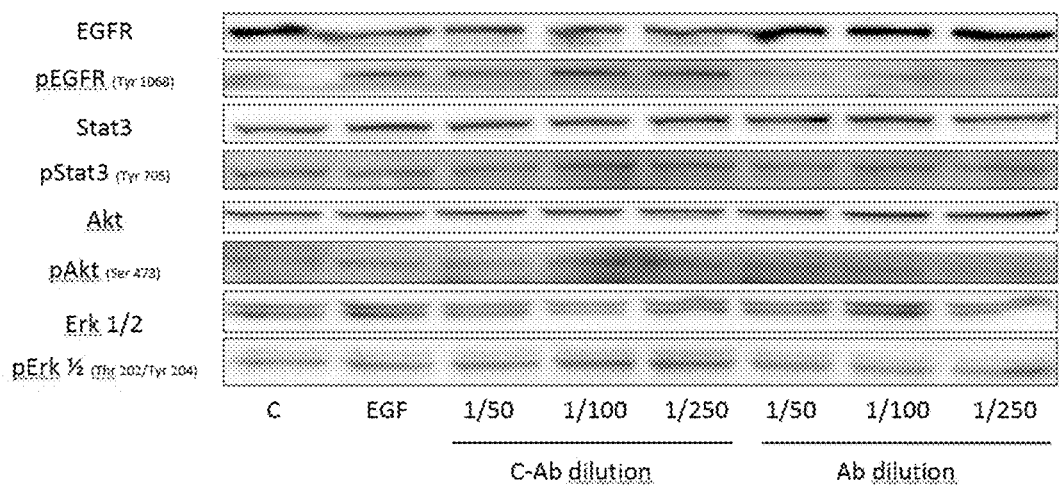
FIG. 9 shows the effect on pEGFR (TYR 1068), pSTAT3 (TYR 705), pAKT (SER 473), and ERK1/2 (THR 202/TYR 204) in response to 24 hour incubation with BVN22E antibodies in H3122 cells.

The effects of BVN22E antibodies in H3122 cells were evaluated by western blot following 2 hour incubation of BVN22E antibodies at concentrations of 1/25, 1/50, and 1/250, as shown in FIG. 8. The presence of EGFR, AKT, STAT 3 and ERK1/2 were revealed with specific monoclonal antibodies. Antibodies to the phosphorylated forms of the molecules were also used. C stands for control, non-treated cell line sample. Second lane is same control cell receiving EGF, all other lanes dilutions of control antibodies and anti BVN22E antibodies. These data demonstrate that significant inhibition of pEGFR occurred, whereas pAkt, pStat3, and pErk ½ levels did not change. The effects of BVN22E antibodies in H3122 cells were evaluated by western blot following 24 hour incubation of BVN22E antibodies at concentrations of 1/25, 1/50, and 1/250, as shown in FIG. 9. These data demonstrate that significant inhibition of pEGFR was maintained 24 hours after incubation with BVN22E antibodies. The effects of Crizotinib in H3122 cells were evaluated by western blot following 2 hour incubation of Crizotinib at concentrations of 0.1, 0.25, 0.5, 1, 2.5, and 5 as shown in FIG. 10. These data demonstrate that significant inhibition pStat3, as well as inhibition of pAkt, were observed 2 hours after incubation with Crizotinib.

Figure 12:
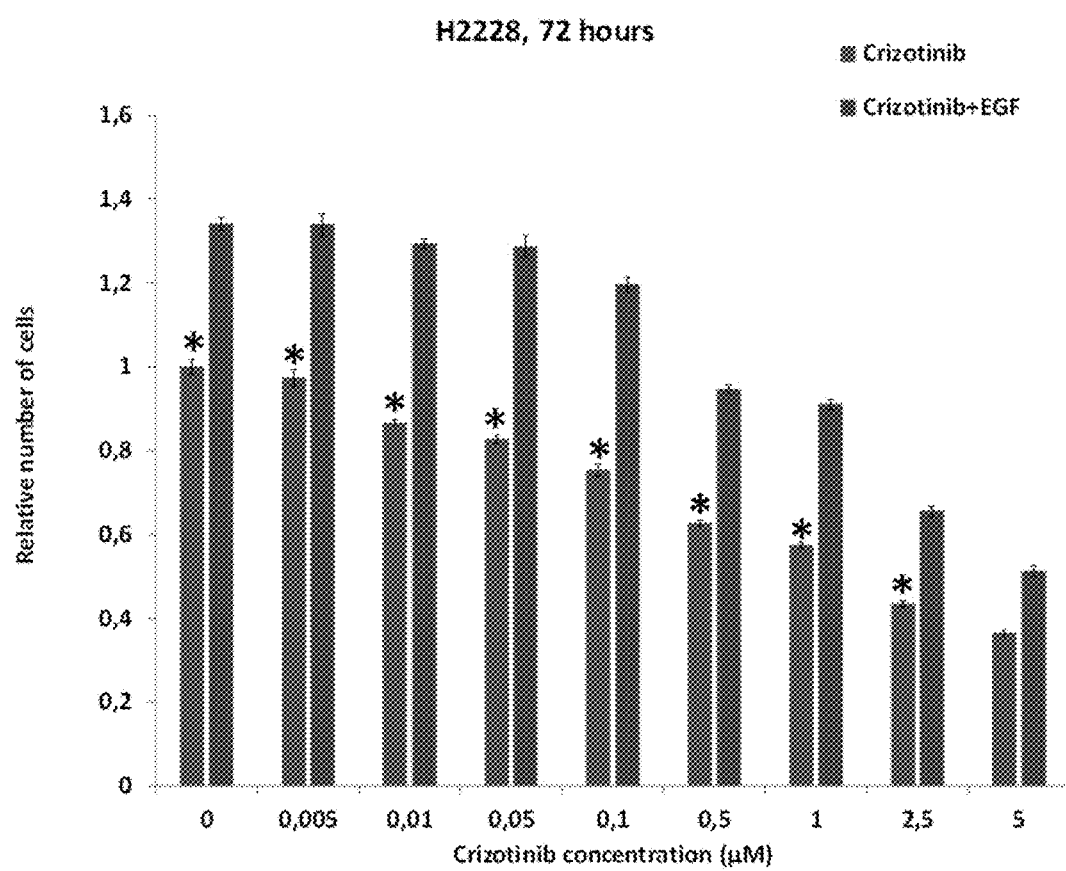
FIG. 12 shows the effect on cell viability of Crizotinib in the presence and absence of EGF in the H2228 cell line after 72 hour incubation.
Figure 13:
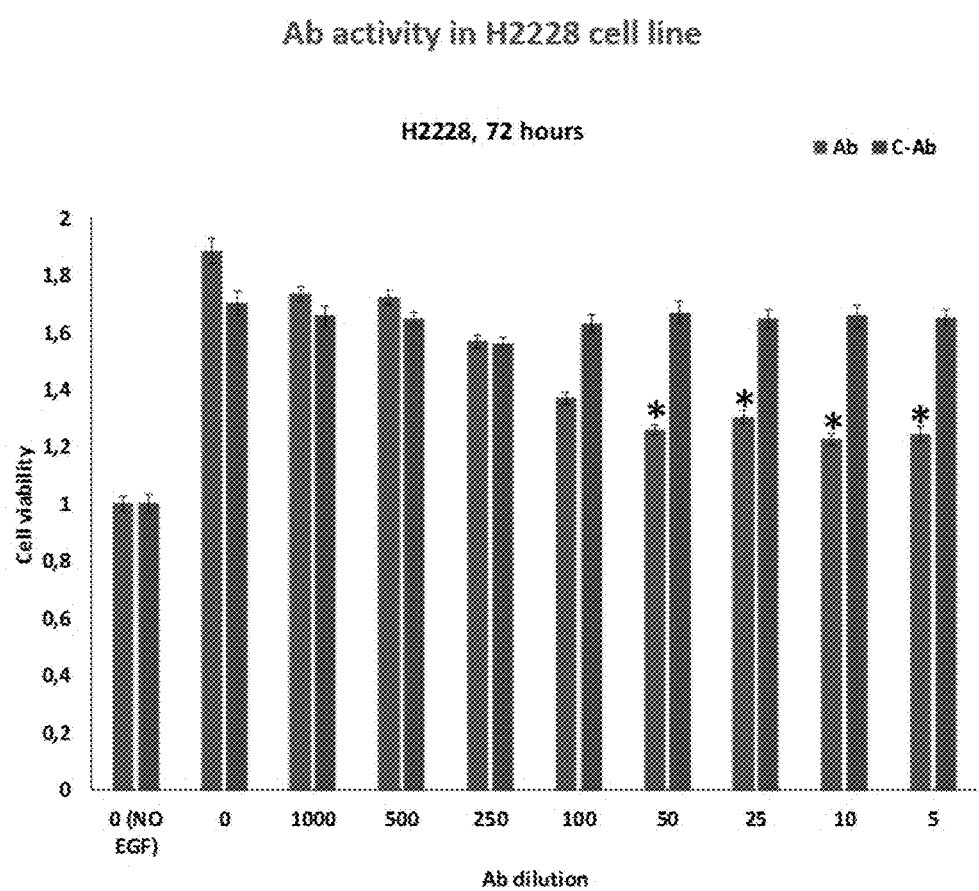
FIG. 13 shows the effect on cell viability of BVN22E antibodies incubated for 72 hours in the H2228 cell line. C-Ab is the control antibody.
Figure 14:
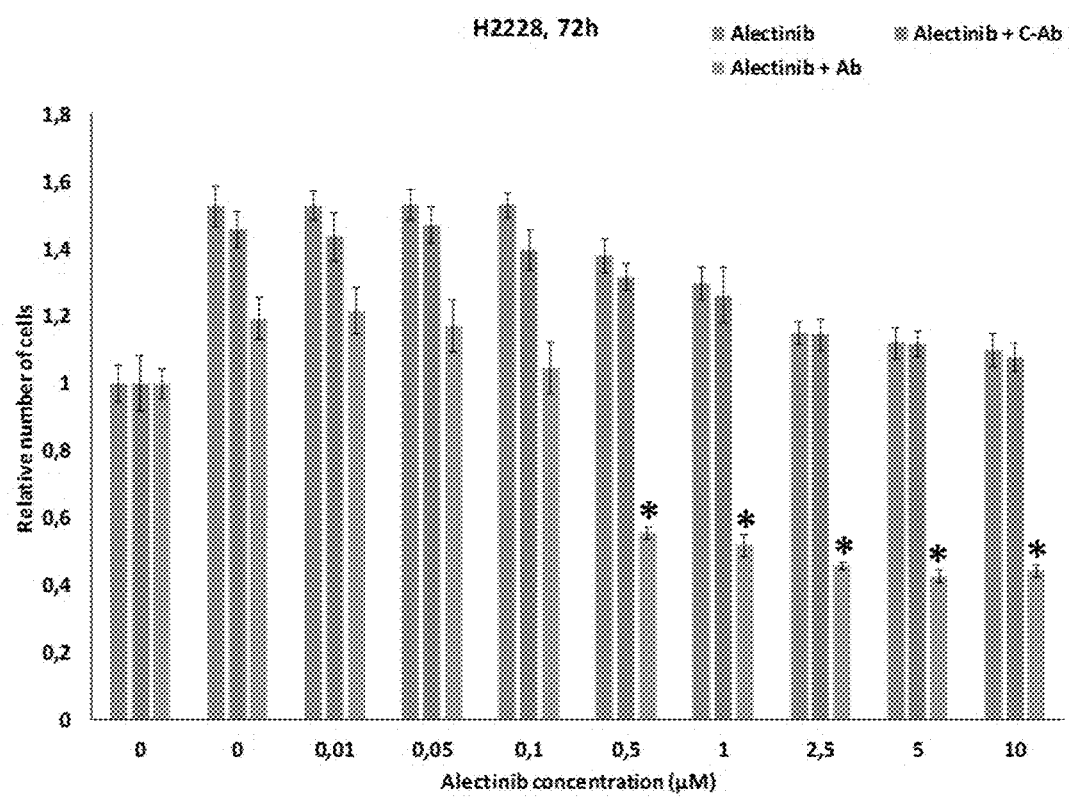
FIG. 14 shows the effect on cell viability of the combination of BVN22E antibodies and Alectinib after 72 hour incubation in H2228 cells.

The effects of Brigatinib and Alectinib on H2228 cell proliferation were measured alone, and in the presence of EGF. The results show that Brigatinib and Alectinib each alone had a greater inhibitory effect on H3122 cell proliferation, see FIG. 11, than did Brigatinib and Alectinib in the presence of EGF. FIG. 12 shows the effect of Crizotinib on H3122 72 hour cell proliferation, alone, and in the presence of EGF. The results show that Crizotinib alone has a greater inhibitory effect on H3122 cell proliferation than does Crizotinib in the presence of EGF. FIG. 13 shows the effect on cell viability of BVN22E antibodies in the presence of EGF in H2228 cells. At higher concentrations of BVN22E antibodies, a significant reduction in cell viability was observed.

Figure 15:
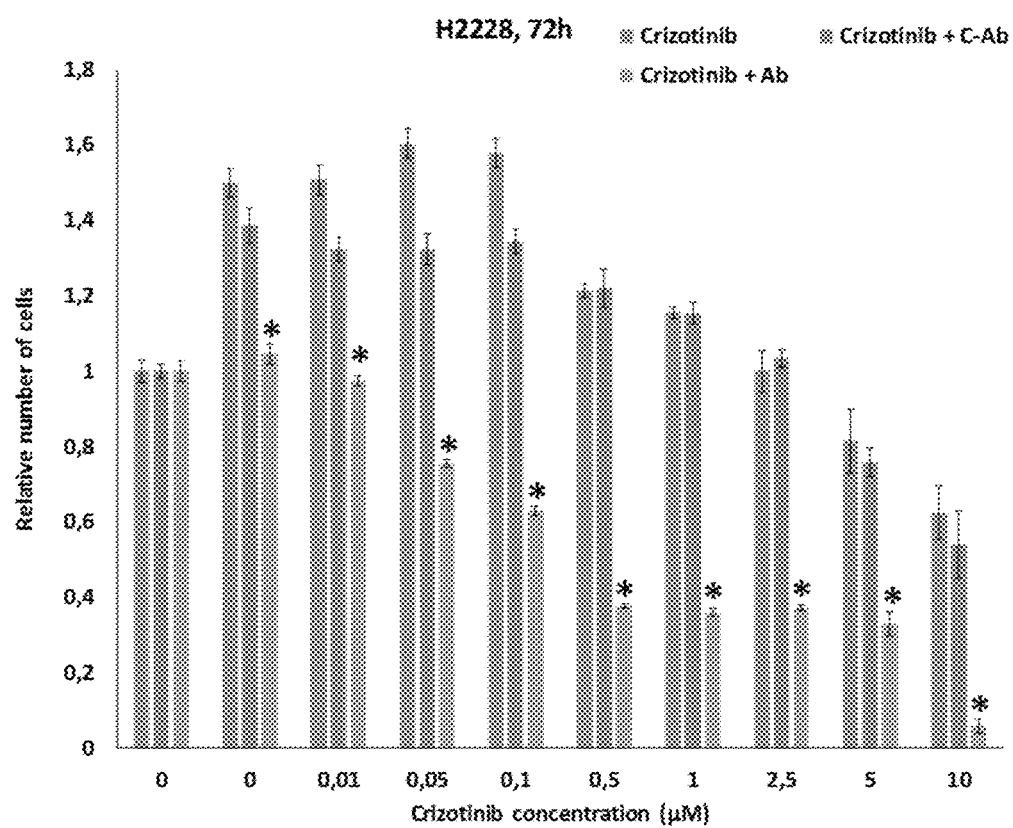
FIG. 15 shows the effect on cell viability of the combination of BVN22E antibodies and Crizotinib after 72 hour incubation in H2228 cells.

Next, the effects of ALK inhibitors in combination with BVN22E antibodies were measured. The effect of Alectinib as a single treatment or in combination with BVN22E antibodies on H2228 cells 72 hour cell proliferation was assessed. Although Alectinib had minimal effect on cell viability, the combination of higher concentrations of Alectinib and BVN22E antibodies induced a significant reduction in cell viability, see FIG. 15. With Critzotinib, even low concentrations of Crizotinib in combination with BVN22E antibodies induced a significant reduction in cell viability, see FIG. 15. The ALK tyrosine kinase inhibitors Brigatinib and Alectinib in combination with BVN22E antibodies induced a striking inhibition of cellular proliferation in H2228 cells, see FIG. 16A.

Figure 17:
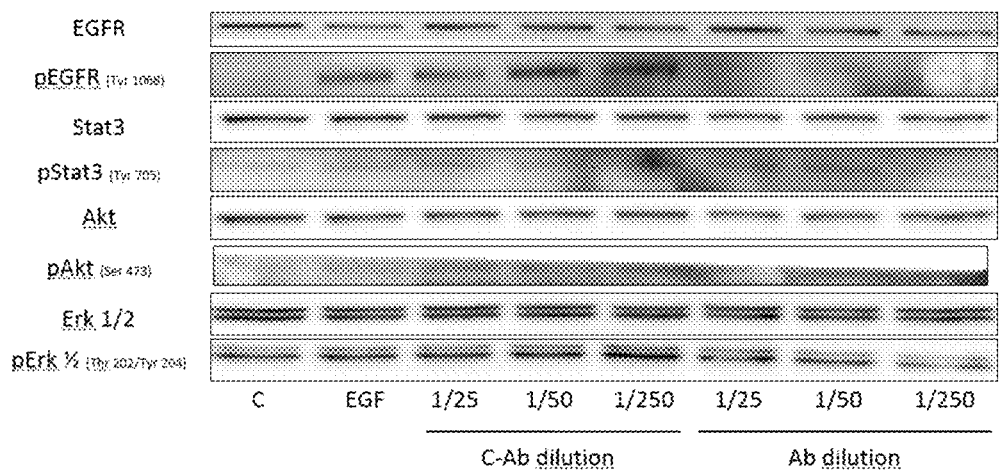
FIG. 17 shows the effect on pEGFR (TYR 1068), pSTAT3 (TYR 705), pAKT (SER 473), and ERK1/2 (THR 202/TYR 204) in response to 2 hour incubation with BVN22E antibodies in H2228 cells.

The effects of BVN22E antibodies in H2228 cells were next evaluated by western blot following 2 hour incubation of BVN22E antibodies at concentrations of 1/25, 1/50, and 1/250, as shown in FIG. 17. These data demonstrate that significant inhibition of pEGFR occurred, with some inhibition of pERK1/2, whereas pAkt and pStat3 levels did not change.

Figure 18:
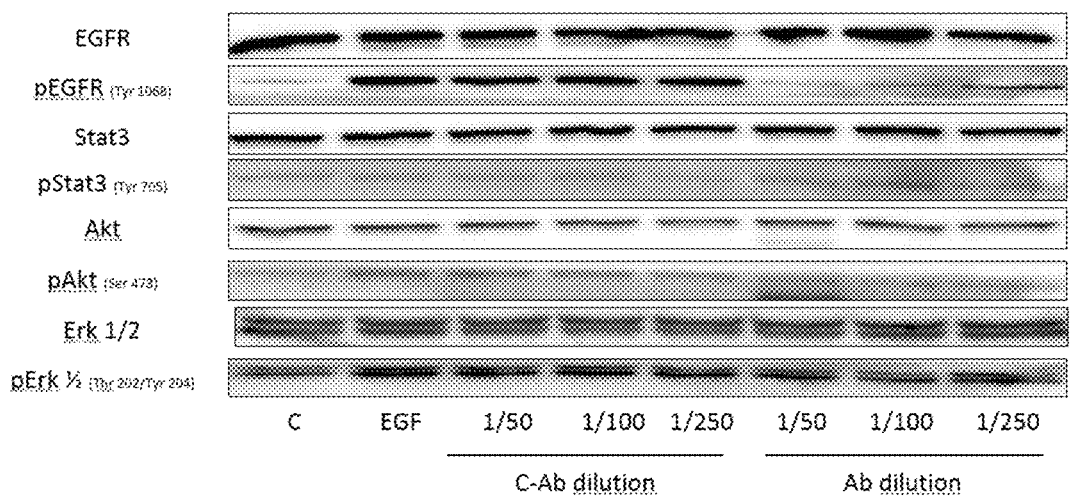
FIG. 18 shows the effect on pEGFR (TYR 1068), pSTAT3 (TYR 705), pAKT (SER 473), and ERK1/2 (THR 202/TYR 204) in response to 24 hour incubation with BVN22E antibodies in H2228 cells.

The effects of BVN22E antibodies in H2228 cells were next evaluated by western blot following 24 hour incubation of BVN22E antibodies at concentrations of 1/25, 1/50, and 1/250, as shown in FIG. 18. These data demonstrate that significant inhibition of pEGFR was maintained 24 hours after incubation with BVN22E antibodies.

Figure 19:
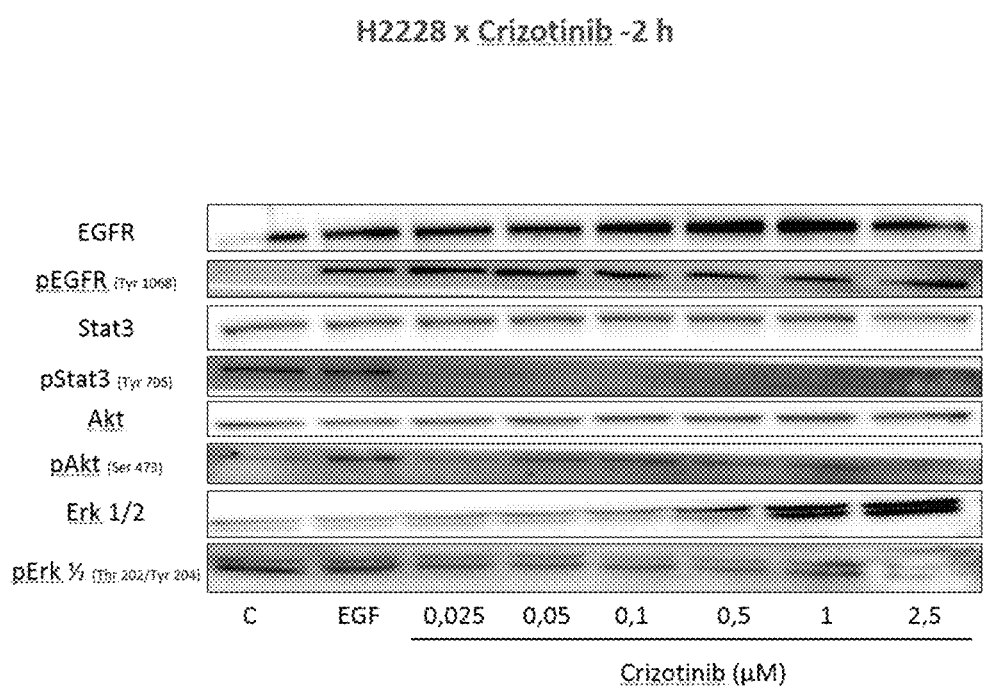
FIG. 19 shows the effect on pEGFR (TYR 1068), pSTAT3 (TYR 705), pAKT (SER 473), and ERK1/2 (THR 202/TYR 204) in response to 2 hour incubation with Crizotinib in H2228 cells.
Figure 20:
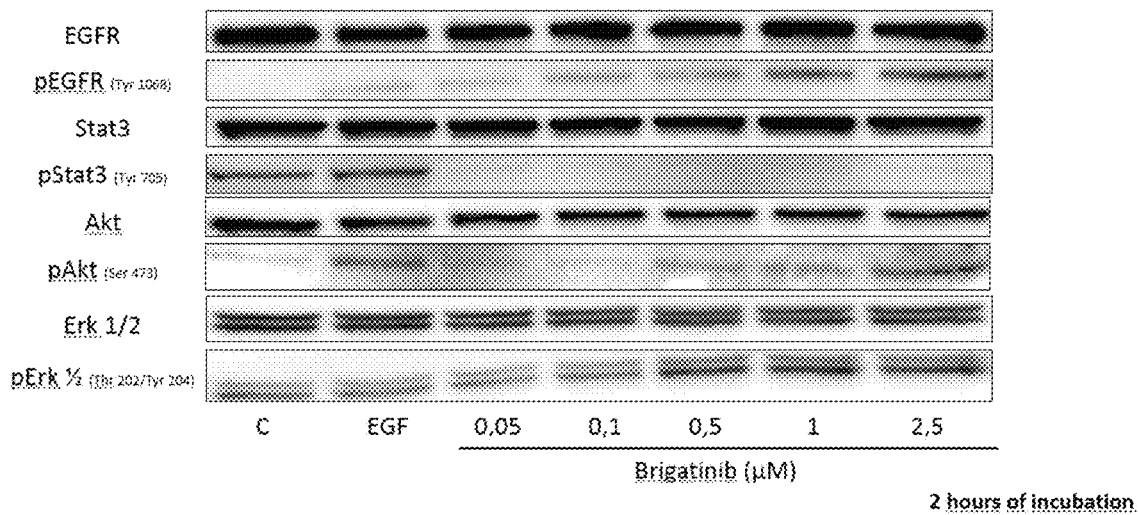
FIG. 20 shows the effect on pEGFR (TYR 1068), pSTAT3 (TYR 705), pAKT (SER 473), and ERK1/2 (THR 202/TYR 204) in response to 2 hour incubation with Brigatinib in H2228 cells.
Figure 21:
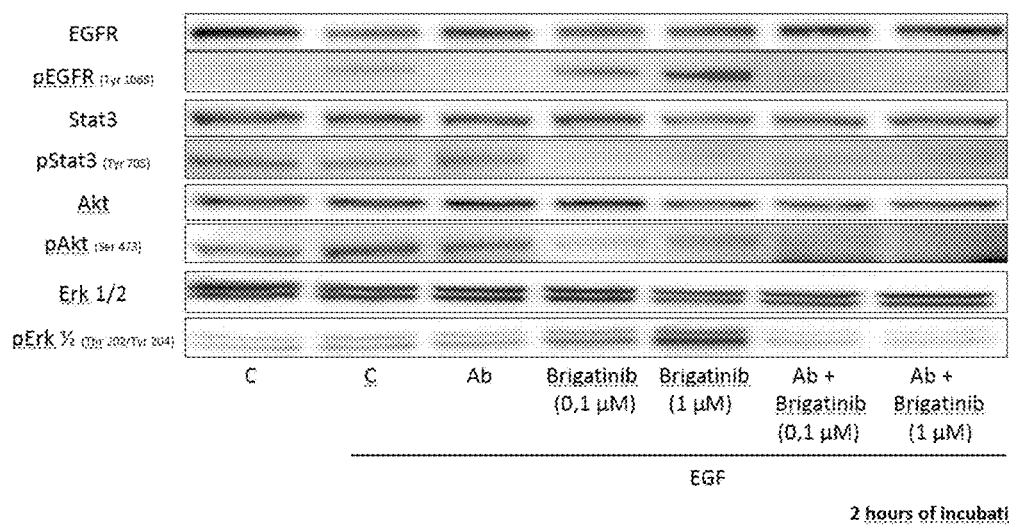
FIG. 21 of shows the effect on pEGFR (TYR 1068), pSTAT3 (TYR 705), pAKT (SER 473), and ERK1/2 (THR 202/TYR 204) in response to 2 hour incubation with the combination of BVN22E antibodies and Brigatinib in H2228 cells.

The effects of Crizotinib in H2228 cells were next evaluated by western blot following 2 hour incubation of Crizotinib at concentrations of 00.025, 0.05, 0.1, 0.5, 1, and 2.5 µM as shown in FIG. 19. These data demonstrate that significant inhibition pStat3 was observed 2 hours after incubation with Crizotinib. Similarly, Brigatinib significantly inhibited pSTAT3, and high concentrations of Brigatinib (1 and 2.5 µM) induced an increase in pEGFR and pAKT, see FIG. 20. Notably, BVN22E antibodies in combination with Brigatinib prevented the activation of pEGFR and pERK in H2228 cells, see FIG. 21.

Figure 22:
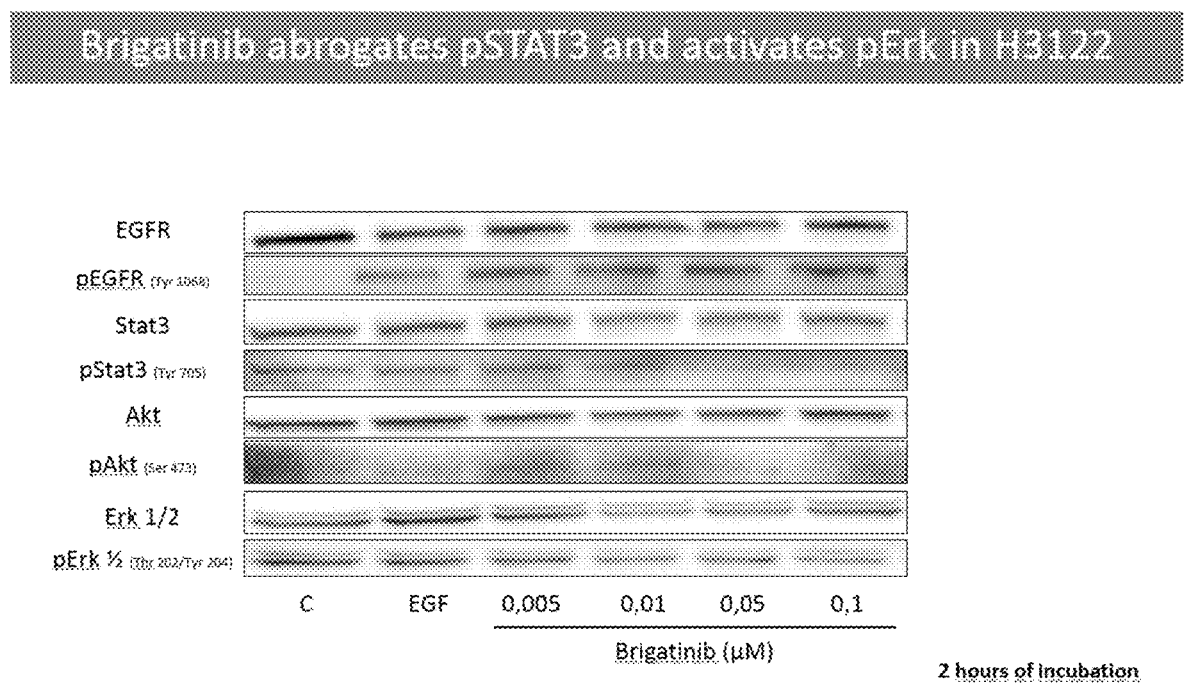
FIG. 22 shows the effect on pEGFR (TYR 1068), pSTAT3 (TYR 705), pAKT (SER 473), and ERK1/2 (THR 202/TYR 204) in response to 2 hour incubation with Brigatinib in H3122 cells.
Figure 23:
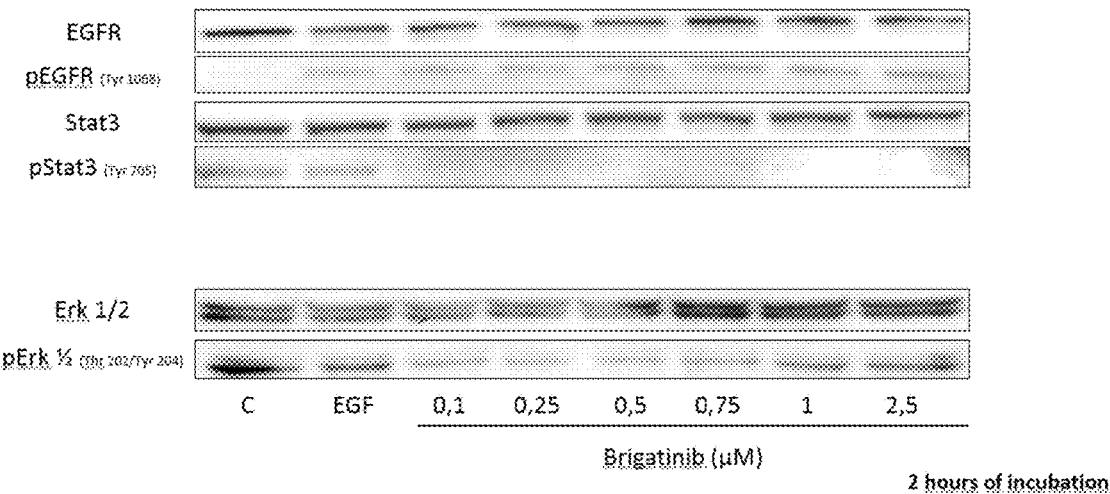
FIG. 23 shows the effect on pEGFR (TYR 1068), pSTAT3 (TYR 705), pAKT (SER 473), and ERK1/2 (THR 202/TYR 204) in response to 2 hour incubation with high concentrations of Brigatinib in H3122 cells.
Figure 24:
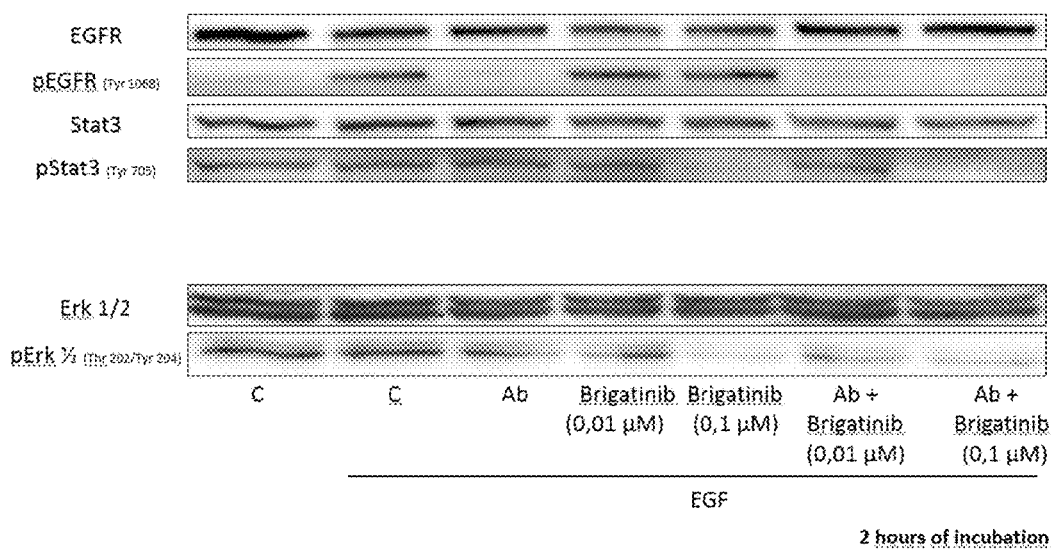
FIG. 24 shows the effect on pEGFR (TYR 1068), pSTAT3 (TYR 705), pAKT (SER 473), and ERK1/2 (THR 202/TYR 204) in response to 2 hour incubation with the combination of BVN22E antibodies and Brigatinib in H3122 cells.

Brigatinib significantly inhibited pSTAT3, and slight inhibition of pERK1/2 was seen in H3122 cells, see FIG. 22. Brigatinib at higher concentrations also significantly inhibited pSTAT3, and slightly inhibited pERK1/2 in H3122 cells. In contrast, BVN22E antibodies in combination with Brigatinib completely inhibited the activation of pEGFR and pERK in H2228 cells, see FIG. 24.

It is known that patients become resistant to single treatments of ALK TKIs. Next it was investigated whether the combinations of Crizotinib or Alectinib with and BVN22E antibodies could delay onset of resistance to ALK TKIs in H2228 cells. In these studies, the combination of the TKI inhibitor and BVN22E antibodies were added to the cells each time the cell culture medium was replaced, from 1-2 times per week. Studies were conducted in 96 well microplates which were imaged with a microscope to determine the percentage of wells containing resistant colonies.

Figure 25:
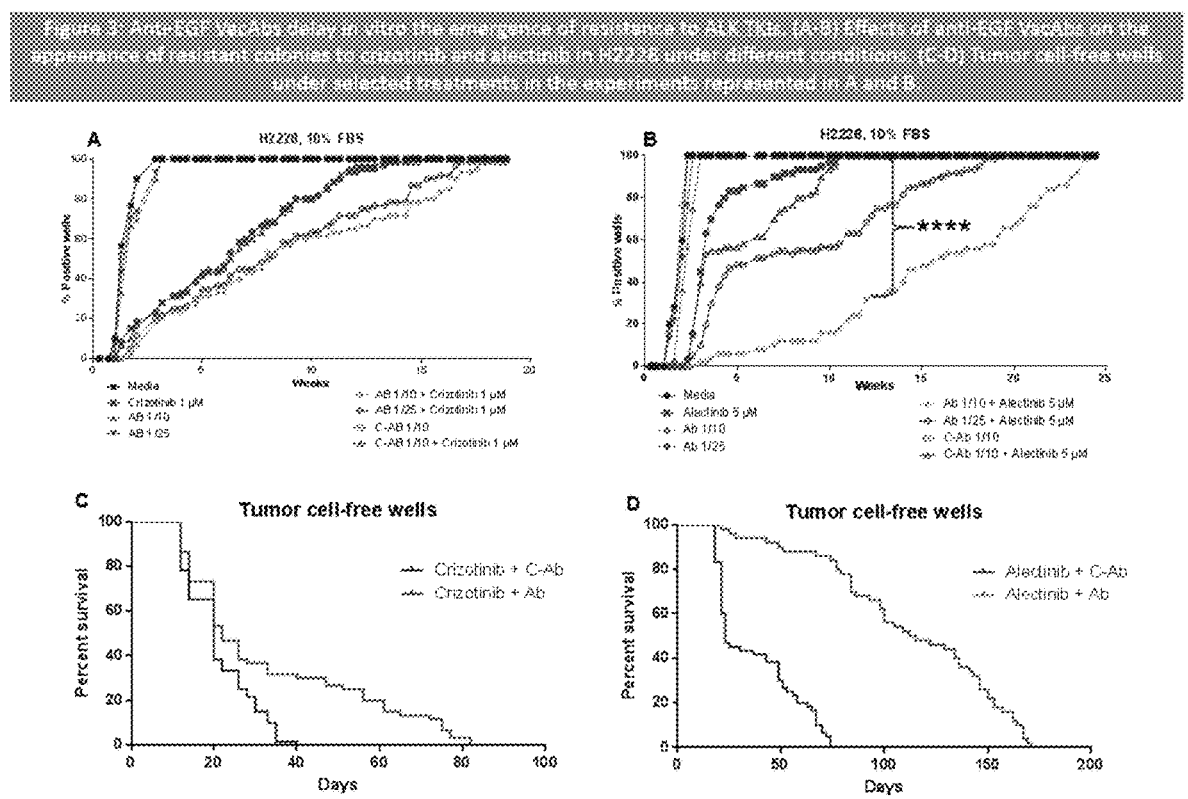
FIG. 25 shows the time to onset of resistance to Crizotinib and Alectinib in H2228 cells in the presence and absence of BVN22E antibodies under different growth conditions, represented by the appearance of resistant colonies (top panels) and the delay to cell death (bottom panels)
Figure 26:
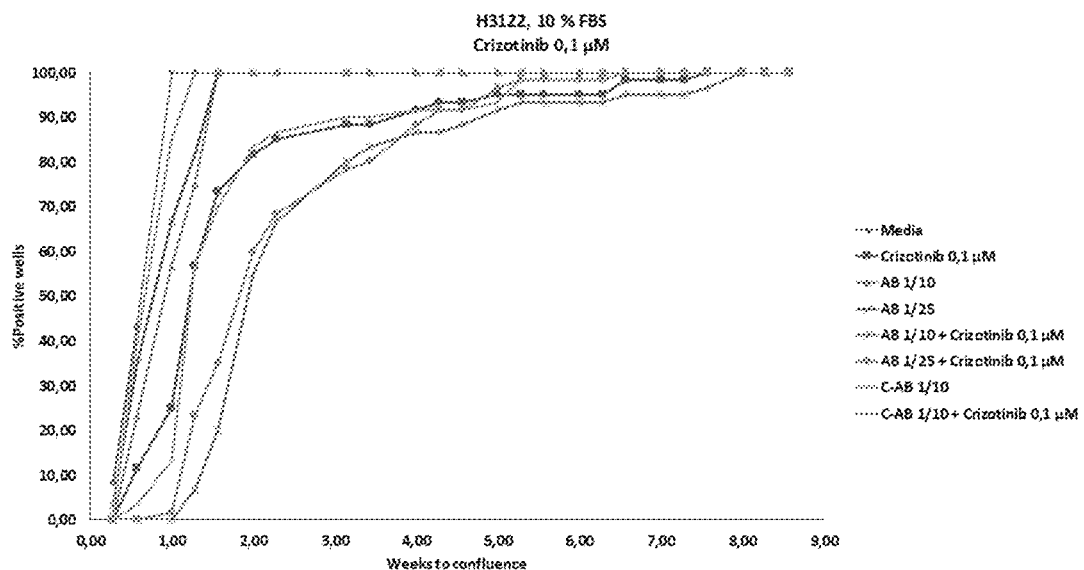
FIG. 26 shows the emergence of resistance to Crizotinib 0.1 μM in H3122 cells in the presence and absence of BVN22E antibodies.

BVN22E antibodies delayed the in vitro onset of resistance to ALK TKIs. Experiments with Crizotinib (FIG. 25A) and, to a greater extent, with Alectinib (FIG. 25B), demonstrated that the combination treatment kept proliferation under control for longer period of time, indicating a delay in the onset of resistance. For Alectinib alone, all wells showed active replication after 10 weeks, whereas the combination delayed replication for a longer period. Notably, when the highest concentration of BVN22E antibodies was used in combination with Alectinib, 100% resistance was not reached until 25 weeks. FIG. 25C (Crizotinib) and FIG. 25D (Alectinib) present the same experiments but instead of the percentage of positive wells, the percentage of tumor cell free wells are shown; this presents the instant disclosure's results in a similar mode to the Kaplan Meyer curve in clinical trials, in which the y-axis intercept corresponds to the point of zero patient survival. Similarly, in H3122 cells, BVN22E antibodies delayed the emergence of resistance to 0.1 µM and 0.2 µM of Crizotinib in H3122 cells, see FIGS. 26 and 27.

Notably, the combination of ALK TKI and BVN22E antibodies in 3-day proliferation assays demonstrated significant improvements over ALK TKIs alone in terms of the in vitro inhibition of cell proliferation and the regulation of EGF signaling pathways. The combination strengthened the effect of the ALK TKI, neutralized the negative effects of the ALK TKI, and broadened the inhibition of all signaling molecules assessed. This stronger and broader inhibition of EGF signaling was supported by the significant delay of onset of ALK TKI resistance by H228 cells, up to 2-fold, in the presence of both ALK TKIs and BVN22E antibodies compared to ALK TKIs alone.

Example 2: Assessment of the Combination of Anti-EGF Antibodies and Trametinib in BRAF and KRAS Mutation Cell Lines Colorectal cancer (CRC) is not only one of the most widely common tumorous cancers but is also known to be particularly challenging to treat. CRC Patients without KRAS mutations can be treated with therapies targeting EGF such as Cetuximab and Erlotinib in the clinic. However, there is a large cohort of CRC patients harboring KRAS mutations, BRAF mutations or PIK3CA mutations. There are currently no effective treatments available for those patients. Chemotherapy and angiogenesis targeting are commonly used but have significant drawbacks.

To begin to address the need for treatment of CRC patients with KRAS, BRAF, or PIK3CA mutations, EGF antibodies in combination with the MEK inhibitor, Trametinib, were tested in vitro in cell lines with the aforementioned mutations. All experiments were conducted in combination with antibodies to BVN22E.

Figures 27, 28:
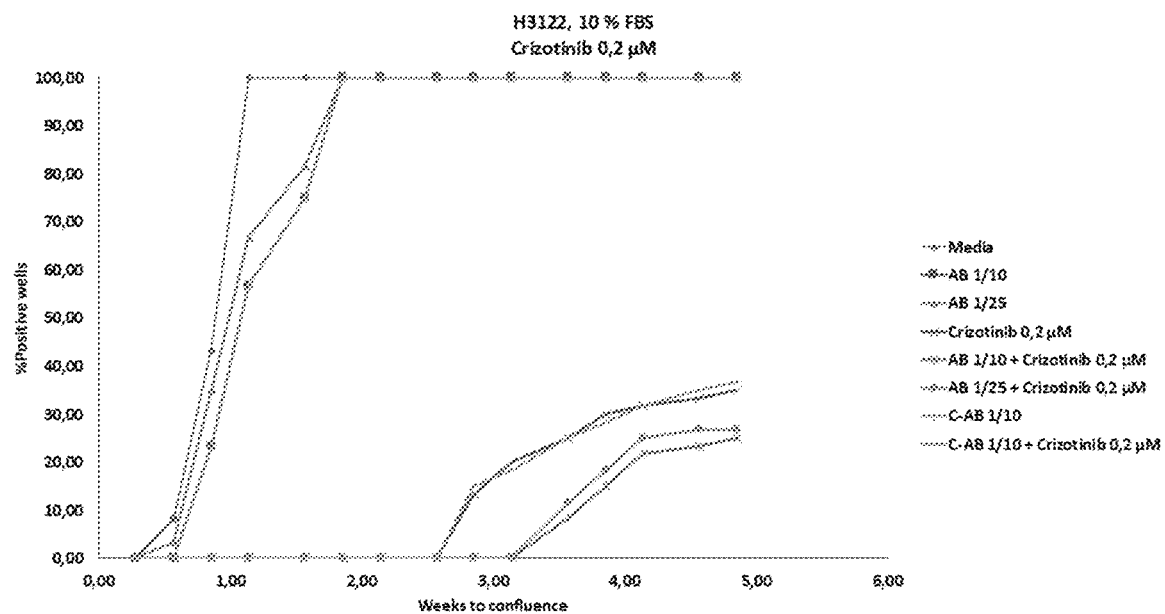
FIG. 27 shows the emergence of resistance to Crizotinib 0.2 μM in H3122 cells in the presence and absence of BVN22E antibodies.
FIG. 28 illustrates the BRAF mutant cell line used in the instant disclosure. The HT29 line is of colon adenocarcinoma origin and contains the V600E BRAF mutation.
Figure 29:
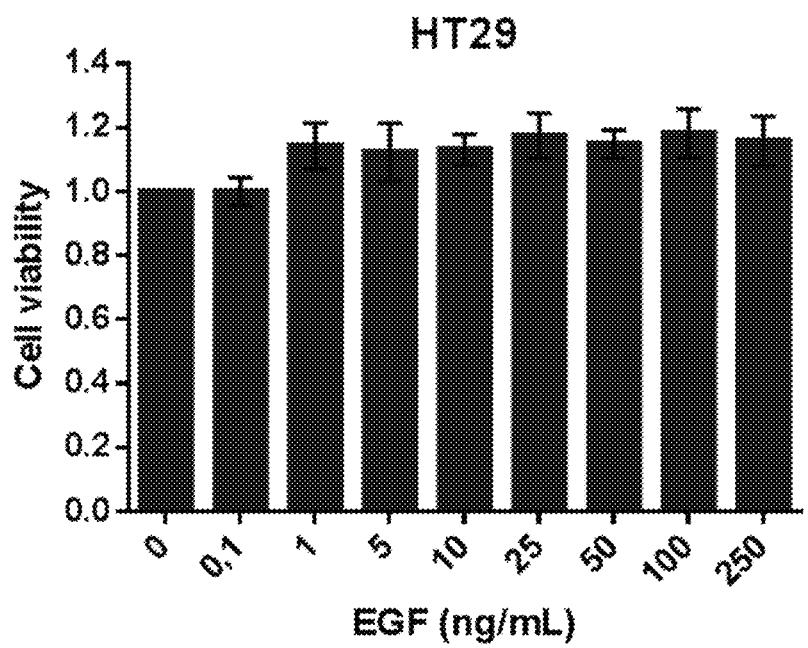
FIG. 29 shows the effect of EGF on HT29 cell viability.
Figure 30:
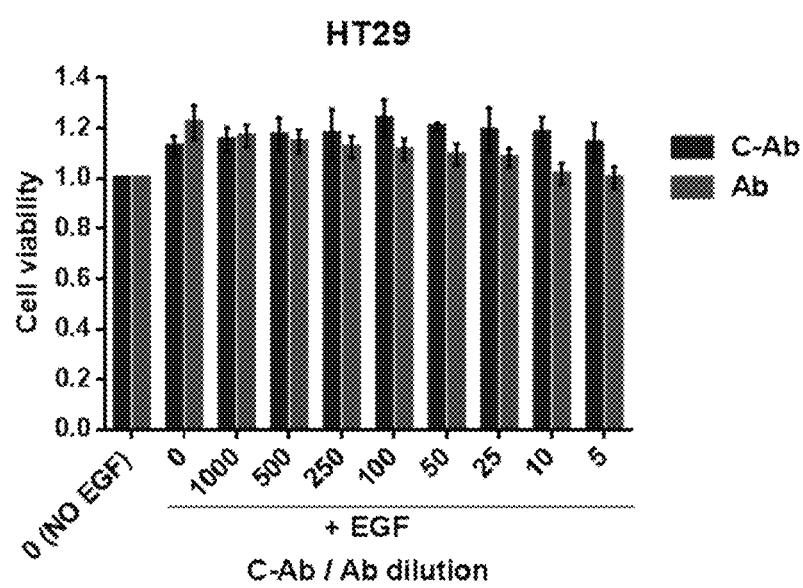
FIG. 30 shows the effect on cell viability of BVN22E antibodies in the presence and absence of EGF in HT29 cells.
Figure 31:
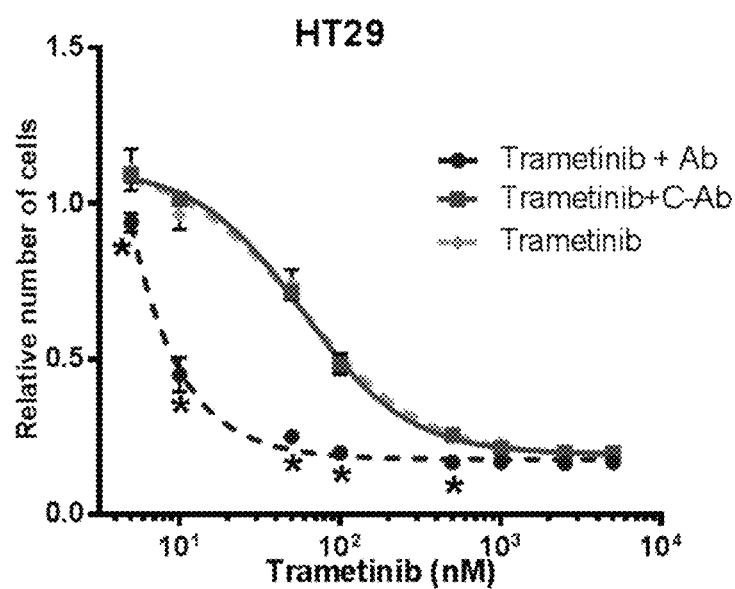
FIG. 31 shows the effect on cell viability of BVN22E antibodies in combination with Trametinib in the HT29 cell line.

Cell viability of HT29, also a colorectal adenocarcinoma cell line but with a BRAF V66E mutation, was investigated (see FIG. 28). HT29 cell viability can be enhanced with EGF, as shown in FIG. 29. The effect on cell viability of BVN22E antibodies and Trametinib, alone and in combination, were assessed in HT29 cells, as shown in FIGS. 30 and 31. BVN22E antibodies in combination with Trametinib exhibited significantly greater inhibition of cell proliferation compared with Trametinib alone.

Figure 32:
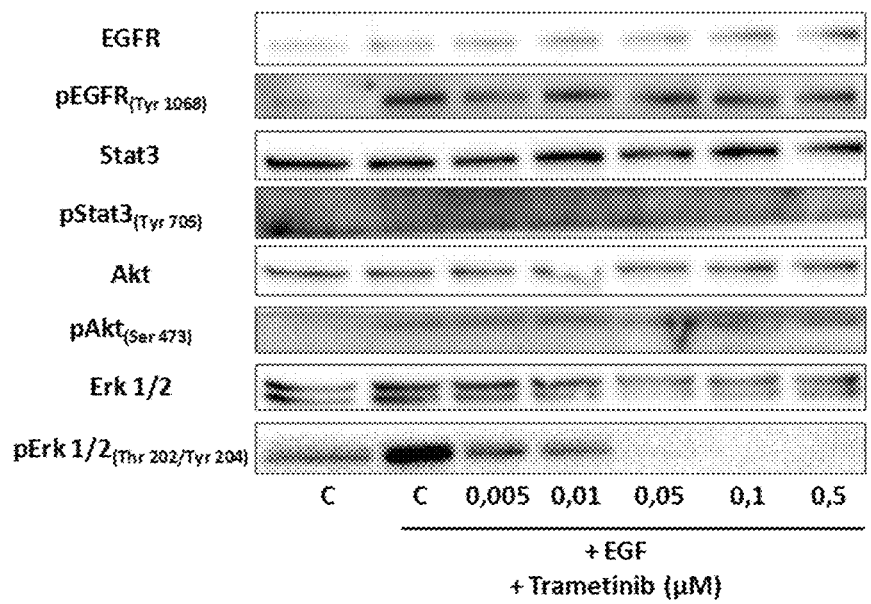
FIG. 32 shows the effect on pEGFR (TYR 1068), pSTAT3 (TYR 705), pAKT (SER 473), and pERK1/2 (THR 202/TYR 204) in response to 2 hour incubation with Trametinib in HT29 cells.
Figure 33:
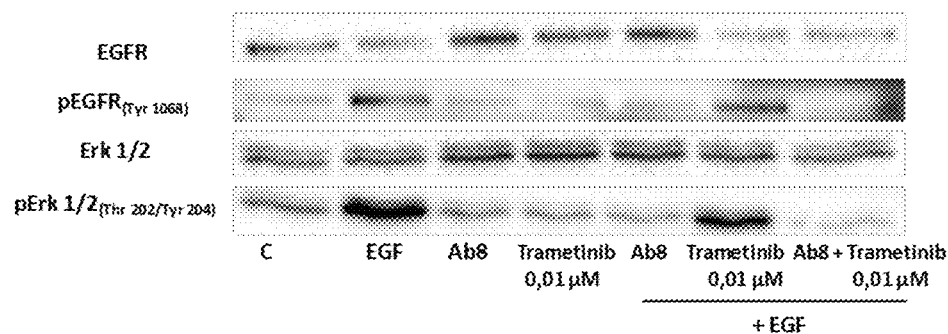
FIG. 33 shows the effect on pEGFR (TYR 1068) and pERK1/2 (THR 202/TYR 204) in response to 2 hour incubation with BVN22E antibodies in combination with Trametinib in HT29 cells.

In order to understand the effects of BVN22E antibodies and Trametinib on HT29 cell signaling, a western blot was carried out after a 2-hour incubation in HT29 cells. The BVN22E antibody was used at a 1/10 dilution. The results of the western blots (FIGS. 32 and 33) show that the combination of Trametinib and BVN22E antibodies enhanced inhibition of the pEGFR and pERK1/2 induced by EGF. These results confirm the pronounced effect observed in cell proliferation assays of the significant combinatorial effect of BVN22E antibodies and Trametinib in HT29 cells.

Figure 34:
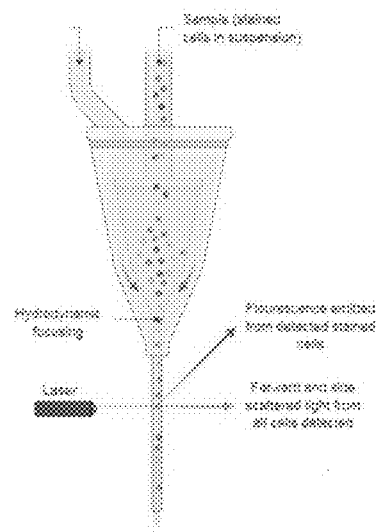
FIG. 34 illustrates a schematic that demonstrates the use of propium iodide staining to determine the cell cycle and apoptosis state of individual cells with flow cytometry. This method was applied to KRAS mutant (A549 and DLD1) and ALK translocated (H2228 and H3122) cell lines.

Propidium iodide staining was used to determine the cell cycle and apoptosis state of individual cells with flow cytometry, see FIG. 34. This method was applied to KRAS mutant (A549 and DLD1) and ALK translocated (H2228 and H3122) cell lines.

Figure 35:
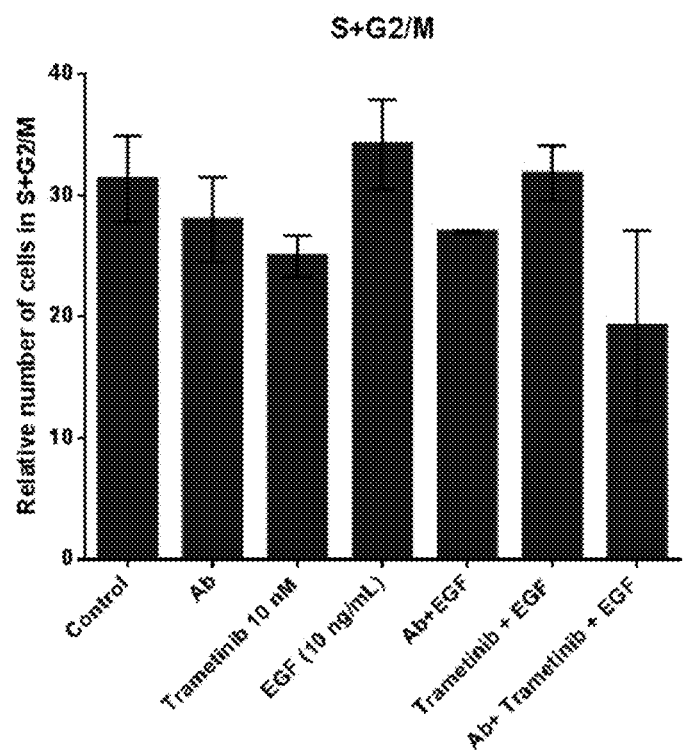
FIG. 35 shows the effect of BVN22E antibodies in combination with Trametinib on the relative number of cells in the S and G2M stages of the cell cycle in DLD1 cells.
Figure 36:
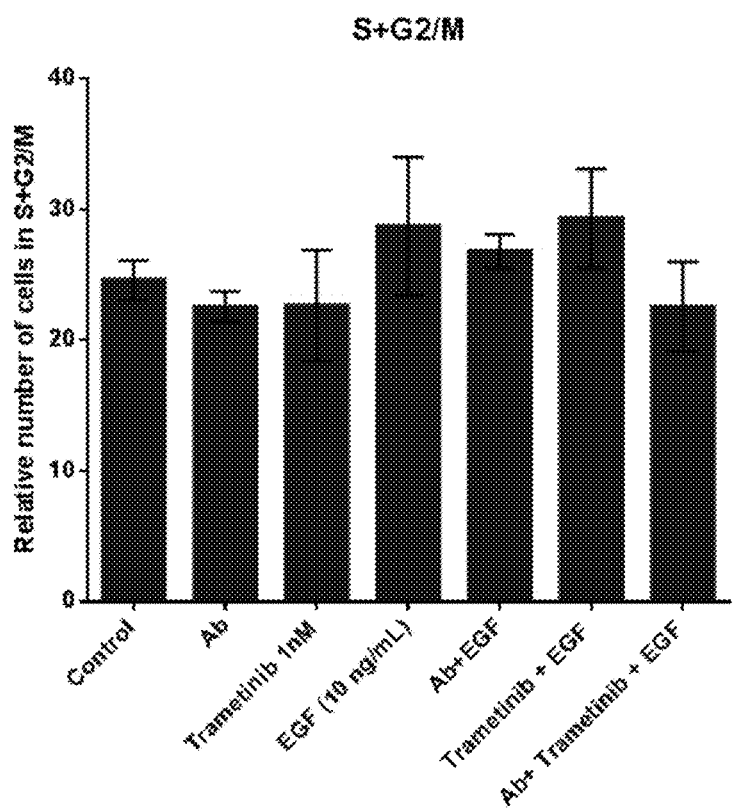
FIG. 36 shows the effect of BVN22E antibodies in combination with Trametinib on the relative number of cells in the S and G2M stages of the cell cycle in A549 cells.
Figure 37:
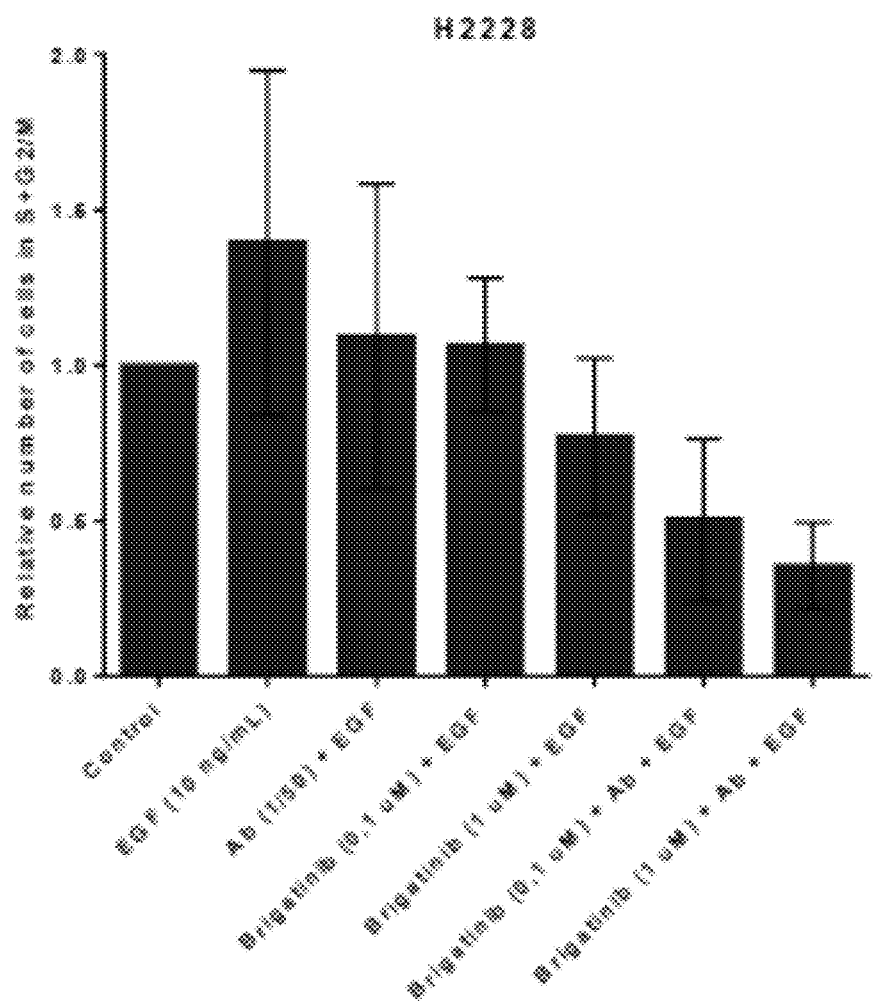
FIG. 37 shows the effect of BVN22E antibodies in combination with Brigatinib on the relative number of cells in the S and G2M stages of the cell cycle in H2228 cells.
Figure 38:
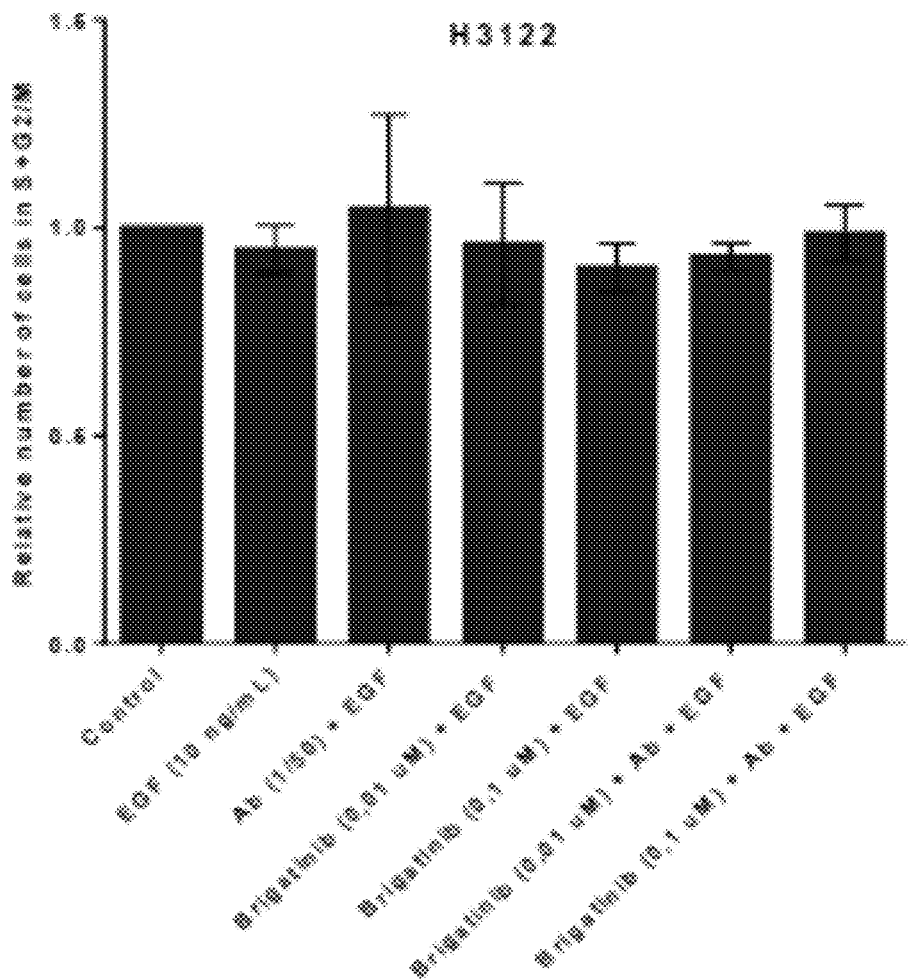
FIG. 38 shows the effect of BVN22E antibodies in combination with Brigatinib on the relative number of cells in the S and G2M stages of the cell cycle in H3122 cells.

In DLD1 cells, EGF alone induced a significantly higher percentage of S and G2/M state cells than did BVN22E antibodies with EGF or BVN22E antibodies with EGF in combination with Trametinib, see FIG. 35. In A549 cells very little difference was observed in cell cycle state with BVN22E antibodies with EGF in combination with Trametinib, see FIG. 36. In contrast, In H228 cells, there was a significant decrease in S and G2/M cells with BVN22E antibodies with EGF in combination with Trametinib relative to either BVN22E antibodies alone or Trametinib alone, see FIG. 37. In H3122 cells very little difference was observed in cell cycle state, see FIG. 38. These data indicate that BVN22E antibodies in combination with TKI inhibitors potentially suppress cell cycle progression regulated by EGF.

Four cell lines with KRAS mutations are shown in FIG. 39. A549 is a lung adenocarcinoma line that harbors a G12S mutation. H23 is a lung adenocarcinoma line that harbors a G12C mutation. DLD1 is a colon adenocarcinoma line that harbors a G13D mutation. LS174T is a colon adenocarcinoma line that also harbors a G12C mutation.

Figure 40:
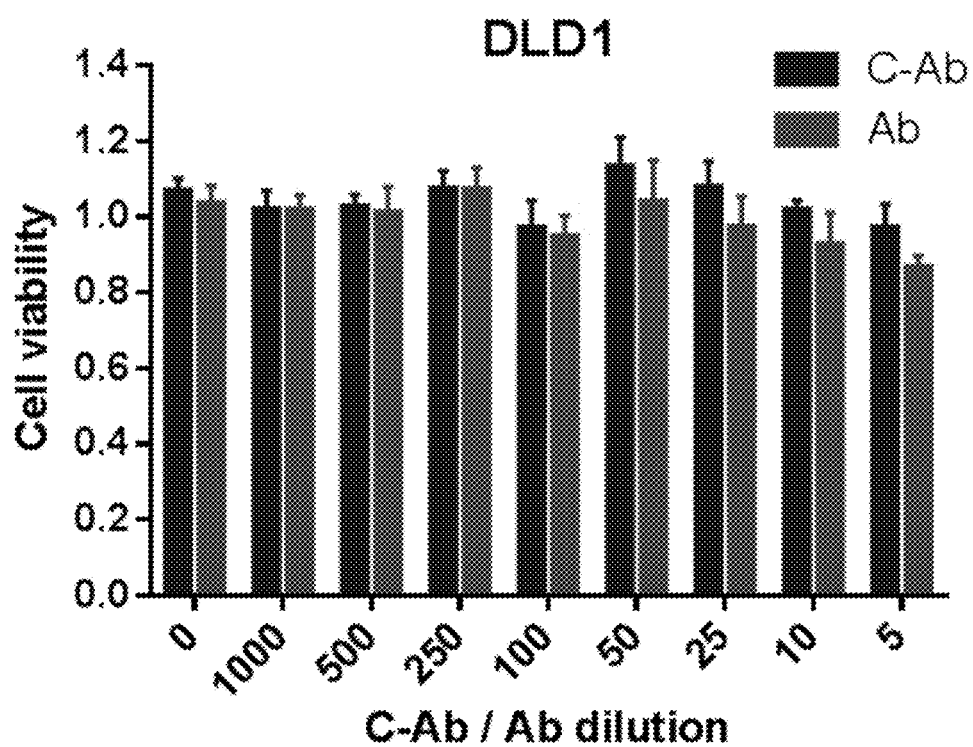
FIG. 40 shows the effect on cell viability of BVN22E antibodies in DLD1 cells.
Figure 41:
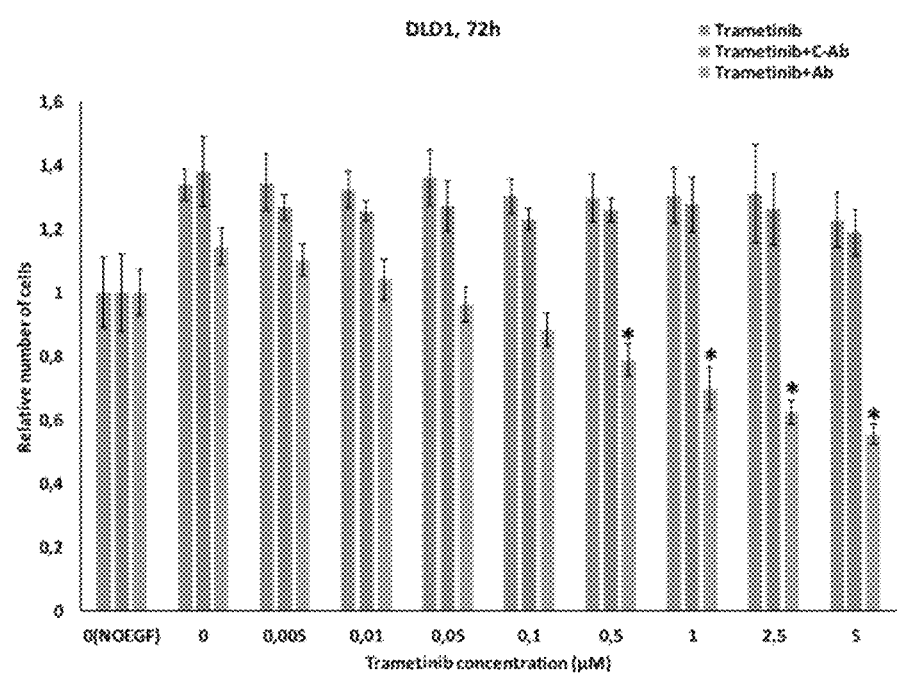
FIG. 41 shows the effect on cell viability of BVN22E antibodies in combination with Trametinib after 72 hour incubation in DLD1 cells.

The effects of BVN22E antibodies alone were next assessed in the DLD1 cell line. Higher concentrations of BVN22E antibodies significantly inhibited DLD1 cell viability relative to the control antibody, see FIG. 40. Similarly, Trametinib in combination with BVN22E antibodies induced significantly greater inhibition of cell viability than did Trametinib alone in DLD1 cells, see FIG. 41.

Figure 42:
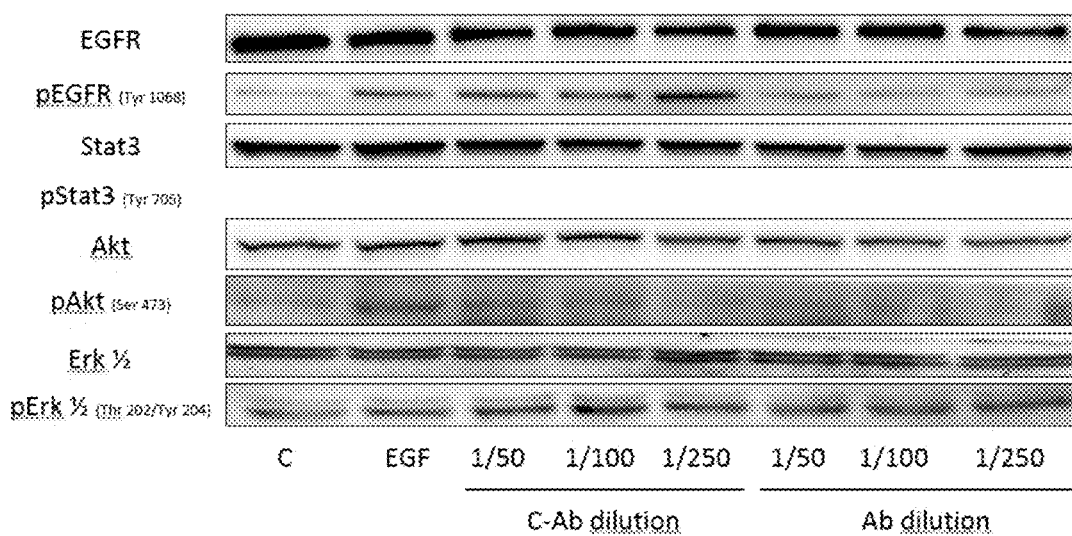
FIG. 42 shows the effect on pEGFR (TYR 1068), pSTAT3 (TYR 705), pAKT (SER 473), and pERK1/2 (THR 202/TYR 204) in response to 2 hour incubation of BVN22E antibodies in DLD1 cells.
Figure 43:
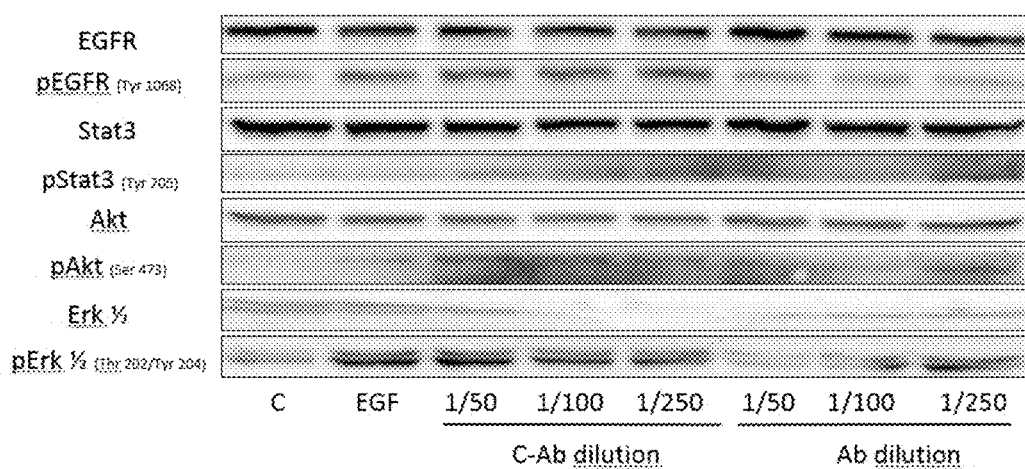
FIG. 43 shows the effect on pEGFR (TYR 1068), pSTAT3 (TYR 705), pAKT (SER 473), and pERK1/2 (THR 202/TYR 204) in response to 24 hour incubation of BVN22E antibodies in DLD1 cells.

The effects of BVN22E antibodies were investigated in DLD1 cells via Western Blots, see FIGS. 42 and 43. BVN22E antibodies alone had a limited effect in the DLD1 cell line. As expected, and at all dilutions tested, EGFR phosphorylation was strongly inhibited. Phosphorylation of AKT was only marginally inhibited and no effect was seen on the activation of ERK1/2.

Figure 44:
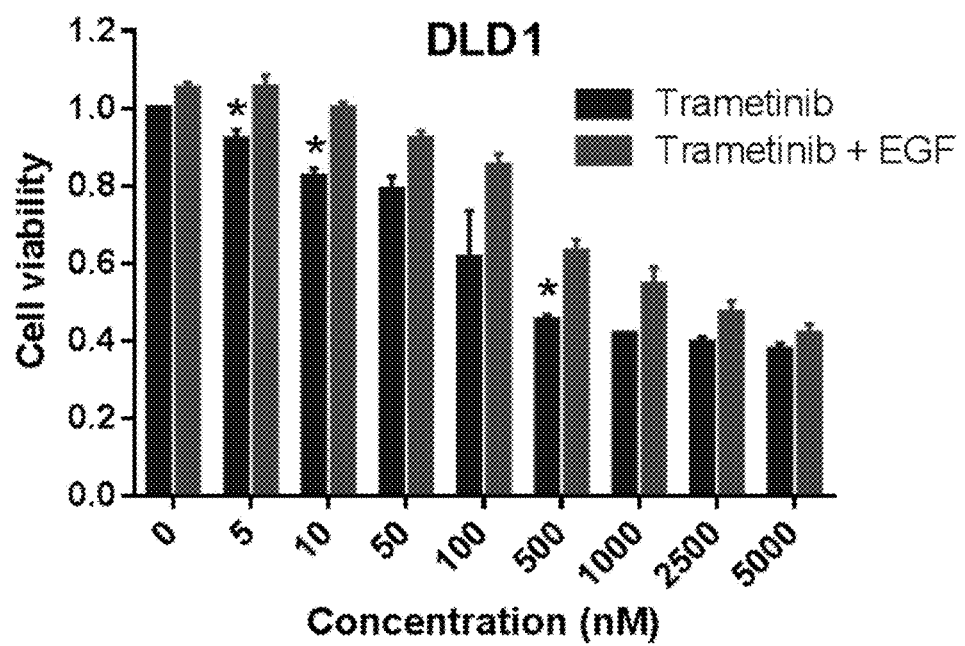
FIG. 44 shows the effect on cell viability of Trametinib in the presence and absence of EGF in DLD1 cells.

For all concentrations of Trametinib tested, cell viability was enhanced in the presence of EGF compared to Trametinib alone. Higher cell viability is indicative of tumor cell replication, a process Trametinib is intended to inhibit, thus the efficacy of Trametinib was lower in the presence of EGF, see FIG. 44.

Figure 45:
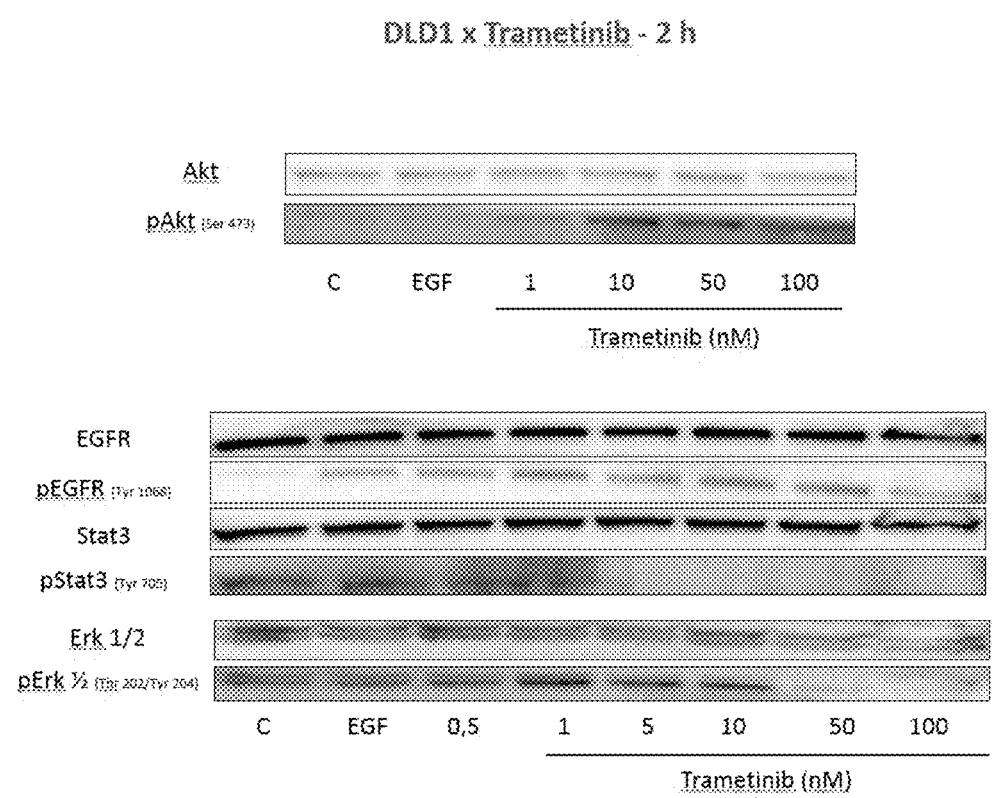
FIG. 45 shows the effect on pEGFR (TYR 1068), pSTAT3 (TYR 705), pAKT (SER 473), and pERK1/2 (THR 202/TYR 204) in response to 2 hour incubation of Trametinib in DLD1 cells.

The effect of Trametinib treatment in the DLD1 cell line was also assessed in a western blot assay and the results are presented in FIG. 45. There was no effect on pEGFR, nor any effect on pAKT. Inhibition of pStat3 and pERK1/2 were observed, though only at concentrations beyond the physiological concentrations of Trametinib used in patients.

Figure 46:
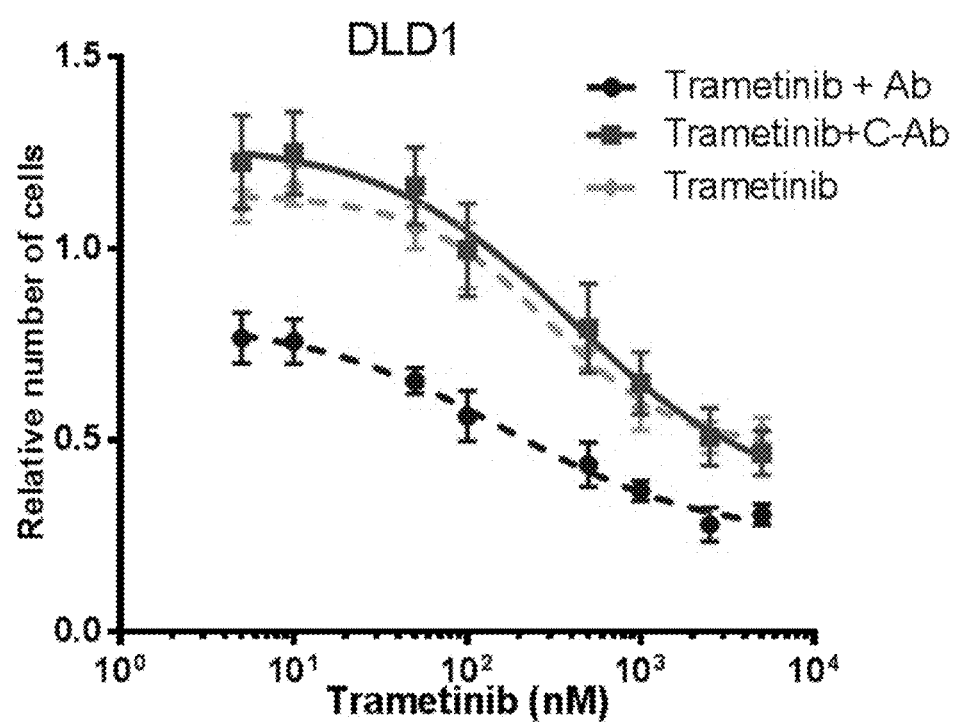
FIG. 46 shows the effect on cell viability of BVN22E antibodies in combination with Trametinib in DLD1 cells.

Next the combination of BVN22E antibodies in combination with Trametinib were investigated in the DLD1 cell line, as shown in FIG. 46. Cell viability with Trametinib in combination with BVN22E antibodies was significantly lower than with Trametinib alone or in combination with the control antibody. These results demonstrated that inhibiting EGF with BVN22E antibodies significantly strengthened the effect of Trametinib.

Figure 47:
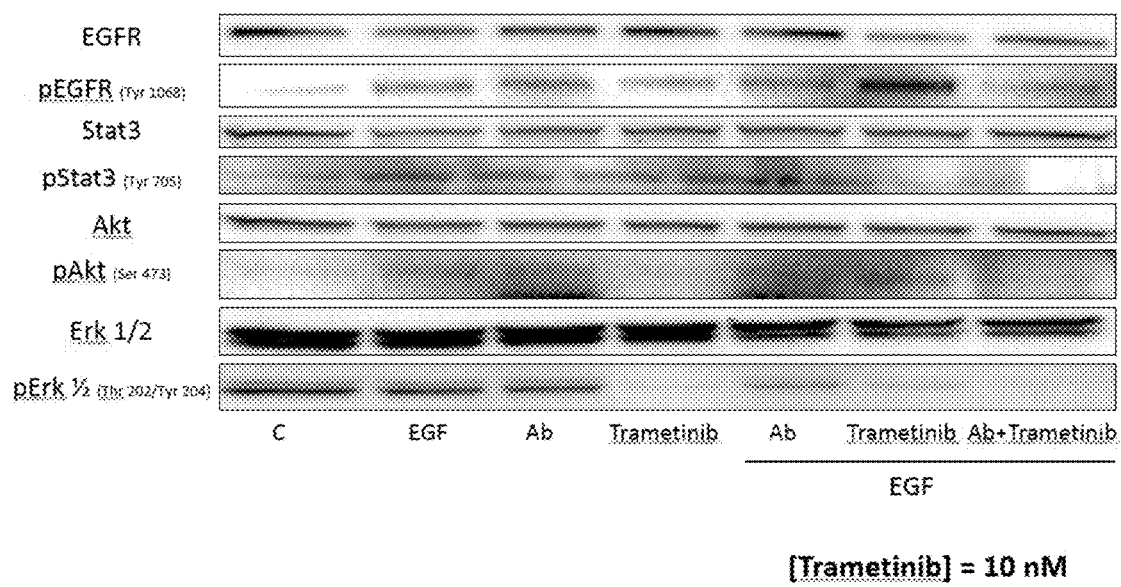
FIG. 47 shows the effect on pEGFR (TYR 1068), pSTAT3 (TYR 705), pAKT (SER 473), and pERK1/2 (THR 202/TYR 204) in response to 2 hour incubation of BVN22E antibodies in combination with Trametinib, in the presence and absence of EGF, in DLD1 cells.
Figure 48:
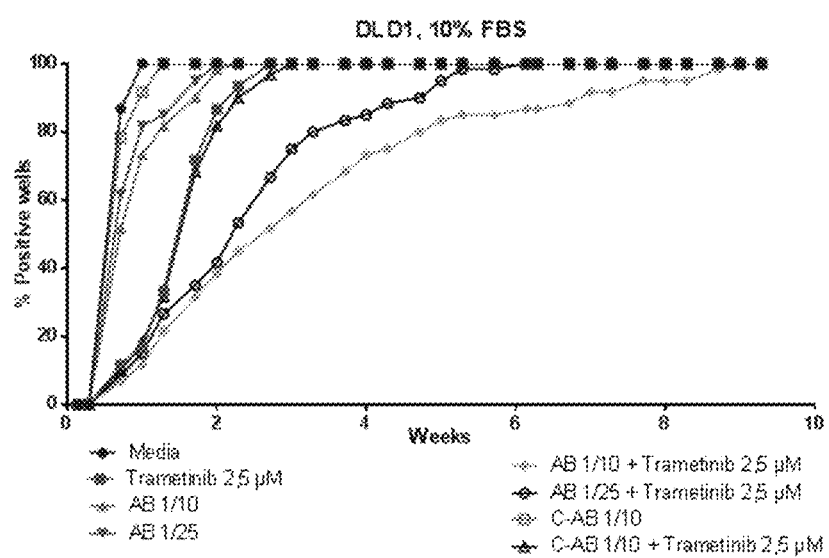
FIG. 48 shows the effect of BVN22E antibodies on the onset of resistance to Trametinib in DLD1 cells.

To understand the mechanism behind the strengthened effect of Trametinib in combination with BVN22E antibodies, a western blot experiment was conducted in the DLD1 cell line, as shown in FIG. 47. Treatment with Trametinib alone did not affect the signaling molecules assayed, apart from inhibition of pERK1/2. BVN22E antibodies alone inhibited phosphorylation of EGFR. Notably, the combination of BVN22E antibodies with Trametinib had a greater effect on inhibition of signaling than did either treatment individually. In combination, BVN22E antibodies with Trametinib inhibited pSTAT3 and pAKT, in addition to pERK1/2 and pEGFR. Further, onset of resistance to Trametinib was delayed in the combination of BVN22E antibodies in the presence of Trametinib relative to Trametinib alone, see FIG. 48.

In conclusion, addition of the BVN22E antibodies enhanced the anti-proliferative effect of Trametinib in the DLD1 KRAS mutated cell line. The effect of Trametinib alone on cell viability was significantly inhibited by presence of EGF. Treatment with Trametinib alone did not affect the signaling molecules assayed, apart from inhibition pERK1/2. BVN22E antibodies alone inhibited phosphorylation of EGFR. Notably, the combination of BVN22E antibodies with Trametinib had a greater effect on inhibition of signaling than did either treatment individually in DLD1 cells. The combination of BVN22E antibodies with Trametinib inhibited pSTAT3 and pAKT, in addition to pERK1/2 and pEGFR.

Figure 49:
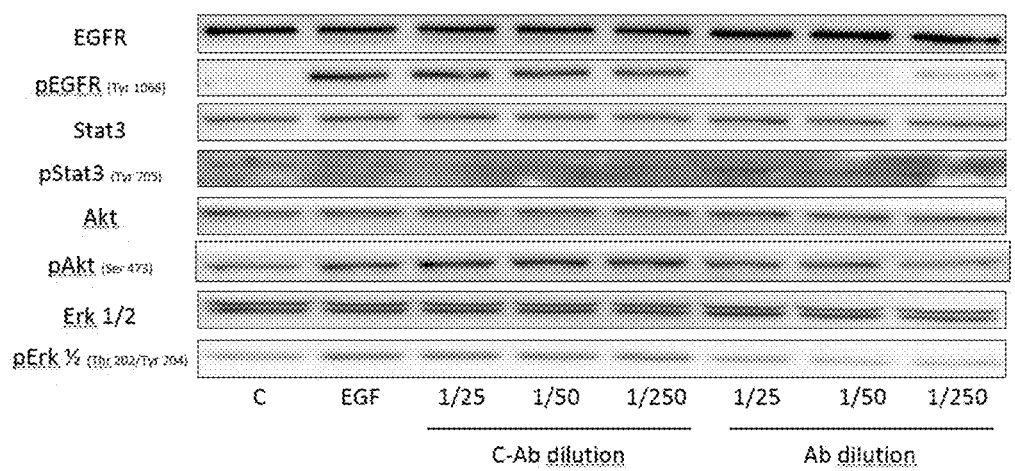
FIG. 49 shows the effect on cell viability of BVN22E antibodies in the A549 cell line.
Figure 50:
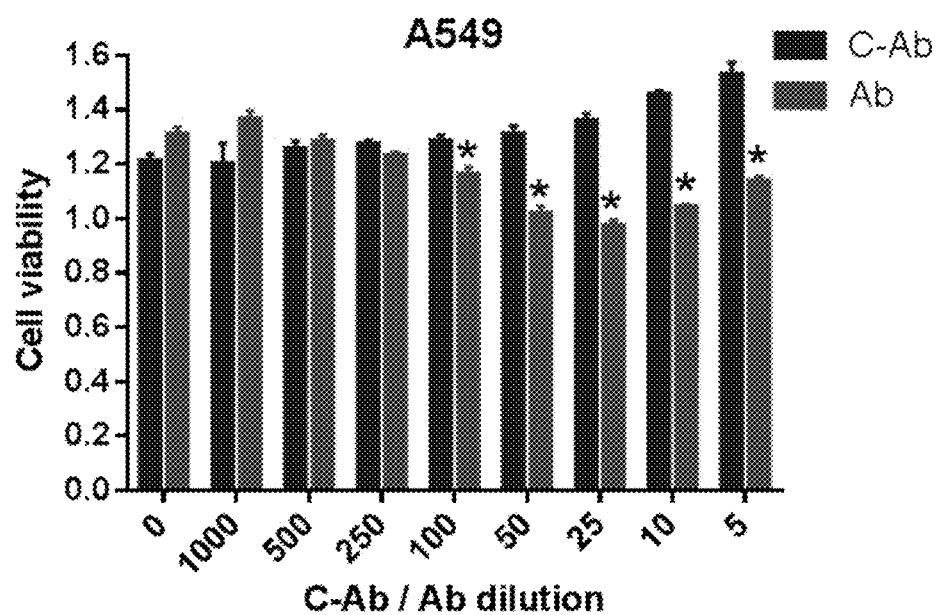
FIG. 50 shows the effect on pEGFR (TYR 1068), pSTAT3 (TYR 705), pAKT (SER 473), and pERK1/2 (THR 202/TYR 204) in response to 2 hour incubation with BVN22E antibodies in A549 cells.
Figure 51:
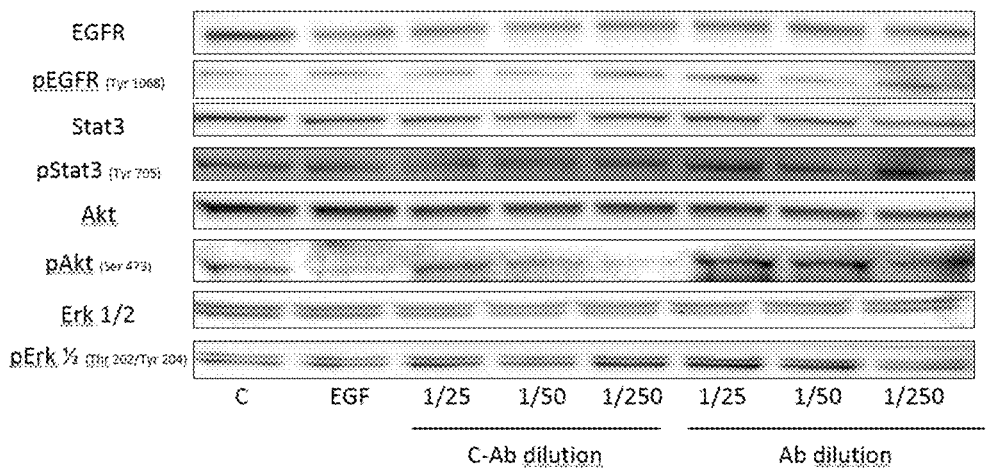
FIG. 51 shows the effect on pEGFR (TYR 1068), pSTAT3 (TYR 705), pAKT (SER 473), and pERK1/2 (THR 202/TYR 204) in response to 24 hour incubation with BVN22E antibodies in A549 cells.
Figure 52:
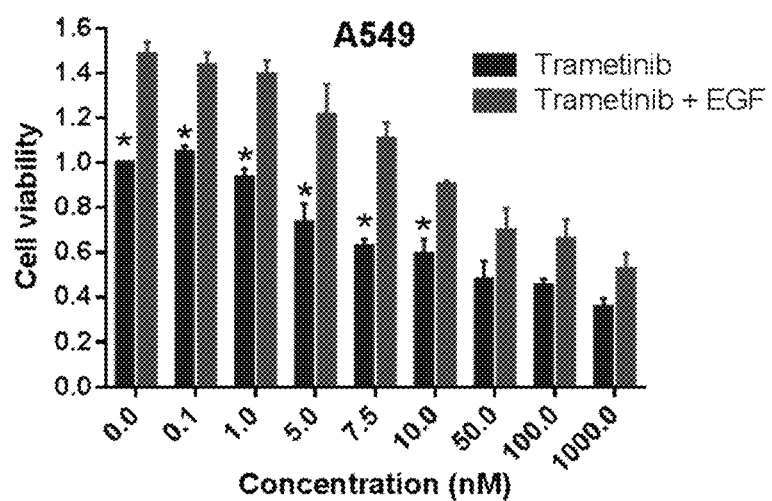
FIG. 52 shows the effect on cell viability of Trametinib in the presence and absence of EGF in the A549 cell line.
Figure 53:
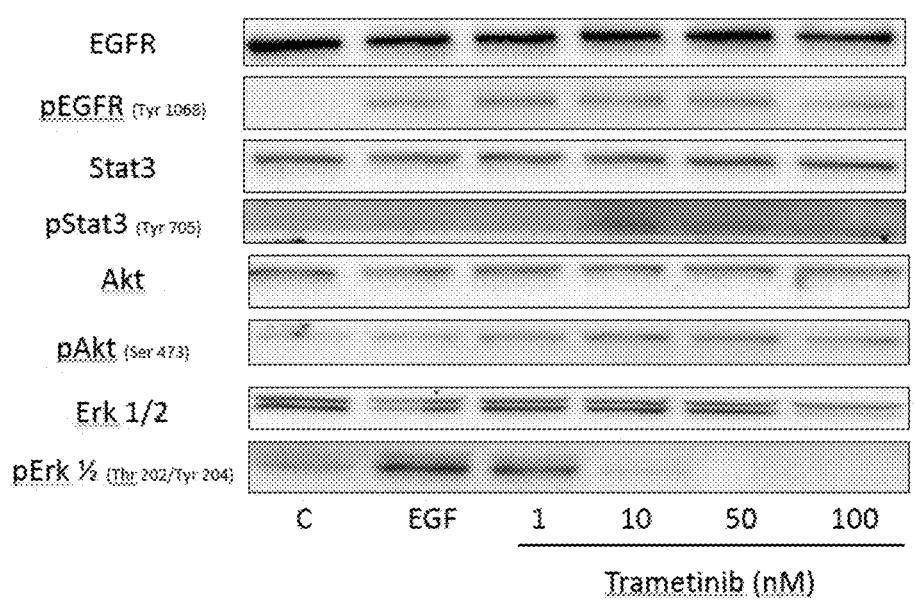
FIG. 53 shows the effect on pEGFR (TYR 1068), pSTAT3 (TYR 705), pAKT (SER 473), and pERK1/2 (THR 202/TYR 204) in response to 2 hour incubation of Trametinib in A549 cells.
Figure 54:
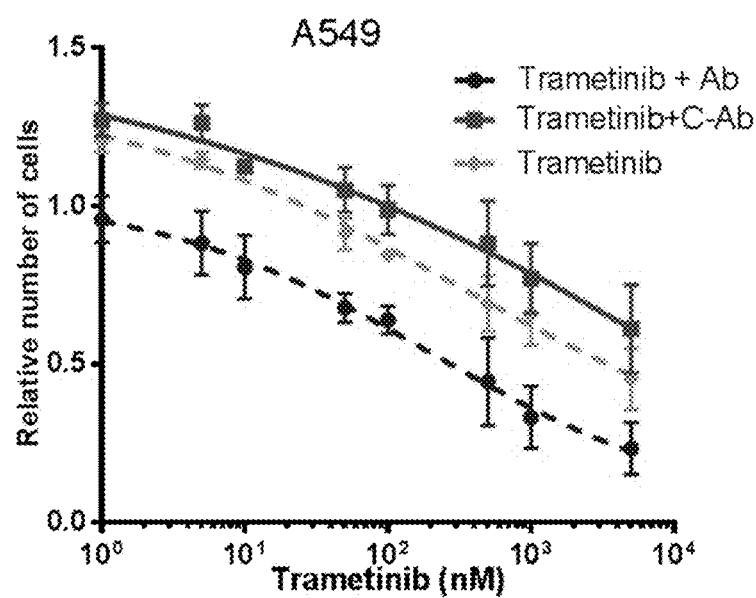
FIG. 54 shows the effect on cell viability of BVN22E antibodies in combination with Trametinib in A549 cells.

BVN22E antibodies at higher concentrations inhibited cell viability of the A549 cell line, as shown in FIG. 49. The effect on pEGFR (TYR 1068), pSTAT3 (TYR 705), pAKT (SER 473), and pERK1/2 (THR 202/TYR 204) in response to 2 hour incubation with BVN22E antibodies in A549 cells is shown in FIG. 50. Slight inhibition of pERK1/2 was observed, and complete inhibition of the activation of pEGFR by EGF was observed. The effect on pEGFR (TYR 1068), pSTAT3 (TYR 705), pAKT (SER 473), and pERK1/2 (THR 202/TYR 204) in response to 24 hour incubation with BVN22E antibodies in A549 cells is shown in FIG. 51; at 24 hours the effects on cell signaling were diminished in this cell line. The effect on cell viability of Trametinib in the presence and absence of EGF in the A549 cell line is shown in FIG. 52, EGF significantly enhanced cell viability. The effect on pEGFR (TYR 1068), pSTAT3 (TYR 705), pAKT (SER 473), and pERK1/2 (THR 202/TYR 204) in response to 2 hour incubation of Trametinib alone in A549 cells is shown in FIG. 53; completely inhibition of pERK1/2 is observed at this early time point. FIG. 54 shows that although there was a significant decrease in cell viability with BVN22E antibodies in combination with Trametinib in A549 cells, the decrease was lower relative to other cell types presented in the instant disclosure.

Figure 55:
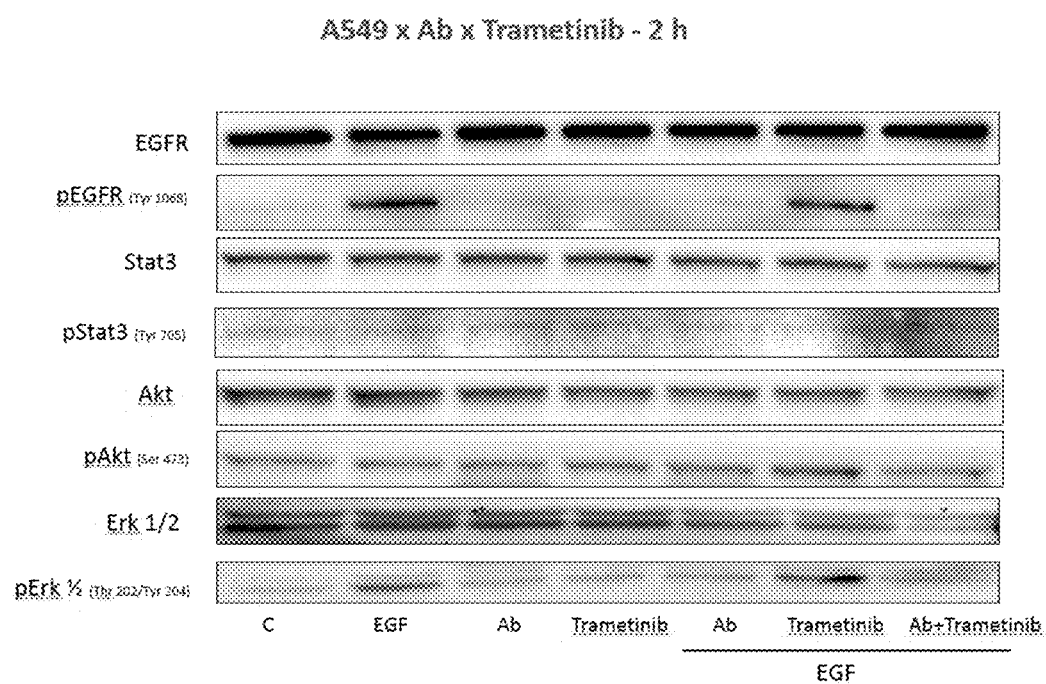
FIG. 55 shows the effect on pEGFR (TYR 1068), pSTAT3 (TYR 705), pAKT (SER 473), and pERK1/2 (THR 202/TYR 204) in response to 2 hour incubation of BVN22E antibodies in combination with Trametinib, also in the presence and absence of EGF, in A549 cells.

The effect on pEGFR (TYR 1068), pSTAT3 (TYR 705), pAKT (SER 473), and pERK1/2 (THR 202/TYR 204) in response to BVN22E antibodies in combination with Trametinib, in the presence and absence of EGF, in A549 cells was observed after 2 hour incubation. The strongest effect on pEGFR and pERK1/2 signaling in the presence of EGF was seen with BVN22E antibodies alone or in combination with Trametinib, see FIG. 55.

Figure 56:
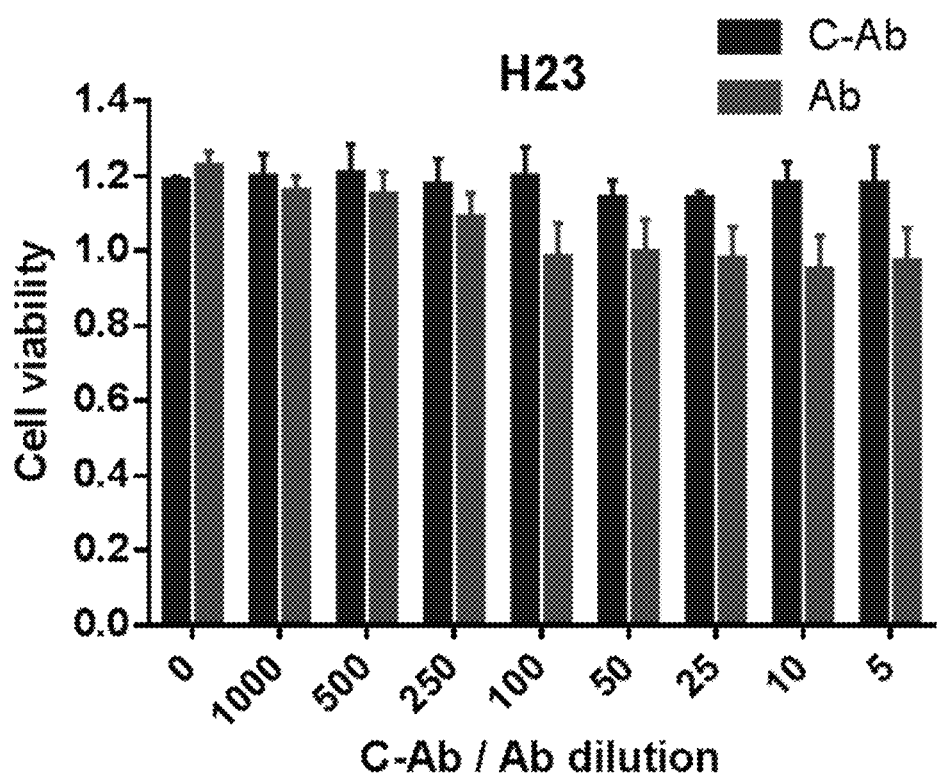
FIG. 56 shows the effect on cell viability of BVN22E antibodies in H23 cells.
Figure 57:
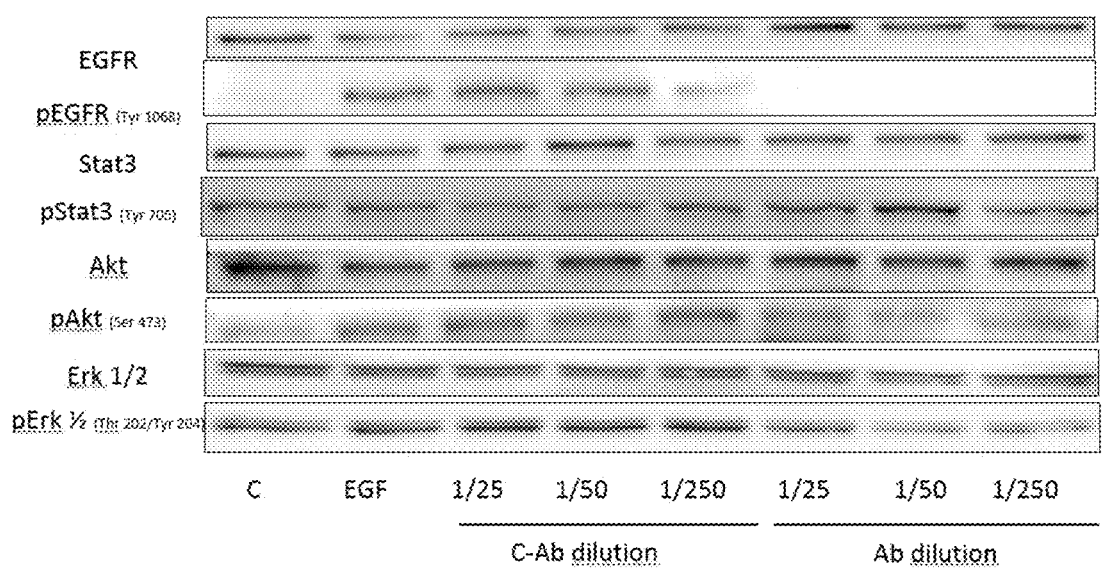
FIG. 57 shows the effect on pEGFR (TYR 1068), pSTAT3 (TYR 705), pAKT (SER 473), and pERK1/2 (THR 202/TYR 204) in response to 2 hour incubation of BVN22E antibodies in H23 cells.
Figure 58:
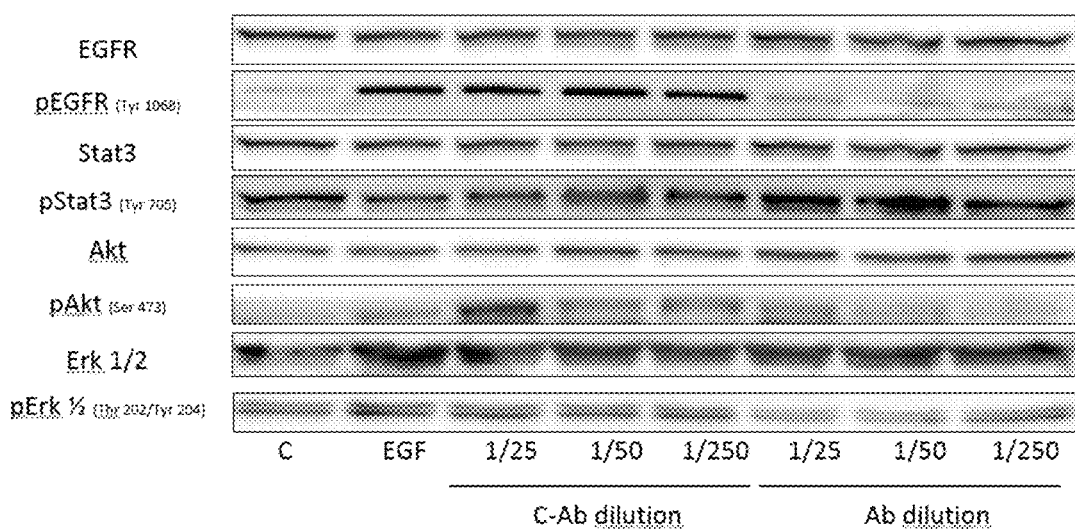
FIG. 58 shows the effect on pEGFR (TYR 1068), pSTAT3 (TYR 705), pAKT (SER 473), and pERK1/2 (THR 202/TYR 204) in response to 24 hour incubation of BVN22E antibodies in H23 cells.

BVN22E antibodies also significantly inhibited cell viability in H23 cells, see FIG. 56. The effect on pEGFR (TYR 1068), pSTAT3 (TYR 705), pAKT (SER 473), and pERK1/2 (THR 202/TYR 204) in response to 2 hour incubation of BVN22E antibodies in H23 cells was observed after 2 hour incubation, see FIG. 57. BVN22E antibodies completely abrogated the increase in pEGFR and pERK1/2 observed in response to EGF in H23 cells. This inhibition of pEGFR and pERK1/2 was maintained at 24 hours, as shown in FIG. 58.

Figure 59:
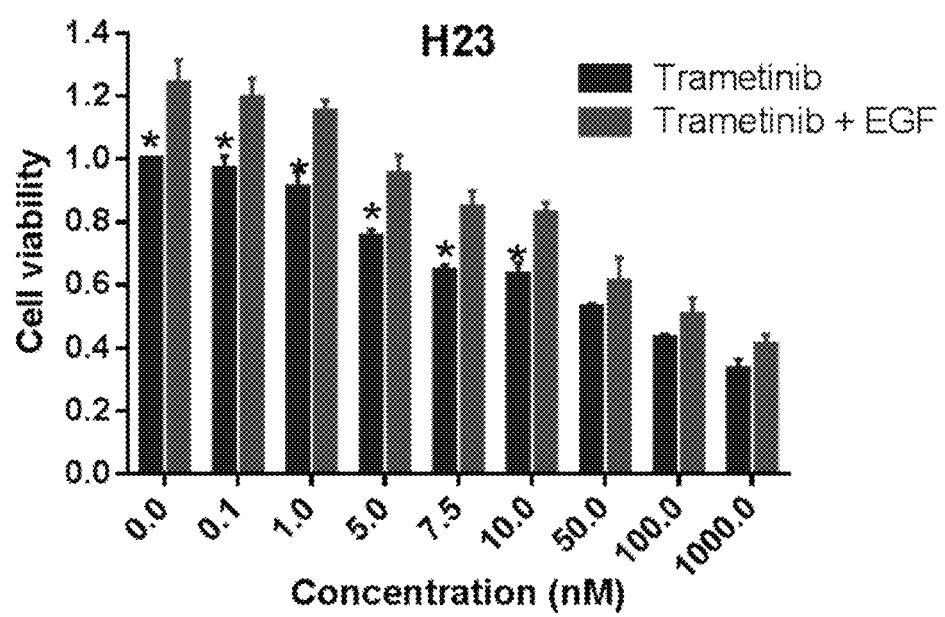
FIG. 59 shows the effect on cell viability of Trametinib in the presence and absence of EGF in H23 cells.
Figure 60:
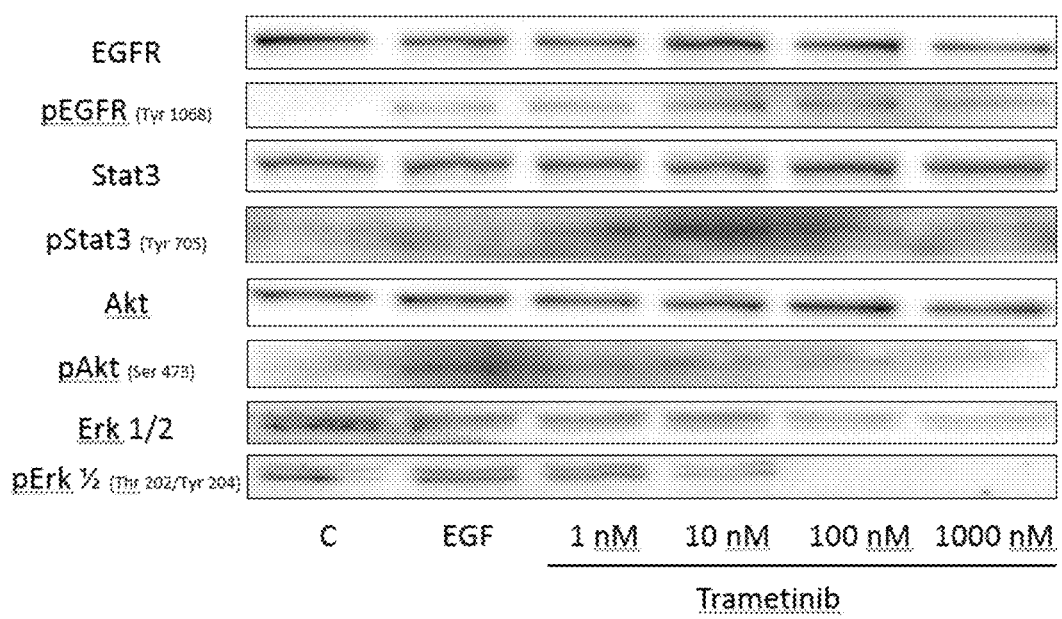
FIG. 60 shows the effect on pEGFR (TYR 1068), pSTAT3 (TYR 705), pAKT (SER 473), and pERK1/2 (THR 202/TYR 204) in response to 2 hour incubation of Trametinib in H23 cells.
Figure 61:
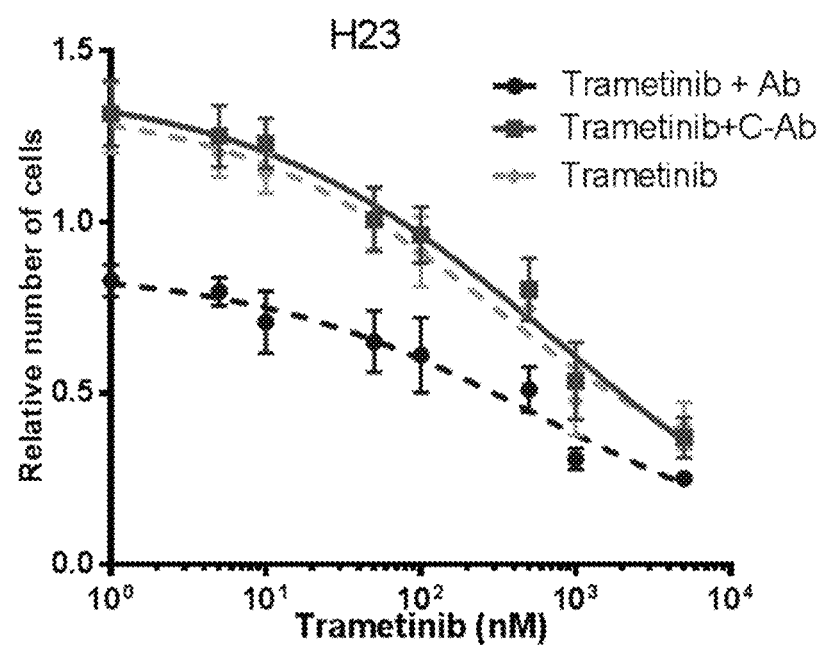
FIG. 61 shows the effect on cell viability of BVN22E antibodies in combination with Trametinib in H23 cells.
Figure 62:
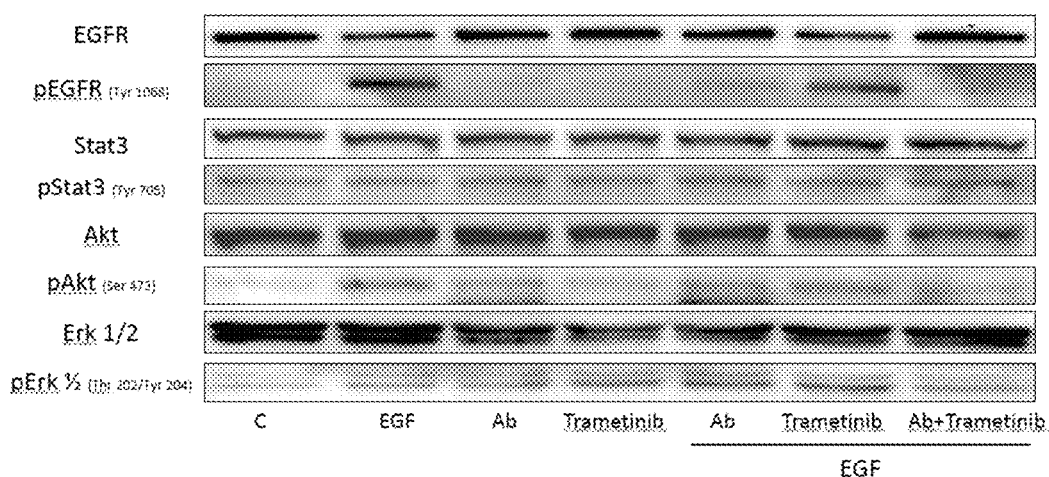
FIG. 62 shows the effects on pEGFR (TYR 1068), pSTAT3 (TYR 705), pAKT (SER 473), and pERK1/2 (THR 202/TYR 204) in response to 2 hour incubation of BVN22E antibodies in combination with Trametinib, in the presence and absence of EGF, in H23 cells.

Trametinib inhibition of cell viability was significantly inhibited by the presence of EGF in H23 cells, see FIG. 59. The effects of pEGFR (TYR 1068), pSTAT3 (TYR 705), pAKT (SER 473), and pERK1/2 (THR 202/TYR 204) in response to Trametinib in H23 cells were observed after 2 hour incubation. pERK1/2 was significantly inhibited at higher concentrations of Trametinib, see FIG. 60. BVN22E antibodies in combination with Trametinib significantly inhibited cell viability of H23 cells relative to Trametinib alone, see FIG. 61. In response to 2 hour incubation of BVN22E antibodies in combination with Trametinib in H23 cells, significant inhibition of pEGFR was observed.

Figure 63:
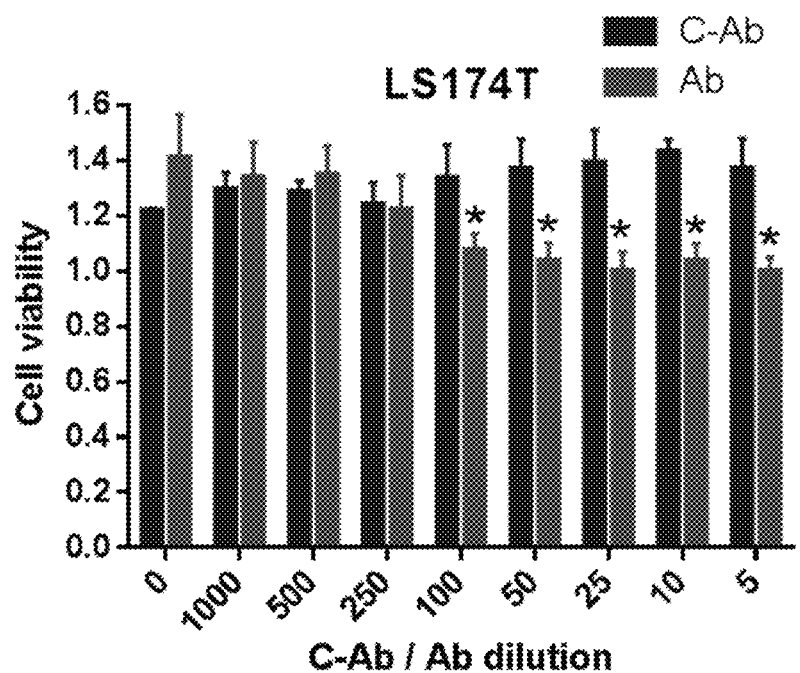
FIG. 63 shows the effect on cell viability of BVN22E antibodies in the LS174T cell line.
Figure 64:
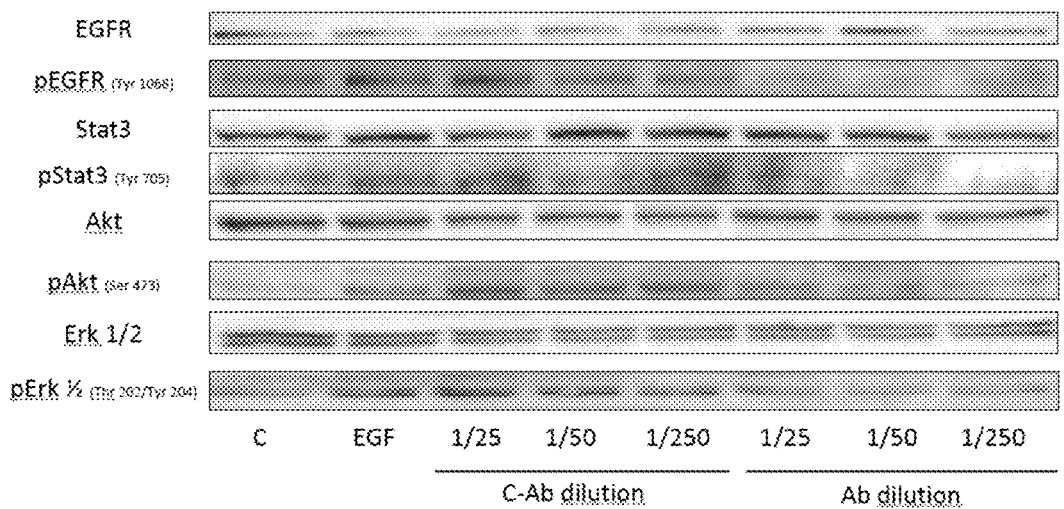
FIG. 64 shows the effect on pEGFR (TYR 1068), pSTAT3 (TYR 705), pAKT (SER 473), and pERK1/2 (THR 202/TYR 204) in response to 2 hour incubation of BVN22E antibodies in LS174T cells.
Figure 65:
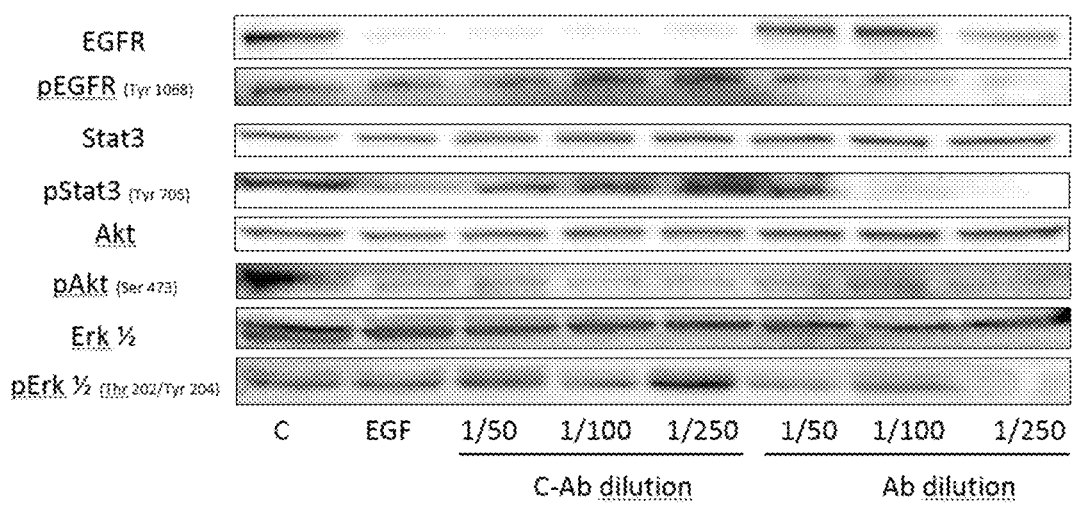
FIG. 65 shows the effect on pEGFR (TYR 1068), pSTAT3 (TYR 705), pAKT (SER 473), and pERK1/2 (THR 202/TYR 204) in response to 24 hour incubation of BVN22E antibodies in LS174T cells.
Figure 66:
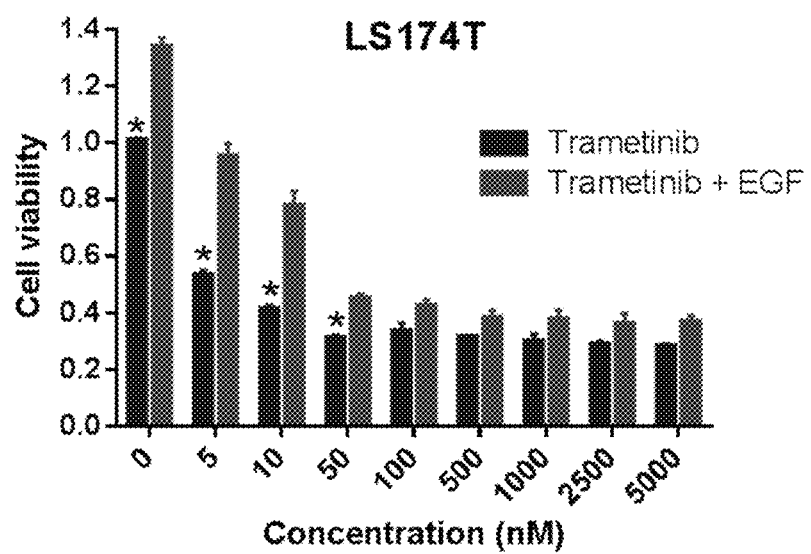
FIG. 66 shows the effect on cell viability of Trametinib, in the presence and absence of EGF in the LS174T cell line.
Figure 67:
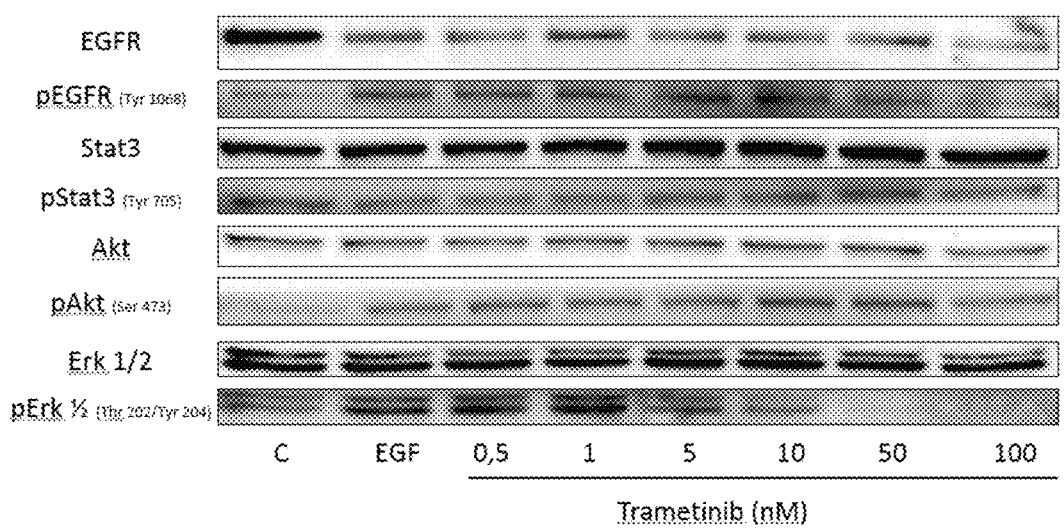
FIG. 67 shows the effect on pEGFR (TYR 1068), pSTAT3 (TYR 705), pAKT (SER 473), and pERK1/2 (THR 202/TYR 204) in response to 2 hour incubation of Trametinib in LS174T cells.
Figure 68:
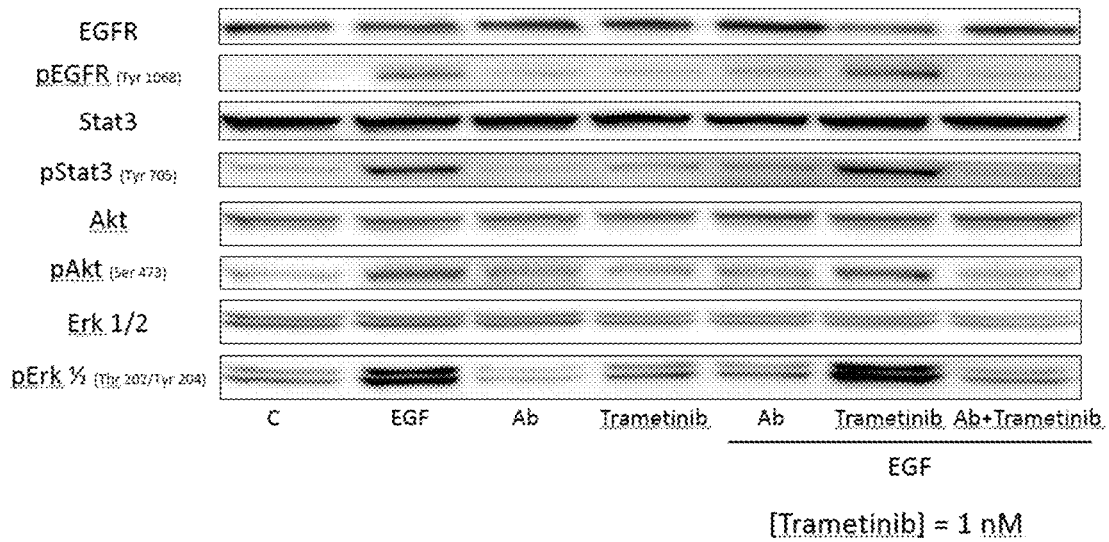
FIG. 68 shows the effect on pEGFR (TYR 1068), pSTAT3 (TYR 705), pAKT (SER 473), and pERK1/2 (THR 202/TYR 204) in response to 2 hour incubation of BVN22E antibodies in combination with Trametinib, in the presence and absence of EGF, in LS174T cells.

BVN22E antibodies significantly inhibited LS174T cell viability compared to the control antibody, see FIG. 63. BVN22E antibodies also inhibited both pEGFR and pAKT signaling in LS174T cells, see FIGS. 64 and 65. Trametinib alone inhibited LS174T cell proliferation, and this effect was diminished when EGF was present, see FIG. 66. The effect of Trametinib in the LS174T cell line was assessed in a 2 hour incubation western blot assay, see FIG. 67. Trametinib did not affect the phosphorylation of any of the molecules tested within the physiological range of between 1 to 10 nM. At higher concentrations, which are not clinically relevant, an effect on pERK1/2 was observed. However, Trametinib in combination with anti-BVN22E inhibited pAKT, pEGFR and pERK1/2 while also inhibiting pSTAT3, see FIG. 68. Thus, BVN22E antibodies broadened the effects of Trametinib on signaling inhibition.

Figure 69:
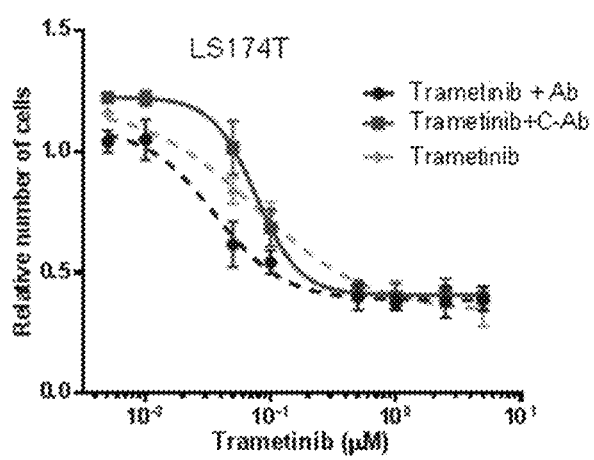
FIG. 69 shows the effect of Trametinib alone and in combination with BVN22E antibodies on LS174T cell viability.

The combination of BVN22E antibodies and Trametinib on LS174T cell viability was investigated. As seen in FIG. 69. BVN22E antibodies in combination with Trametinib significantly increased the effect on cell viability relative to Trametinib alone in the 1 to 10 nM range of Trametinib, i.e. the physiological level of Trametinib in patients. However, in comparison to the effect of the combination of BVN22E antibodies and Trametinib in DLD1 cells, the effect of the combination in LS174T cells was less pronounced.

In the LS174T KRAS mutated cell line, the BVN22E antibodies enhanced the anti-proliferative effect of Trametinib. The inhibitory effect of Trametinib on cell viability was significantly reduced by the presence of EGF. BVN22E antibodies alone inhibited both pEGFR and pAKT. However, Trametinib in combination with anti-BVN22E inhibited pAKT, pEGFR and pERK1/2 while also inhibiting pSTAT3. Thus, in both KRAS mutated cell lines, BVN22E antibodies enhanced the effect of Trametinib in inhibiting cell proliferation and broadened the effect of Trametinib on signaling inhibition.

Figure 70:
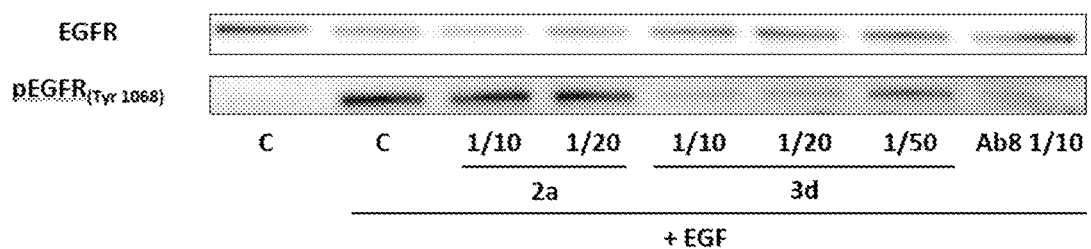
FIG. 70 shows the effect of human patient anti-EGF sera on pEGFR (TYR 1068) in SW900 cells in the presence of EGF.
Figure 71:
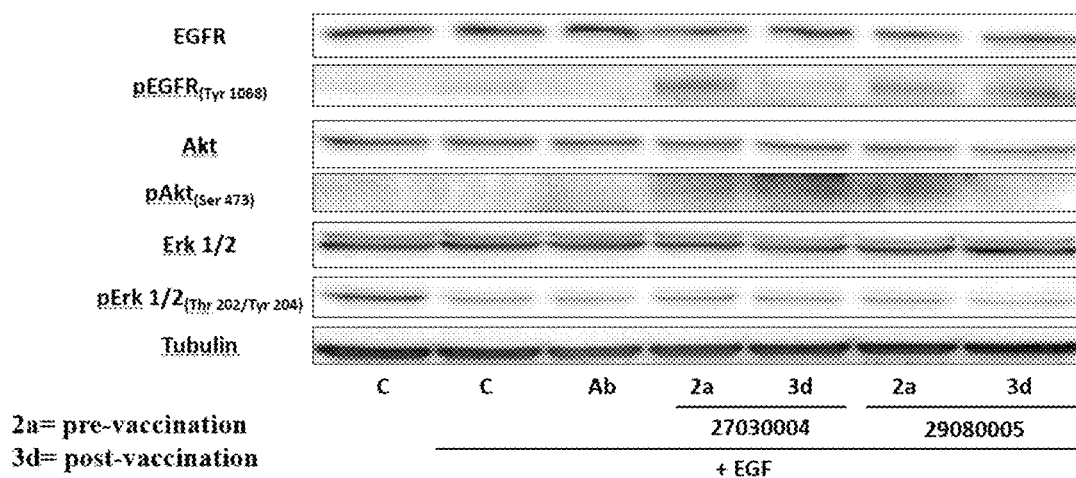
FIG. 71 shows the effect of two human patient anti-EGF sera on pEGFR (TYR 1068), pAKT (SER 473), and pERK1/2 (THR 202/TYR 204) in SW900 cells in the presence of EGF.
Figure 72:
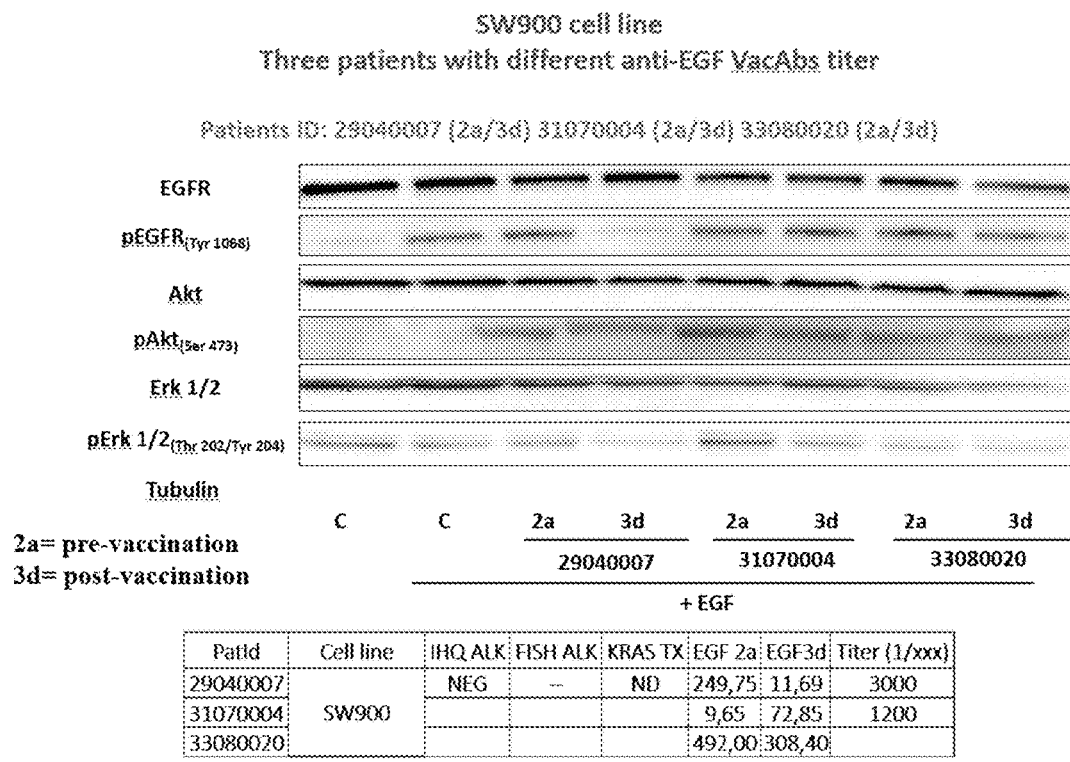
FIG. 72 shows the effect of three human patient anti-EGF sera on pEGFR (TYR 1068), pAKT (SER 473), and pERK1/2 (THR 202/TYR 204) in SW900 cells in the presence of EGF.
Figures 73A, 73B:
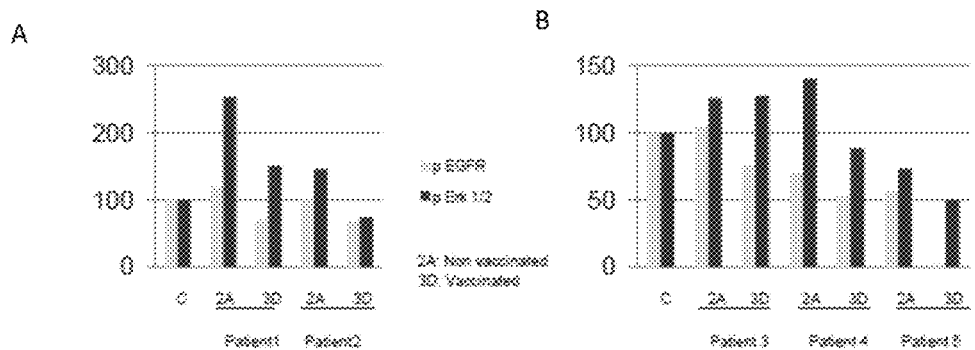
FIGS. 73A-B show a summary of the quantification of the Western Blots from the patient anti-EGF sera shown in FIGS. 69-71.
Figure 74A:
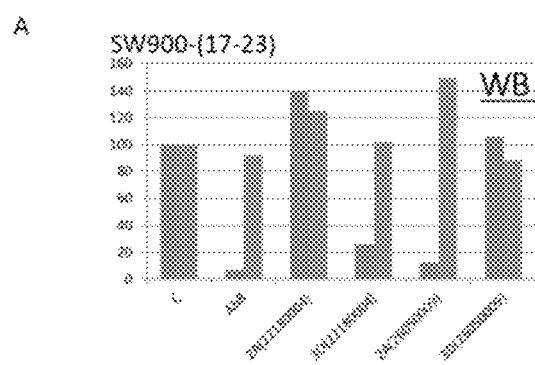
FIG. 74A-D show the quantification of the Western Blots from the patient anti-EGF sera in SW900 cells shown in FIGS. 69-71.
Figure 74B:
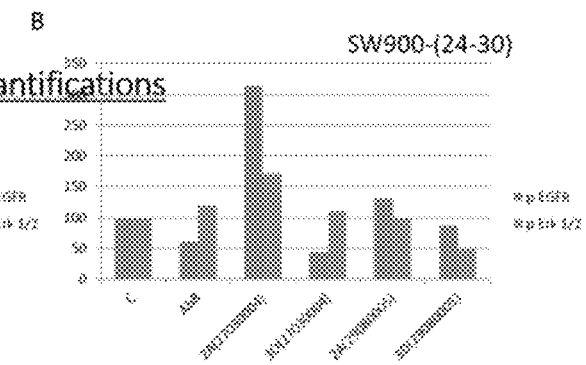
Figure 74C:
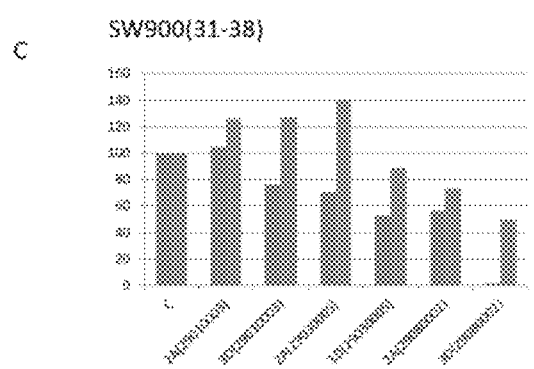
Figure 74D:
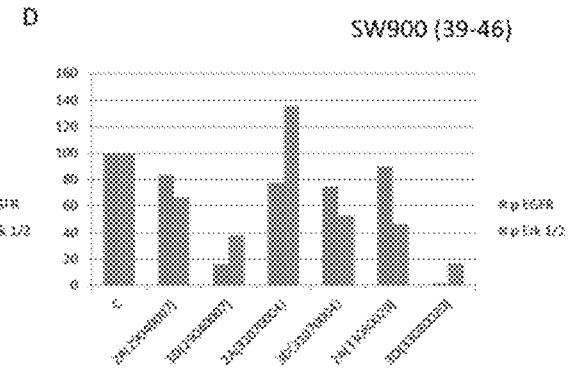

Example 3: Assessment of Sera from Patients Immunized with EGF Cancer Vaccine in SW900 Cells The effect of human patient (22180004) anti-EGF sera on pEGFR in SW900 wild type cells was observed in the presence of EGF. 2a=patient before vaccination, 3d=patient after vaccination. Complete inhibition of pEGFR activation was observed in the presence of anti-EGF sera, and some decrease in pERK1/2 was also observed, see FIG. 70. The effect of human patient anti-EGF sera from two additional patients on pEGFR in SW900 wild type cells was observed in the presence of EGF, see FIG. 71. Significant inhibition of pEGFR and pERK1/2 activation were observed in patient 27030004, while a lesser inhibition of both was observed in patient 29080005. The results of anti-EGF sera from three additional patients are shown in FIG. 72. For two of the patients (29040007 and 33080020), a significant inhibition of pEGFR and pERK1/2 signaling was observed. For patient 31070004, a minimal change was observed. The results of FIGS. 70-72 are summarized in FIGS. 73 and 74.

REFERENCES

1. Gandhi J, Zhang J, Xie Y, et al. Alterations in genes of the EGFR signaling pathway and their relationship to EGFR tyrosine kinase inhibitor sensitivity in lung cancer cell lines. *PLoS ONE*. 2009; 4:e4576.
2. Rosell R, Moran T, Queralt C, et al. Screening for epidermal growth factor receptor mutations in lung cancer. *N Engl J Med*. 2009; 361:958-967.
3. Rosell R, Carcereny E, Gervais R, et al. Erlotinib versus standard chemotherapy as first-line treatment for European patients with advanced EGFR mutation-positive non-small-cell lung cancer (EURTAC): a multi-centre, open-label, randomised phase 3 trial. *Lancet Oncol*. 2012; 13:239-246.
4. Mok T S, Wu Y L, Thongprasert S, et al. Gefitinib or carboplatin-paclitaxel in pulmonary adenocarcinoma. *N Engl J Med*. 2009; 361:947-957.
5. Maemondo M, Inoue A, Kobayashi K, et al. Gefitinib or chemotherapy for non-small-cell lung cancer with mutated EGFR. *N Engl J Med*. 2010; 362:2380-2388.
6. Bradley J D, Paulus R, Komaki R, et al. Standard-dose versus high-dose conformal radiotherapy with concurrent and consolidation carboplatin plus paclitaxel with or without cetuximab for patients with stage IIIA or IIIB non-small-cell lung cancer (RTOG 0617): a randomised, two-by-two factorial phase 3 study. *Lancet Oncol*. 2015; 16:187-199.
7. Lynch T J, Patel T, Dreisbach L, et al. Cetuximab and first-line taxane/carboplatin chemotherapy in advanced non-small-cell lung cancer: results of the randomized multicenter phase III trial BMS099. *J Clin Oncol*. 2010; 28:911-917.
8. Herbst R, Redman M, Kim E. A randomized, phase III study comparing carboplatin/paclitaxel or carboplatin/paclitaxel/bevacizumab with our without concurrent cetuximab in patients with advanced non-small cell lung cancer (NSCLC): SWOG S0819. Presented at the 2015 World Conference on Lung Cancer, Denver, Colorado.
9. Janjigian Y Y, Smit E F, Groen H J, et al. Dual inhibition of EGFR with afatinib and cetuximab in kinase inhibitor-resistant EGFR-mutant lung cancer with and without T790M mutations. *Cancer Discov*. 2014; 4:1036-1045.
10. Horn L, Gettinger S, Camidge D R, et al. Continued use of afatinib with the addition of cetuximab after progression on afatinib in patients with EGFR mutation-positive non-small-cell lung cancer and acquired resistance to gefiti-nib or erlotinib. *Lung Cancer*. 2017; 113:51-58.
11. Rodriguez P C, Popa X, Martinez O, et al. A phase III clinical trial of the epidermal growth factor vaccine CIMAvax-EGF as switch maintenance therapy in advanced non-small cell lung cancer patients. *Clin Cancer Res*. 2018; 22:3782-3790.

12. Rosell R, Neninger E, Nicolson M, et al. Pathway targeted immunotherapy: rationale and evidence of durable clinical responses with a novel, EGF-directed agent for advanced NSCLC. *J Thorac Oncol.* 2016; 11:1954-1961.
13. Jacobsen K, Bertran-Alamillo J, Molina M A, et al. Convergent Akt activation drives acquired EGFR inhibitor resistance in lung cancer. *Nat Commun.* 2017; 8:410.
14. Tricker E M, Xu C, Uddin S, et al. Combined EGFR/MEK inhibition prevents the emergence of resistance in EGFR-mutant lung cancer. *Cancer Discov.* 2015; 5:960-971.
15. Chaib I, Karachaliou N, Pilotto S, et al. Co-activation of STAT3 and YES-associated protein 1 (YAP1) pathway in EGFR-mutant NSCLC. *J Natl Cancer Inst.* 2017; 109(9).
16. Borghaei H, Paz-Ares L, Horn L, et al. Nivolumab versus docetaxel in advanced nonsquamous non-small-cell lung cancer. *N Engl J Med.* 2015; 373:1627-1639.
17. Herbst R S, Baas P, Kim D W, et al. Pembrolizumab versus docetaxel for previously treated, PD-L1-positive, advanced non-small-cell lung cancer (KEYNOTE-010): a randomised controlled trial. *Lancet.* 2016; 387:1540-1550.
18. Rittmeyer A, Barlesi F, Waterkamp D, et al. Atezolizumab versus docetaxel in patients with previously treated non-small-cell lung cancer (OAK): a phase 3, open-label, multicentre randomised controlled trial. *Lancet.* 2017; 389:255-265.
19. Lee C K, Man J, Lord S, et al. Checkpoint inhibitors in metastatic EGFR-mutated non-small cell lung cancer—a meta-analysis. *J Thorac Oncol.* 2017; 12:403-407.
20. Dong Z Y, Zhang J T, Liu S Y, et al. EGFR mutation correlates with uninflamed phenotype and weak immunogenicity, causing impaired response to PD-1 blockade in non-small cell lung cancer. *Oncoimmunology.* 2017; 6:e1356145.
21. Neninger Vinageras E, de la Torre A, Osorio Rodriguez M, et al. Phase II randomized controlled trial of an epidermal growth factor vaccine in advanced non-small-cell lung cancer. *J Clin Oncol.* 2008; 26:1452-1458.
22. Garcia B, Neninger E, de la Torre A, et al. Effective inhibition of the epidermal growth factor/epidermal growth factor receptor binding by anti-epidermal growth factor antibodies is related to better survival in advanced non-small-cell lung cancer patients treated with the epidermal growth factor cancer vaccine. *Clin Cancer Res.* 2008; 14:840-846.
23. Joh T, Itoh M, Katsumi K, et al. Physiological concentrations of human epidermal growth factor in biological fluids: use of a sensitive enzyme immunoassay. *Clin Chim Acta.* 1986; 158:81-90.
24. Wakeling A E, Guy S P, Woodburn J R, et al. ZD1839 (Ire-ssa): an orally active inhibitor of epidermal growth factor signaling with potential for cancer therapy. *Cancer Res.* 2002; 62:5749-5754.
25. Vollebergh M A, Kappers I, Klomp H M, et al. Ligands of epidermal growth factor receptor and the insulin-like growth factor family as serum biomarkers for response to epidermal growth factor receptor inhibitors in patients with advanced non-small cell lung cancer. *J Thorac Oncol.* 2010; 5:1939-1948.
26. Ishikawa N, Daigo Y, Takano A, et al. Increases of amphiregulin and transforming growth factor-alpha in serum as predictors of poor response to gefitinib among patients with advanced non-small cell lung cancers. *Cancer Res.* 2005; 65:9176-9184.
27. Romero-Ventosa E Y, Blanco-Prieto S, Gonzalez-Pineiro A L, et al. Pretreatment levels of the serum biomarkers CEA, CYFRA 21-1, SCC and the soluble EGFR and its ligands EGFTGF-alpha, HB-EGF in the prediction of outcome in erlo-tinib treated non-small-cell lung cancer patients. *Spring-erplus.* 2015; 4:171.
28. Perez-Torres M, Guix M, Gonzalez A, et al. Epidermal growth factor receptor (EGFR) antibody down-regulates mutant receptors and inhibits tumors expressing EGFR mutations. *J Biol Chem.* 2006; 281:40183-40192.
29. Mukohara T, Engelman J A, Hanna N H, et al. Differential effects of gefitinib and cetuximab on non-small-cell lung cancers bearing epidermal growth factor receptor mutations. *J Natl Cancer Inst.* 2005; 97:1185-1194.
30. Huang S, Armstrong E A, Benavente S, et al. Dual-agent molecular targeting of the epidermal growth factor receptor (EGFR): combining anti-EGFR antibody with tyrosine kinase inhibitor. *Cancer Res.* 2004; 64:5355-5362.
31. Pirazzoli V, Ayeni D, Meador C B, et al. Afatinib plus cetuximab delays resistance compared to single-agent erlotinib or afatinib in mouse models of TKI-naive EGFR L858R-induced lung adenocarcinoma. *Clin Cancer Res.* 2016; 22:426-435.
32. Sen M, Joyce S, Panahandeh M, et al. Targeting Stat3 abrogates EGFR inhibitor resistance in cancer. *Clin Cancer Res.* 2012; 18:4986-4996.
33. Zhang Z, Lee J C, Lin L, et al. Activation of the AXL kinase causes resistance to EGFR-targeted therapy in lung cancer. *Nat Genet.* 2012; 44:852-860.
34. Schulz D, Wirth M, Piontek G, et al. HNSCC cells resistant to EGFR pathway inhibitors are hypermutated and sensitive to DNA damaging substances. *Am J Cancer Res.* 2016; 6:1963-1975.
35. Codony-Servat C, Codony-Servat J, Karachaliou N, et al. Activation of signal transducer and activator of transcription 3 (STAT3) signaling in EGFR mutant non-small-cell lung cancer (NSCLC). *Oncotarget.* 2017; 8:47305-47316.
36. Hashida S, Yamamoto H, Shien K, et al. Acquisition of cancer stem cell-like properties in non-small cell lung cancer with acquired resistance to afatinib. *Cancer Sci.* 2015; 106:1377-1384.
37. Vouri M, Croucher D R, Kennedy S P, et al. Axl-EGFR receptor tyrosine kinase hetero-interaction provides EGFR with access to pro-invasive signalling in cancer cells. *Oncogenesis.* 2016; 5:e266.
38. Brand T M, Iida M, Stein A P, et al. AXL mediates resistance to cetuximab therapy. *Cancer Res.* 2014; 74:5152-5164.
39. Arasada R R, Amann J M, Rahman M A, et al. EGFR blockade enriches for lung cancer stem-like cells through notch3-dependent signaling. *Cancer Res.* 2014; 74:5572-5584.

What is claimed is:

1. A method of treating a patient suffering from a non-small cell lung cancer (NSCLC), or metastatic forms thereof, responsive to an Anaplastic Lymphoma Kinase (ALK) Inhibitor and expressing the ELM4-ALK fusion gene and a mutated form of an Epidermal Growth Factor Receptor (EGFR), comprising:

administering to the patient the ALK Inhibitor and an immunogenic polypeptide comprising amino acids cysteine 6 to cysteine 42 of an Epidermal Growth Factor (EGF) at an amount effective to generate an immune response against the EGF, wherein the cysteine residues are numbered relative to amino acids 1 to 52 of SEQ ID NO: 2, or an immunogenic polypeptide comprising SEQ ID NO: 2;

wherein the ALK Inhibitor is selected from the group consisting of Crizotinib, Ceritinib, Alectinib, Brigatinib, Lorlatinib, and pharmaceutically acceptable salts thereof;

wherein the ALK Inhibitor is administered in a therapeutically effective daily dose in a range of about 10 mg to about 250 mg and the immunogenic polypeptide is administered according to a therapeutically effective repeated thrice, twice or once a week, once in two weeks, once in three weeks or at least once monthly to generate polyclonal antibodies targeting EGF.

2. The method of claim 1, wherein the immunogenic polypeptide is administered prior to the ALK Inhibitor.

3. The method of claim 1, wherein the immunogenic polypeptide is administered at the same time as the ALK Inhibitor.

* * * * *

SEQUENCE LISTING

<160> NUMBER OF SEQ ID NOS: 20

<210> SEQ ID NO 1
<211> LENGTH: 681

<212> TYPE: DNA
<213> ORGANISM: Artificial
<220> FEATURE:
<223> OTHER INFORMATION: Synthetic

<400> SEQUENCE: 1

```
aataccgaaa acgattgccc tctgtctcat gaagcgtatt gtctgcacga cggcgtgtgt    60
atgtacattg aagccctgga caaatatgca tgtaactgtg tcgtgggcta cgtgggggag   120
cgatgtcagt ttcgagacct gcgttggtgg gatgcgcgcg gctcgagcgg taataccgaa   180
aacgattgcc ctctgtctca tgaagcgtat tgtctgcacg acggcgtgtg tatgtacatt   240
gaagccctgg acaaatatgc atgtaactgt gtcgtgggct acgtgggga gcgatgtcag   300
tttcgagacc tgcgttggtg ggatgcgcgc ggcgggtctg gaggtactag tggcggcggt   360
ggagggtcgg gtaccccgca gaacatcacc gacctgtgcg ccgagtacca caacacccag   420
atccacaccc tgaacgacaa gatcttctcg tacaccgaga gcctggccga taagcgtgaa   480
atggccatca tcaccttcaa gaacggtgcg accttccagg tggaggtccc gggtagccag   540
cacatcgatt cacagaagaa ggccatcgag cgtatgaagg acaccctgcg tatcgcctac   600
ctgaccgaag ccaaggtgga aaagctgtgc gtctggaaca caagacgcc gcacgccatc   660
gccgccatca gcatggccaa t                                             681
```

<210> SEQ ID NO 2
<211> LENGTH: 227
<212> TYPE: PRT
<213> ORGANISM: Artificial
<220> FEATURE:
<223> OTHER INFORMATION: Synthetic

<400> SEQUENCE: 2

```
Asn Thr Glu Asn Asp Cys Pro Leu Ser His Glu Ala Tyr Cys Leu His
1               5                   10                  15
Asp Gly Val Cys Met Tyr Ile Glu Ala Leu Asp Lys Tyr Ala Cys Asn
            20                  25                  30
Cys Val Val Gly Tyr Val Gly Glu Arg Cys Gln Phe Arg Asp Leu Arg
        35                  40                  45
Trp Trp Asp Ala Arg Gly Ser Ser Gly Asn Thr Glu Asn Asp Cys Pro
    50                  55                  60
Leu Ser His Glu Ala Tyr Cys Leu His Asp Gly Val Cys Met Tyr Ile
65                  70                  75                  80
Glu Ala Leu Asp Lys Tyr Ala Cys Asn Cys Val Val Gly Tyr Val Gly
                85                  90                  95
Glu Arg Cys Gln Phe Arg Asp Leu Arg Trp Trp Asp Ala Arg Gly Gly
            100                 105                 110
Ser Gly Gly Thr Ser Gly Gly Gly Gly Ser Gly Thr Pro Gln Asn
        115                 120                 125
Ile Thr Asp Leu Cys Ala Glu Tyr His Asn Thr Gln Ile His Thr Leu
    130                 135                 140
Asn Asp Lys Ile Phe Ser Tyr Thr Glu Ser Leu Ala Asp Lys Arg Glu
145                 150                 155                 160
Met Ala Ile Ile Thr Phe Lys Asn Gly Ala Thr Phe Gln Val Glu Val
                165                 170                 175
Pro Gly Ser Gln His Ile Asp Ser Gln Lys Lys Ala Ile Glu Arg Met
            180                 185                 190
Lys Asp Thr Leu Arg Ile Ala Tyr Leu Thr Glu Ala Lys Val Glu Lys
        195                 200                 205
```

```
Leu Cys Val Trp Asn Asn Lys Thr Pro His Ala Ile Ala Ala Ile Ser
        210                 215                 220
Met Ala Asn
225

<210> SEQ ID NO 3
<211> LENGTH: 14
<212> TYPE: PRT
<213> ORGANISM: Artificial
<220> FEATURE:
<223> OTHER INFORMATION: Synthetic

<400> SEQUENCE: 3

Gly Gly Ser Gly Gly Thr Ser Gly Gly Gly Gly Ser Gly
1               5                   10

<210> SEQ ID NO 4
<211> LENGTH: 3
<212> TYPE: PRT
<213> ORGANISM: Artificial
<220> FEATURE:
<223> OTHER INFORMATION: Synthetic

<400> SEQUENCE: 4

Ser Ser Gly
1

<210> SEQ ID NO 5
<211> LENGTH: 5
<212> TYPE: PRT
<213> ORGANISM: Artificial
<220> FEATURE:
<223> OTHER INFORMATION: Synthetic

<400> SEQUENCE: 5

Ser Ser Gly Gly Gly
1               5

<210> SEQ ID NO 6
<211> LENGTH: 3
<212> TYPE: PRT
<213> ORGANISM: Artificial
<220> FEATURE:
<223> OTHER INFORMATION: Synthetic

<400> SEQUENCE: 6

Ser Gly Gly
1

<210> SEQ ID NO 7
<211> LENGTH: 4
<212> TYPE: PRT
<213> ORGANISM: Artificial
<220> FEATURE:
<223> OTHER INFORMATION: Synthetic

<400> SEQUENCE: 7

Gly Ser Ser Gly
1

<210> SEQ ID NO 8
<211> LENGTH: 5
<212> TYPE: PRT
<213> ORGANISM: Artificial
<220> FEATURE:
<223> OTHER INFORMATION: Synthetic
```

```
<400> SEQUENCE: 8

Gly Gly Ser Gly Gly
1               5

<210> SEQ ID NO 9
<211> LENGTH: 5
<212> TYPE: PRT
<213> ORGANISM: Artificial
<220> FEATURE:
<223> OTHER INFORMATION: Synthetic

<400> SEQUENCE: 9

Gly Gly Gly Gly Ser
1               5

<210> SEQ ID NO 10
<211> LENGTH: 8
<212> TYPE: PRT
<213> ORGANISM: Artificial
<220> FEATURE:
<223> OTHER INFORMATION: Synthetic

<400> SEQUENCE: 10

Ser Ser Gly Gly Gly Ser Gly Gly
1               5

<210> SEQ ID NO 11
<211> LENGTH: 10
<212> TYPE: PRT
<213> ORGANISM: Artificial
<220> FEATURE:
<223> OTHER INFORMATION: Synthetic

<400> SEQUENCE: 11

Ser Ser Gly Gly Gly Gly Ser Gly Gly Gly
1               5                   10

<210> SEQ ID NO 12
<211> LENGTH: 7
<212> TYPE: PRT
<213> ORGANISM: Artificial
<220> FEATURE:
<223> OTHER INFORMATION: Synthetic

<400> SEQUENCE: 12

Thr Ser Gly Gly Gly Ser Gly
1               5

<210> SEQ ID NO 13
<211> LENGTH: 9
<212> TYPE: PRT
<213> ORGANISM: Artificial
<220> FEATURE:
<223> OTHER INFORMATION: Synthetic

<400> SEQUENCE: 13

Thr Ser Gly Gly Gly Gly Ser Gly Gly
1               5

<210> SEQ ID NO 14
<211> LENGTH: 11
<212> TYPE: PRT
<213> ORGANISM: Artificial
<220> FEATURE:
<223> OTHER INFORMATION: Synthetic
```

```
<400> SEQUENCE: 14

Ser Ser Gly Gly Gly Ser Gly Gly Ser Ser Gly
1               5                   10

<210> SEQ ID NO 15
<211> LENGTH: 12
<212> TYPE: PRT
<213> ORGANISM: Artificial
<220> FEATURE:
<223> OTHER INFORMATION: Synthetic

<400> SEQUENCE: 15

Gly Gly Ser Gly Gly Thr Ser Gly Gly Ser Gly
1               5                   10

<210> SEQ ID NO 16
<211> LENGTH: 12
<212> TYPE: PRT
<213> ORGANISM: Artificial
<220> FEATURE:
<223> OTHER INFORMATION: Synthetic

<400> SEQUENCE: 16

Ser Gly Gly Thr Ser Gly Gly Gly Ser Gly Gly
1               5                   10

<210> SEQ ID NO 17
<211> LENGTH: 14
<212> TYPE: PRT
<213> ORGANISM: Artificial
<220> FEATURE:
<223> OTHER INFORMATION: Synthetic

<400> SEQUENCE: 17

Gly Gly Ser Gly Gly Thr Ser Gly Gly Gly Ser Gly Gly
1               5                   10

<210> SEQ ID NO 18
<211> LENGTH: 13
<212> TYPE: PRT
<213> ORGANISM: Artificial
<220> FEATURE:
<223> OTHER INFORMATION: Synthetic

<400> SEQUENCE: 18

Ser Ser Gly Gly Gly Gly Ser Gly Gly Gly Ser Ser Gly
1               5                   10

<210> SEQ ID NO 19
<211> LENGTH: 13
<212> TYPE: PRT
<213> ORGANISM: Artificial
<220> FEATURE:
<223> OTHER INFORMATION: Synthetic

<400> SEQUENCE: 19

Ser Ser Gly Gly Gly Ser Gly Gly Ser Ser Gly Gly
1               5                   10

<210> SEQ ID NO 20
<211> LENGTH: 15
<212> TYPE: PRT
<213> ORGANISM: Artificial
```

```
<220> FEATURE:
<223> OTHER INFORMATION: Synthetic

<400> SEQUENCE: 20

Ser Ser Gly Gly Gly Ser Gly Gly Gly Ser Ser Gly Gly Gly
1               5                   10                  15
```